United States Patent [19]

Kondo et al.

[11] Patent Number: 5,720,899

[45] Date of Patent: Feb. 24, 1998

[54] LIQUID CRYSTALLINE COMPOUND, LIQUID CRYSTAL COMPOSITION AND LIQUID CRYSTAL DISPLAY ELEMENT

[75] Inventors: Tomoyuki Kondo; Kazutoshi Miyazawa; Atsuko Fujita; Noriyuki Ohnishi; Yasuyuki Goto; Etsuo Nakagawa; Shinichi Sawada, all of Chiba, Japan

[73] Assignee: Chisso Corporation, Osaka, Japan

[21] Appl. No.: 775,199

[22] Filed: Dec. 30, 1996

Related U.S. Application Data

[63] Continuation of Ser. No. 429,847, Apr. 27, 1995, Pat. No. 5,653,911.

[30] Foreign Application Priority Data

Apr. 28, 1994 [JP] Japan ................. 6-92740

[51] Int. Cl.[6] .................. C09K 19/52; C07C 25/13; C07D 239/02; G02F 1/13
[52] U.S. Cl. .................. 252/299.01; 252/299.61; 252/299.63; 252/299.64; 252/299.65; 349/182; 544/242; 546/326; 546/339; 546/346; 570/127; 570/129
[58] Field of Search .................. 252/299.01, 299.61, 252/299.63, 299.64, 299.65; 349/182; 544/242; 546/326, 339, 346; 570/127, 129

[56] References Cited

U.S. PATENT DOCUMENTS

| | | | |
|---|---|---|---|
| 5,183,587 | 2/1993 | Kitano et al. | 252/299.63 |
| 5,308,537 | 5/1994 | Coates et al. | 252/299.6 |
| 5,382,379 | 1/1995 | Onji et al. | 252/299.63 |
| 5,653,911 | 8/1997 | Kondo et al. | 252/299.01 |

FOREIGN PATENT DOCUMENTS

| | | |
|---|---|---|
| 0377469 | 7/1990 | European Pat. Off. |
| 0480217 | 4/1992 | European Pat. Off. |
| 4211694 | 11/1993 | Germany |
| 4222371 | 1/1994 | Germany |
| 90/13610 | 11/1990 | WIPO |
| 92/21734 | 12/1992 | WIPO |

*Primary Examiner*—Shean C. Wu
*Attorney, Agent, or Firm*—Wenderoth, Lind, & Ponack

[57] ABSTRACT

A novel liquid crystalline compound having a high elastic constant ratio ($K_{33}/K_{11}$) and an improved solubility thereof in other liquid crystal materials, at low temperatures, and a liquid crystal composition containing the same are provided. The liquid crystalline compound is expressed by the formula (1):

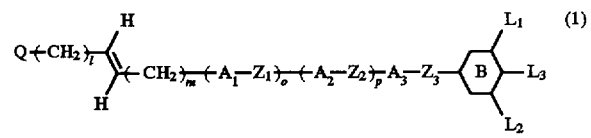

wherein Q represents $CF_3$, $CF_2H$ or $CFH_2$; $A_1$, $A_2$ and $A_3$ each independently represent trans-1,4-cyclohexylene group, 1,4-phenylene group, wherein one or more hydrogen atoms on its six-membered ring may be replaced by F, Cl or CN, pyridine-2,5-diyl group or 1,3-pyrimidine-2,5-diyl; ring B represents 1,4-phenylene group or trans-1,4-cyclohexylene group; $Z_1$, $Z_2$ and $Z_3$ each independently represent covalent bond, —C=C—, —C≡C—, —OCO—, —COO—, —$CH_2$O—, —O$CH_2$—, —$(CH_2)_2$— or —$(CH_2)_4$—; l and m each independently represent an integer of 0 to 5; o and p each independently represent 0 or 1; $L_1$ and $L_2$ each independently represent H, F or Cl; $L_3$ represents halogen atom, CN, $CF_3$, $CF_2H$, $CFH_2$, $OCF_3$, $OCF_2H$, H or an alkyl group of 1 to 10 carbon atoms or an alkenyl group of 2 to 10 carbon atoms wherein optional methylene groups (—$CH_2$—) in the alkyl group or the alkenyl group each independently may be replaced by —O—, —S—, —CO—, —OCO— or —COO—, but two or more methylene groups should not be continuedly replaced.

9 Claims, No Drawings

LIQUID CRYSTALLINE COMPOUND, LIQUID CRYSTAL COMPOSITION AND LIQUID CRYSTAL DISPLAY ELEMENT

This is a continuation application of Ser. No. 08/429,847 filed Apr. 27, 1995, now U.S. Pat. No. 5,653,911.

BACKGROUND OF THE INVENTION

1. Field of the Invention

This invention relates to a liquid crystalline compound and a liquid crystal composition. More particularly, it relates to a novel liquid crystalline compound containing a fluorine-substituted alkenyl group, a liquid crystal composition containing the same and a liquid crystal display element constituted by using the liquid crystal composition.

2. Description of the Related Art

Display elements using liquid crystalline compounds have been broadly utilized for watches, electronic calculators, word processors, etc. These display elements utilize optical anisotropy, dielectric anisotropy, etc.

Liquid crystal phases include nematic liquid crystal phase, smectic liquid crystal phase and cholesteric liquid crystal phase, but display elements utilizing nematic liquid crystal phase have been most broadly utilized. Further, the display modes include dynamic scattering (DS) mode, deformation of aligned phases (DAP) mode, guest-host (GH) mode, twisted nematic (TN) mode, supertwisted nematic (STN) mode, thin film transistor (TFT) mode, etc., but current mainstreams thereof are three modes of TN, STN and TFT. Among these, STN mode has been broadly used since it is collectively superior in the aspects of many characteristics such as display capacity, response speed, viewing angle, graduation property, etc., for liquid crystal display of simple matrix mode drive.

Liquid crystalline compounds used for thsese display modes should exhibit liquid crystal phases within a broad temperature range around room temperature, have a sufficient stability under conditions where the display elements are used and also have sufficient characteristics for driving the display elements, but at present, no single liquid crystalline compound satisfying these conditions has been found. Thus, it is the practical status that several kinds to several tens kinds of liquid crystalline compounds and if necessary, non-liquid crystalline compounds, have been blended to prepare liquid crystalline compounds furnished with required characteristics. These liquid crystal compositions are required to be stable to moisture, light, heat and air which are usually present under conditions where the display elements are used, and also stable to electric field or electromagnetic irradiation and moreover chemically stable to the blended compounds. Further, it is required for the liquid crystal compositions that values of various physical properties such as optical anisotropy value ($\Delta n$), dielectric anisotropy value ($\Delta \epsilon$), etc. are suitable, depending upon display mode and the shape of the display elements. Further, it is important for the respective components in the liquid crystal compositions to have good solubilities in each other.

Further, for the liquid crystalline compounds used for STN type display mode, it has been regarded as advantageous that the value of elastic constant ratio $K_{33}/K_{11}$ ($K_{33}$: bend elastic constant and $K_{11}$: splay elastic constant) is large (see M. Akatuka et al: Proc. of Japan Display, 86 (1989), 388). When the elastic constant ratio $K_{33}/K_{11}$ is made higher, change in the transmittance in the vicinity of thresold voltage becomes steep so that a display element of high contrast is obtained. As compounds having a higher elastic constant ratio of $K_{33}/K_{11}$, those having an alkenyl group on a side chain have been generally known (for example, see Japanese patent application laid-open No. Sho 61-83136, Japanese patent application laid-open No. Hei 1-151531, Japanese patent application laid-open No. Hei 1-157925, Japanese patent application No. Hei 2-104582, Japanese patent application laid-open No. Hei 3-223223, Japanese patent publication No. Hei 3-3643, Japanese patent application laid-open No. Hei 4-226929, Japanese patent application laid-open No. Hei 4-230352, Japanese patent publication No. Hei 4-30382, etc.). However, these compounds have a problem of being inferior in the solubility in liquid crystal compositions at low temperatures. Further, as compounds having a similar structure to that of the compound of the present invention, compounds disclosed in U.S. Pat. No. 5,183,587 have been known. However, these compounds have a problem of being far inferior in the heat stability. Thus, development of a liquid crystalline compound having a high elastic constant $K_{33}/K_{11}$, a superior heat stability and an improved solubility at low temperatures has been long waited for.

SUMMARY OF THE INVENTION

The object of the present invention is to provide a liquid crystalline compound having overcome the draw-backs of the above prior art, and particularly having a high elastic constant ratio $K_{33}/K_{11}$ and an improved solubility at low temperatures, a liquid crystal composition containing the same and a liquid crystal display element constructed by using the liquid crystal composition.

This object can be achieved by the liquid crystalline compounds of the present invention, which are expressed by the formula (1)

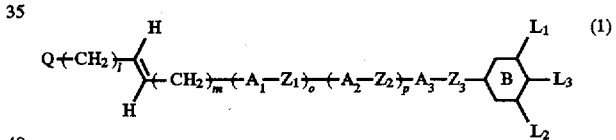

wherein Q represents $CF_3$, $CF_2H$ or $CFH_2$; $A_1$, $A_2$ and $A_3$ each independently represent trans-1,4-cyclohexylene group, 1,4-phenylene group wherein one or more hydrogen atoms on its six-membered ring may be replaced by F, Cl or CN, pyridine-2,5-diyl group or 1,3-pyrimidine-2,5-diyl; ring B represents 1,4-phenylene group or trans-1,4-cyclohexylene group $Z_1$, $Z_2$ and $Z_3$ each independently represent covalent bond, —CH=CH—, —C≡C—, —OCO—, —COO—, —$CH_2O$—, —$OCH_2$—, —$(CH_2)_2$— or —$(CH_2)_4$—; l and m each independently represent an integer of 0 to 5; o and p each independently represent 0 or 1; $L_1$ and $L_2$ each independently represent H, F or Cl; and $L_3$ represents a halogen atom, CN, $CF_3$, $CF_2H$, $CFH_2$, $OCF_3$, $OCF_2H$, H, an alkyl group of 1 to 10 carbon atoms or an alkenyl group of 2 to 10 carbon atoms (wherein optional methylene groups (—$CH_2$—) in the alkyl group or the alkenyl group each independently may be replaced by —O—, —S—, —CO—, —OCO— or —COO—, but two or more methylene groups should not be continuously replaced.

The liquid crystal composition of the present invention contain at least one of the liquid crystalline compounds of formula (I).

The liquid crystal composition containing as a first component, at least one of the liquid crystalline compounds of formula (I); may also contain as a second component, at least one compound chosen from those expressed by the following formulas (2), (3) or (4):

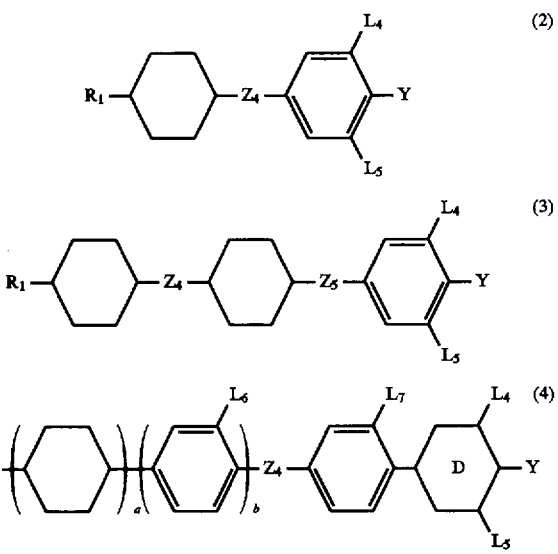

(2), (3), (4)

wherein $R_1$ represents an alkyl group of 1 to 10 carbon atoms; Y represents F, Cl, $CF_3$, $OCF_3$, $OCF_2H$ or an alkyl group of 1 to 10 carbon atoms; $L_4$, $L_5$, $L_6$ and $L_7$ each independently represent H or F; $Z_4$ and $Z_5$ each independently represent $—(CH_2)_2—$, $—CH=CH—$ or covalent bond; ring D represents trans-1,4-cyclohexylene group or 1,4-phenylene group; a represents 1 or 2; and b represents 0 or 1.

The liquid crystal composition containing as a first component, at least one of the liquid crystalline compounds of formula (I), may also containing as a second component, at least one compound chosen from those expressed by the following formulas (5), (6), (7), (8) and (9):

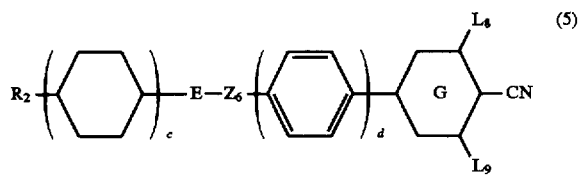

(5)

wherein $R_2$ represents F, an alkyl group of 1 to 10 carbon atoms or an alkenyl group of 2 to 10 carbon atoms wherein optional methylene groups ($—CH_2—$) may be replaced by oxygen atom ($—O—$), but two or more methylene groups should not be continuedly replaced by oxygen atom; $Z_6$ represents $—(CH_2)_2—$, $—COO—$ or covalent bond; $L_8$ and $L_9$ each independently represent H or F; E represents trans-1,4-cyclohexylene group, 1,4-phenylene group or 1,3-dioxane-2,5-diyl group; ring G represents trans-1,4-cyclohexylene group or 1,4-phenylene group; and c and d each independently represent 0 or 1,

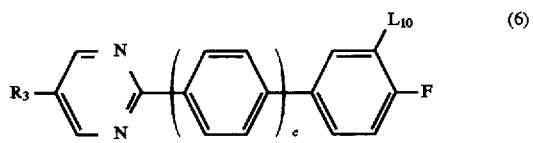

(6)

wherein $R_3$ represents an alkyl group of 1 to 10 carbon atoms; $L_{10}$ represents H or F; and e represents 0 or 1,

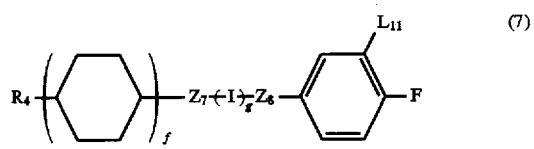

(7)

wherein $R_4$ represents an alkyl group of 1 to 10 carbon atoms; I represents trans-1,4-cyclohexylene group or 1,4-phenylene group; $L_{11}$ represents H or F; $Z_7$ represents $—COO—$ or covalent bond; $Z_8$ represents $—COO—$ or $—C\equiv C—$; and f and g each independently represent 0 or 1,

(8)

wherein $R_5$ and $R_6$ each independently represent an alkyl group, an alkoxy group or an alkoxymethyl group of each 1 to 10 carbon atoms; J represents trans-1,4-cyclohexylene group, 1,4-phenylene group or 1,3-pyrimidine-2,5-diyl group; K represents trans-1,4-cyclohexylene group or 1,4-phenylene group; and $Z_9$ represents $—C\equiv C—$, $—COO—$, $—(CH_2)_2—$ or covalent bond,

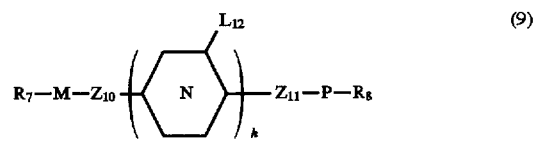

(9)

wherein $R_7$ represents an alkyl group or an alkoxy group of each 1 to 10 carbon atoms; $R_8$ represents an alkyl group of 1 to 10 carbon atoms; wherein optional methylene groups ($—CH_2—$) may be replaced by oxygen atom ($—O—$), but two or more methylene groups should not be continuedly replaced by oxygen atom; M represents trans-1,4-cyclohexylene group or 1,3-pyrimidine-2,5-diyl group; rings N and P each independently represent trans-1,4-cyclohexylene group or 1,4-phenylene group; $Z_{10}$ represents $—COO—$, $—(CH_2)_2—$, $—CH=CH—$ or covalent bond; $Z_{11}$ represents $—C\equiv C—$, $—COO—$ or covalent bond; h represents 0 or 1; and $L_{12}$ represents H or F.

DETAILED DESCRIPTION OF THE INVENTION

The liquid crystalline compounds expressed by the formula (I) of the present invention are characterized by having a fluoroalkenyl group in their molecules. These liquid crystalline compounds particularly have a high elastic constant ratio $K_{33}/K_{11}$ and a good solubility in liquid crystal compositions even at low temperatures. Further, these liquid crystalline compounds have a physically and chemically sufficient stability under conditions where display elements are usually used, and further, can be derived into those having desired physical values by suitably choosing the six-membered ring, substituent or bonding group among the molecule-constituting elements. Thus, when the compounds of the present invention are used as components of liquid crystal compositions, it is possible to provide novel liquid crystal compositions having preferable characteristics.

Hereinafter, when S represents the following group:

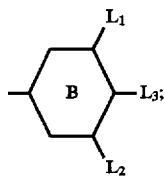

$R_9$ represents the following group:

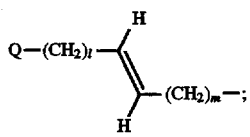

Cyc represents trans-1,4-cyclohexylene group;
Phe represents 1,4-phenylene group;
Pyd represents pyridine-2,5-diyl group;
Pyr represents 1,3-pyrimidine -2,5-diyl;
One or more hydrogen atoms of the Phe, Pyd and Pyr may be replaced by F, Cl or CN; and
$A_1$, $A_2$ and $A_3$ are chosen from the group consisting Cyc, Phe, Pyd and Pyr, and preferably do not contain two or more Pyds and Pyrs in the molecule,
then the compounds expressed by the formula (1) are classified as follows:

Compounds having two six-membered rings:

| | |
|---|---|
| $R_9-A_3-S$ | (1a) |
| $R_9-A_3-Z_3-S$ | (1b) |

Compounds having three six-membered rings:

| | |
|---|---|
| $R_9-A_2-A_3-S$ | (1c) |
| $R_9-A_2-Z_2-A_3-S$ | (1d) |
| $R_9-A_2-A_3-Z_3-S$ | (1e) |
| $R_9-A_2-Z_2-A_3-Z_3-S$ | (1f) | and compounds having four six-membered rings:

| | |
|---|---|
| $R_9-A_2-A_3-S$ | (1g) |
| $R_9-A_1Z_1-A_2-A_3-S$ | (1h) |
| $R_9-A_1-A_2-Z_2-S$ | (1i) |
| $R_9-A_1-A_2-A_3-Z_3-S$ | (1j) |
| $R_9-A_1-Z_1-A_2-Z_2-A_3-S$ | (1k) |
| $R_9-A_1-A_2-Z_2-A_3-Z_3-S$ | (1l) |
| $R_9-A_1-Z_1-A_2-A_3-Z_3-S$ | (1m) |
| $R_9-A_1-Z_1-A_2-Z_2-A_3-Z_3-S$ | (1n) |

Among these compounds, those expressed by the formulas (1a), (1b), (1c), (1d), (1e), (1g) and (1i) are particularly preferred in the aspect of achieving the object of the present invention.

Compounds expressed by the formula (1a) are further developed to those expressed by the following formulas (1aa) to (1ad):

| | |
|---|---|
| $R_9$-Cyc-S | (1aa) |
| $R_9$-Phe-S | (1ab) |
| $R_9$-Pyd-S | (1ac) |
| $R_9$-Pyr-S | (1ad) |

Among these compounds, those expressed by the formulas (1aa) and (1ab) are particularly preferred.

Further, the compounds expressed by the formula (1b) are further developed to those expressed by the following formulas (1ba) to (1bh):

| | |
|---|---|
| $R_9-A_3-CH=CH-S$ | (1ba) |
| $R_9-A_3-C\equiv C-S$ | (1bb) |
| $R_9-A_3-OCO-S$ | (1bc) |
| $R_9-A_3-COO-S$ | (1bd) |
| $R_9-A_3-CH_2O-S$ | (1be) |
| $R_9-A_3-OCH_2-S$ | (1bf) |
| $R_9-A_3-(CH_2)_2-S$ | (1bg) |
| $R_9-A_3-(CH_2)_4-S$ | (1bh) |

Among these compounds, those expressed by the formulas (1bd) and (1bg) are particularly preferred.

Further, compounds expressed by the formula (1c) are further developed to those expressed by the following formulas (1ca) to (1ch):

| | |
|---|---|
| $R_9$-Cyc-Cyc-S | (1ca) |
| $R_9$-Cyc-Phe-S | (1cb) |
| $R_9$-Phe-Cyc-S | (1cc) |
| $R_9$-Phe-Phe-S | (1cd) |
| $R_9$-Pyd-Phe-S | (1ce) |
| $R_9$-Pyr-Phe-S | (1cf) |
| $R_9$-Cyc-Pyr-S | (1cg) |
| $R_9$-Phe-Pyr-S | (1ch) |

Among these compounds, those expressed by the formulas (1ca), (1cb) and (1cf) are particularly preferred.

Compounds expressed by the formula (1d) are further developed to those expressed by the following formulas (1da) to (1dg):

| | |
|---|---|
| $R_9$-Cyc-$Z_2$-Cyc-S | (1da) |
| $R_9$-Cyc-$Z_2$-Phe-S | (1db) |
| $R_9$-Cyc-$Z_2$-Pyr-S | (1dc) |
| $R_9$-Phe-$Z_2$-Phe-S | (1dd) |
| $R_9$-Phe-$Z_2$-Cyc-S | (1de) |
| $R_9$-Phe-$Z_2$-Pyr-S | (1df) |
| $R_9$-Pyr-$Z_2$-Phe-S | (1dg) |

Among these compounds, those expressed by the formulas (1da) and (1db) are particularly preferred.

Compounds expressed by the formula (1e) are further developed to those expressed by the following formulas (1ea) to (1eh):

| | |
|---|---|
| $R_9$-Cyc-Cyc-$Z_3$-S | (1ea) |

R₉-Cyc-Phe-Z₃-S (1eb)

R₉-Cyc-Pyr-Z₃-S (1ec)

R₉-Phe-Phe-Z₃-S (1ed)

R₉-Phe-Cyc-Z₃-S (1ee)

R₉-Phe-Pyr-Z₃-S (1ef)

R₉-Pyr-Phe-Z₃-S (1eg)

R₉-Pyr-Cyc-Z₃-S (1eh)

Among these compounds, those expressed by the formulas (1ea) and (1eb) are particularly preferred.

Compounds expressed by the formula (1f) are further developed to those expressed by the following formulas:

R₉-Cyc-Z₂-Cyc-Z₃-S (1fa)

R₉-Cyc-Z₂-Phe-Z₃-S (1fb)

R₉-Cyc-Z₂-Pyr-Z₃-S (1fc)

R₉-Phe-Z₂-Phe-Z₃-S (1fd)

R₉-Phe-Z₂-Cyc-Z₃-S (1fe)

R₉-Phe-Z₂-Pyr-Z₃-S (1ff)

R₉-Pyr-Z₂-Phe-Z₃-S (1fg)

R₉-Pyr-Z₂-Cyc-Z₃-S (1fh)

In all of the above compounds, $R_9$ represents an alkenyl group of 3 to 13 carbon atoms wherein hydrogen atoms at ω-position are replaced by one or more fluorine atoms, and among the group, particularly preferable groups are as follows:

3-fluoro-1-propenyl, 4-fluoro-1-butenyl, 5-fluoro-1-pentenyl, 6-fluoro-1-hexenyl, 7-fluoro-1-heptenyl, 3,3-difluoro-1-propenyl, 4,4-difluoro-1-butenyl, 5,5-difluoro-1-pentenyl, 6,6-difluoro-1-hexenyl, 7,7-difluoro-1-heptenyl, 3,3,3-trifluoro-1-propenyl, 4,4,4-trifluoro-1-butenyl, 5,5,5-trifluoro-1-pentenyl, 6,6,6-trifluoro-1-hexenyl, 7,7,7-trifluoro-1-heptenyl, 5-fluoro-3-pentenyl, 6-fluoro-3-hexenyl, 7-fluoro-3-heptenyl, 5,5-difluoro-3-pentenyl, 6,6-difluoro-3-hexenyl, 7,7-difluoro-3-heptenyl, 5,5,5-trifluoro-3-penteny, 6,6,6-trifluoro-3-hexenyl and 7,7,7-trifluoro-3-heptenyl.

Further, as to group S, those wherein one or both of $L_1$ and $L_2$ are F are preferred, and in the case where $L_3$ represents an alkyl group wherein optional methylene groups (—CH₂—) each independently may be replaced by —O—, —S—, —CO—, —OCO— or —COO—, but two or more methylene groups should not be continuously replaced, those wherein $L_1$ and $L_2$ are both H are preferred.

As described above, compounds expressed by the formulas (1aa), (1ab), (1bd), (1bg), (1ca), (1cb), (1cf), (1da), (1db), (1ea) and (1eb) can be said to be particularly preferable examples, and as more preferable compounds among them, those expressed by the following formulas (1-1) to (1-10) can be mentioned:

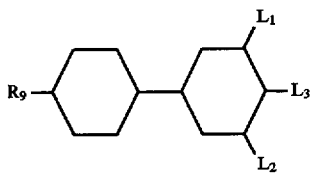(1-1)

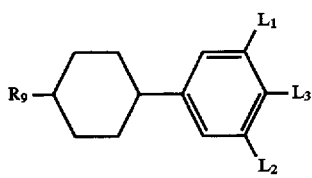(1-2)

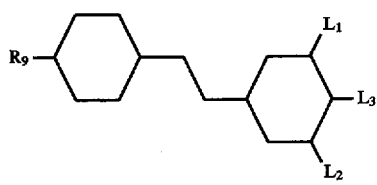(1-3)

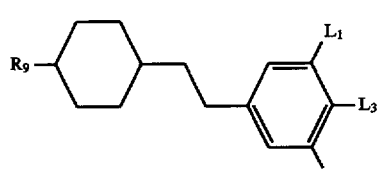(1-4)

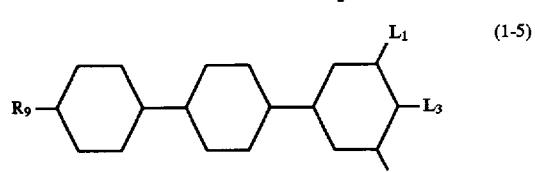(1-5)

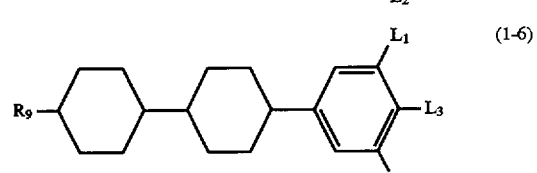(1-6)

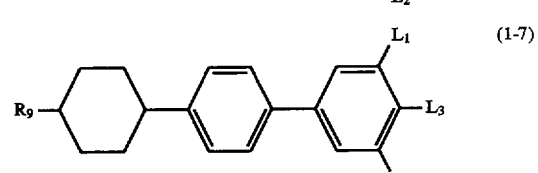(1-7)

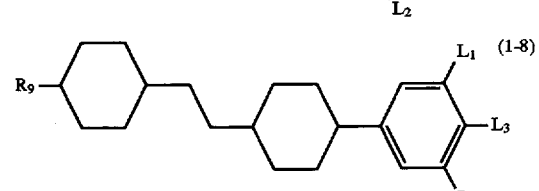(1-8)

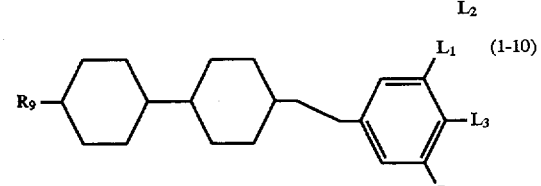(1-10)

The liquid crystalline compounds expressed by the formula (1) of the present invention can be prepared according to known processes employing Wittig reaction, for example based upon the process described in Organic Reactions, vol. 14, chapter 3, U.S. Pat. No. 4,676,604, etc., as follows:

p-toluenesulfinic acid, it is possible to prepare the compound (1) of the present invention.

Further, it is also possible that the aldehyde (11) is reacted

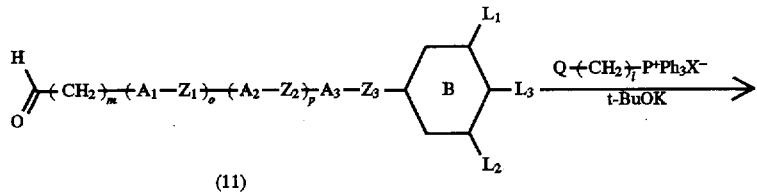

(11)

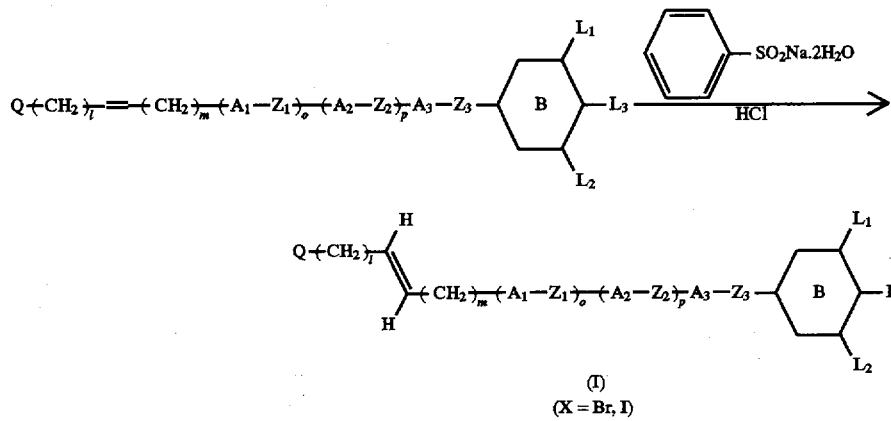

(I)
(X = Br, I)

Namely, a fluoroalkyltriphenylphosphonium halide is reacted with an aldehyde (11), in the presence of a base such as potassium-t-butoxide (t-BuOK), n-butyllithium (n-BuLi), etc., in a solvent of an ether such as tetrahydrofuran (THF), diethyl ether, etc. This reaction is preferably carried out at −20° to 0° C. in an inert gas current. Next, when the thus obtained compound is reacted with benzenesulfinic acid or with (ω-(1,3-dioxan-2-yl)alkyltriphenylphosphonium halide to obtain an intermediate (12), followed by removing the protective group therefrom to obtain an aldehyde (13), reacting this aldehyde (13) with a fluorinating agent such as diethylaminosulfurtrifluoride (DAST) to obtain an intermediate (14), and isomerizing it to obtain an objective compound example (15).

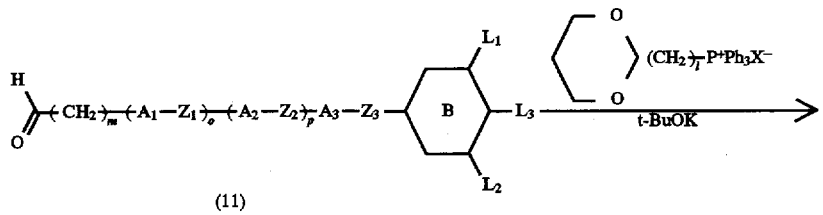

(11)

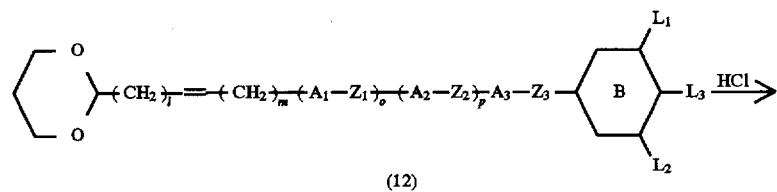

(12)

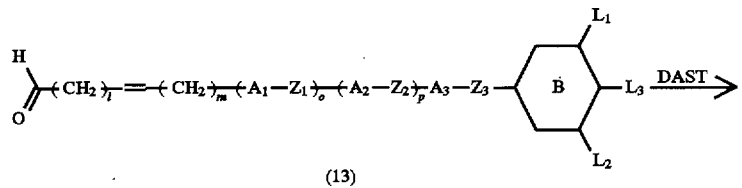

(13)

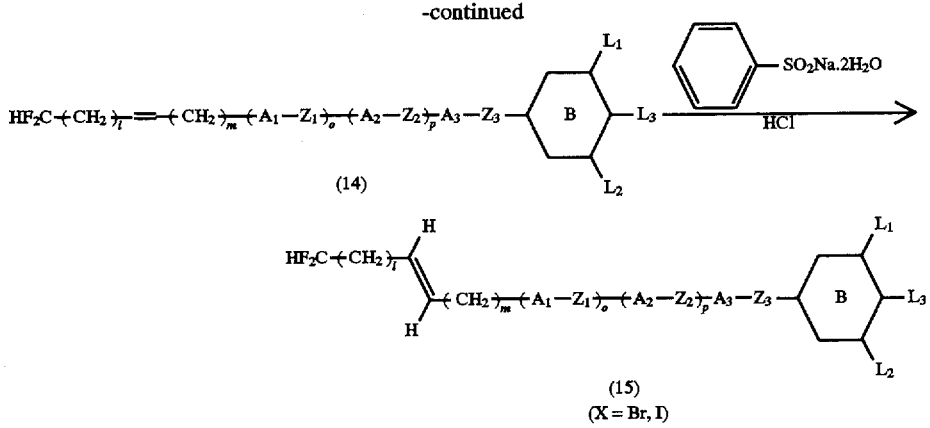

Still further, it is also possible that the aldehyde (13) is reduced with a reducing agent such as sodium boron hydride (SBH), lithium aluminum hydride (LAH), etc. to obtain an alcohol (16), followed by isomerizing the resulting intermediate (17), to obtain the objective compound example (18).

as toluene, xylene, etc. The above reaction of the fluoroalkylhalide with triphenylphosphine can also be carried out in the absence of any solvent and in a sealed tube. These reactions are preferably carried out at 60° to 100° C. and further in an inert gas current.

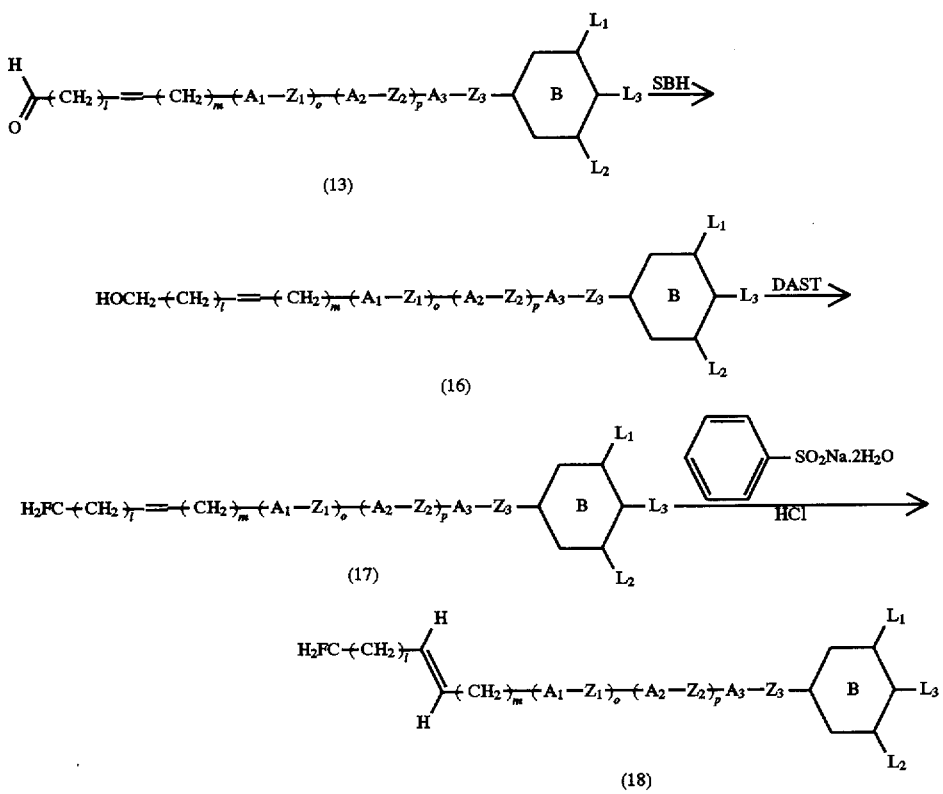

In addition, the above fluoroalkyltriphenylphosphonium halide can be prepared according to the following process:

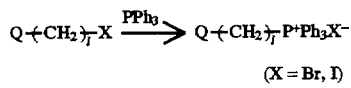

Namely, it is prepared by reacting the corresponding fluoroalkylhalide with triphenylphosphine in a solvent such Further, the aldehyde (11) as the starting raw material can be easily derived from the corresponding cyclohexanone, alcohol, carboxylic acid, etc. according to known process.

Next, the compound expressed by the formula (1) wherein the ring B represents a substituted phenylene group and $L_3$ represents $OCF_3$ or $OCF_2H$ can be prepared for example according to the following process:

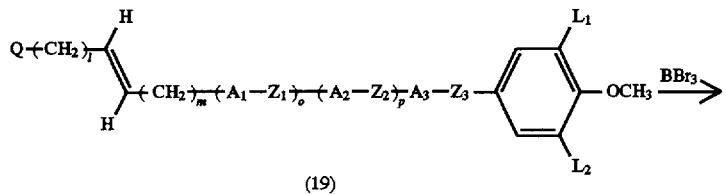
(19)

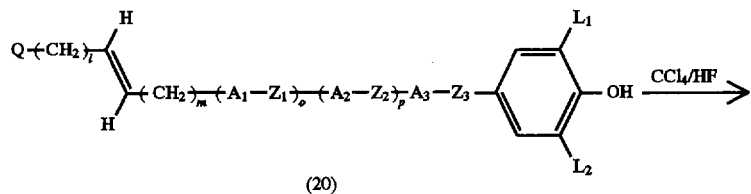
(20)

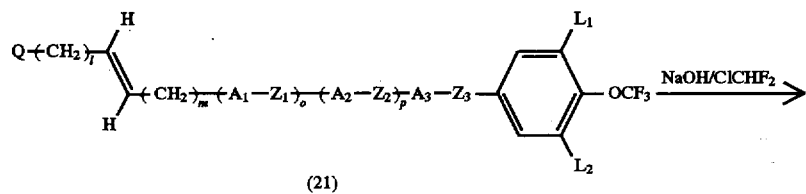
(21)

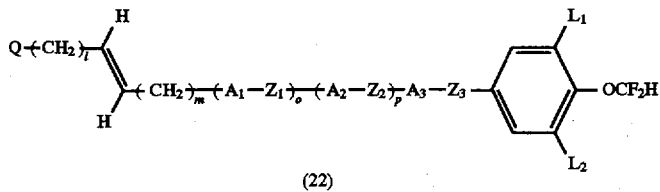
(22)

Namely, it is possible that the compound (19) is obtained according to Wittig reaction, followed by reacting it with boron tribromide to obtain a phenol (20), reacting it in a system of HF/CCl$_4$ or chlorodifluoromethane/NaOH to obtain the corresponding objective compound example (21) or (22). These compounds can also be obtained by subjecting a trifluoromethoxy or difluoromethoxy derivative of 4-substituted bromobenzene to a known coupling reaction, Wittig's reaction, etc.

The compound expressed by the formula (1) wherein ring B represents a substituted phenylene group and L$_3$ represents CF$_2$H or CFH$_2$, can be prepared according to the following process:

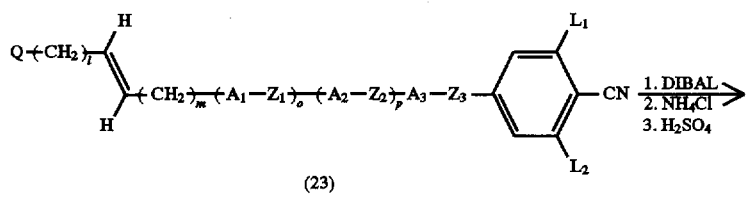
(23)

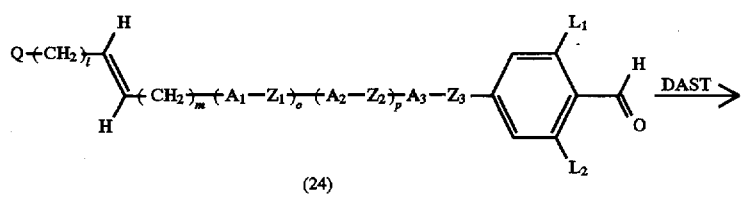
(24)

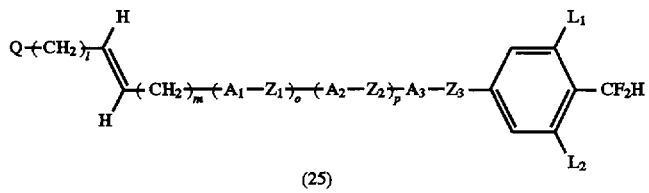
(25)

-continued

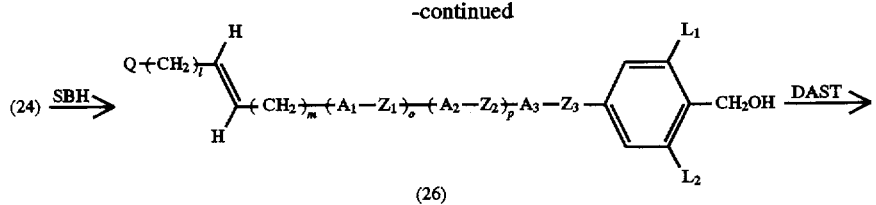

(26)

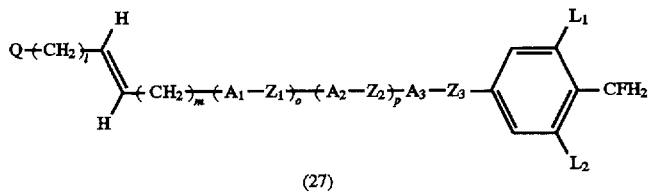

(27)

Namely, it is possible that a compound (23) is obtained according to Wittig reaction, followed by reducing (23) with a reducing agent such as diisobutylaluminum hydride (DIBAL), etc. to obtain an aldehyde (24), followed by reacting the aldehyde (24) with a fluorinating agent such as DAST, etc. to obtain the objective compound exmaple (25). Further, it is also possible that the aldehyde (24) is reduced with a reducing agent such as SBH, etc. to obtain an alcohol (26), followed by fluorinating the hydroxyl group of the alcohol with DAST, etc. to obtain the objective compound example (27).

The compound expressed by the formula (1) wherein ring B represents a substituted phenylene group and $L_3$ represents $CF_3$, can be obtained for example by subjecting a trifluoromethyl derivative of a substituted bromobenzene to known coupling reaction, Wittig reaction, etc.

Any of the thus obtained liquid crystalline compounds of the present invention exhibit a high elastic constant ratio ($K_{33}/K_{11}$), and further, are easily blended with various liquid crystal materials and have a good solubility at low temperatures; hence they are far superior as the constituting component of nematic liquid crystal compositions, particularly nematic liquid crystal compositions suitable to STN mode display elements.

The liquid crystal compositions provided by the present invention are enough to contain only a first component containing at least one kind of the liquid crystalline compounds expressed by the formula (1), but the first component is preferably mixed with, as a second component, at least one kind of compounds chosen from those expressed by the above formulas (2), (3) and (4) (hereinafter referred to as a second A component) and/or at least one kind of compounds chosen from those expressed by the formulas (5), (6), (7), (8) and (9) (hereinafter referred to as a second B component), and further a known compound can be also mixed as a third component, in order to adjust the threshold voltage, the liquid crystal temperature range, the optical anisotropy, the dielectric anisotropy, viscosity, etc.

Among compounds of the second A component, the following (2-1) to (2-15) are mentioned as preferable examples of compounds included in the formula (2); the following (3-1) to (3-48) are mentioned as preferable examples of compounds included in the formula (3); and the following (4-1) to (4-41) are mentioned as preferable examples of compounds included in the formula (4):

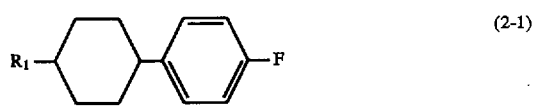 (2-1)

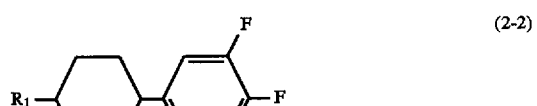 (2-2)

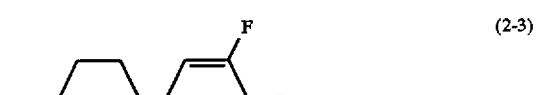 (2-3)

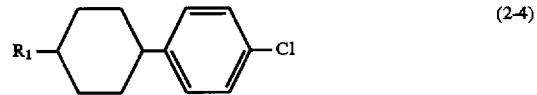 (2-4)

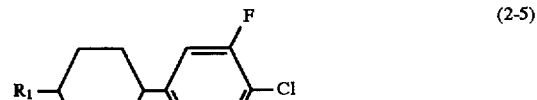 (2-5)

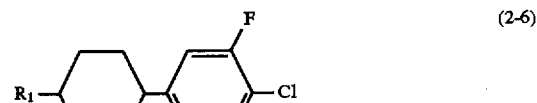 (2-6)

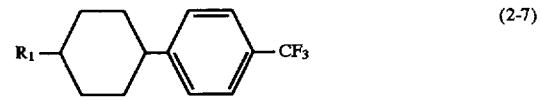 (2-7)

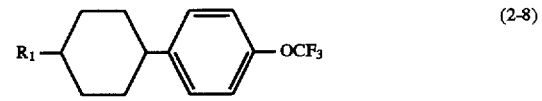 (2-8)

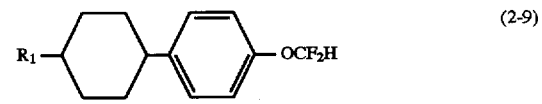 (2-9)

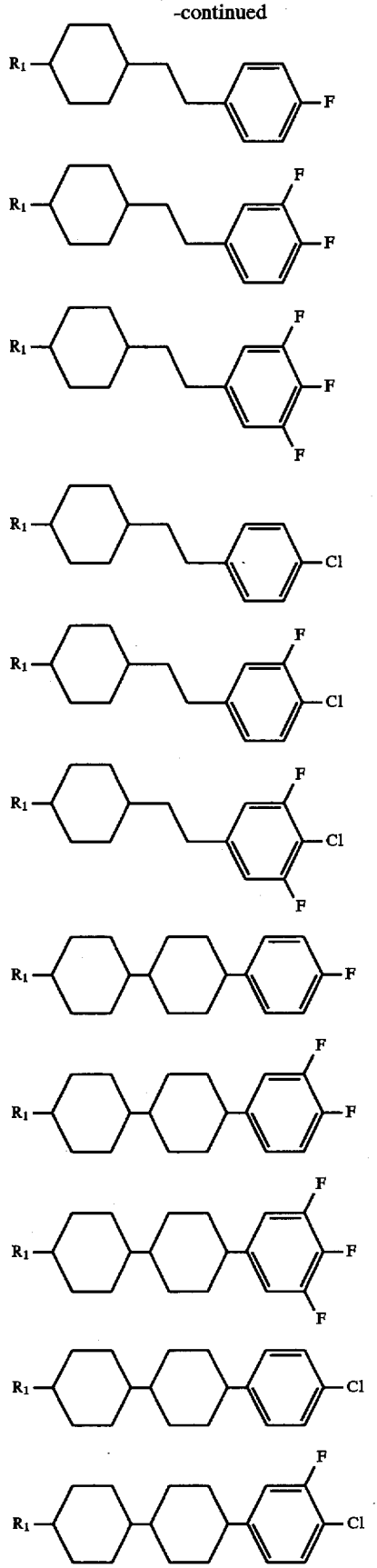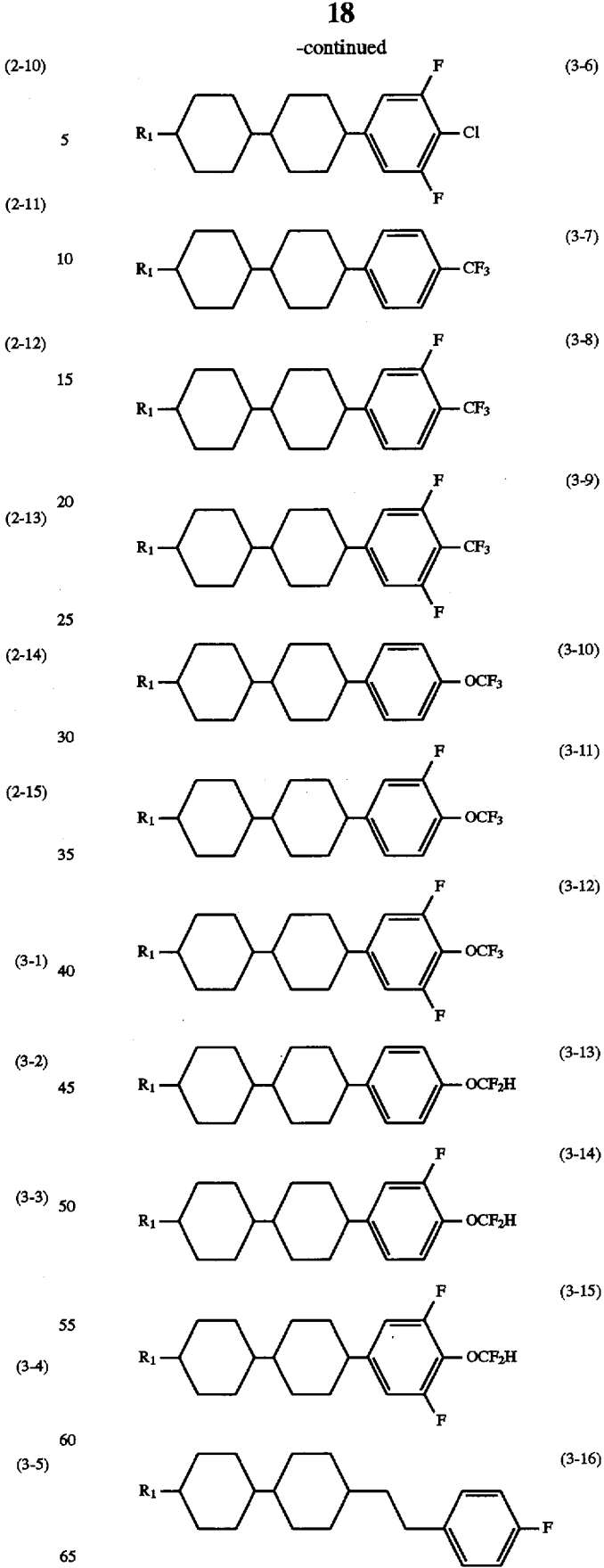

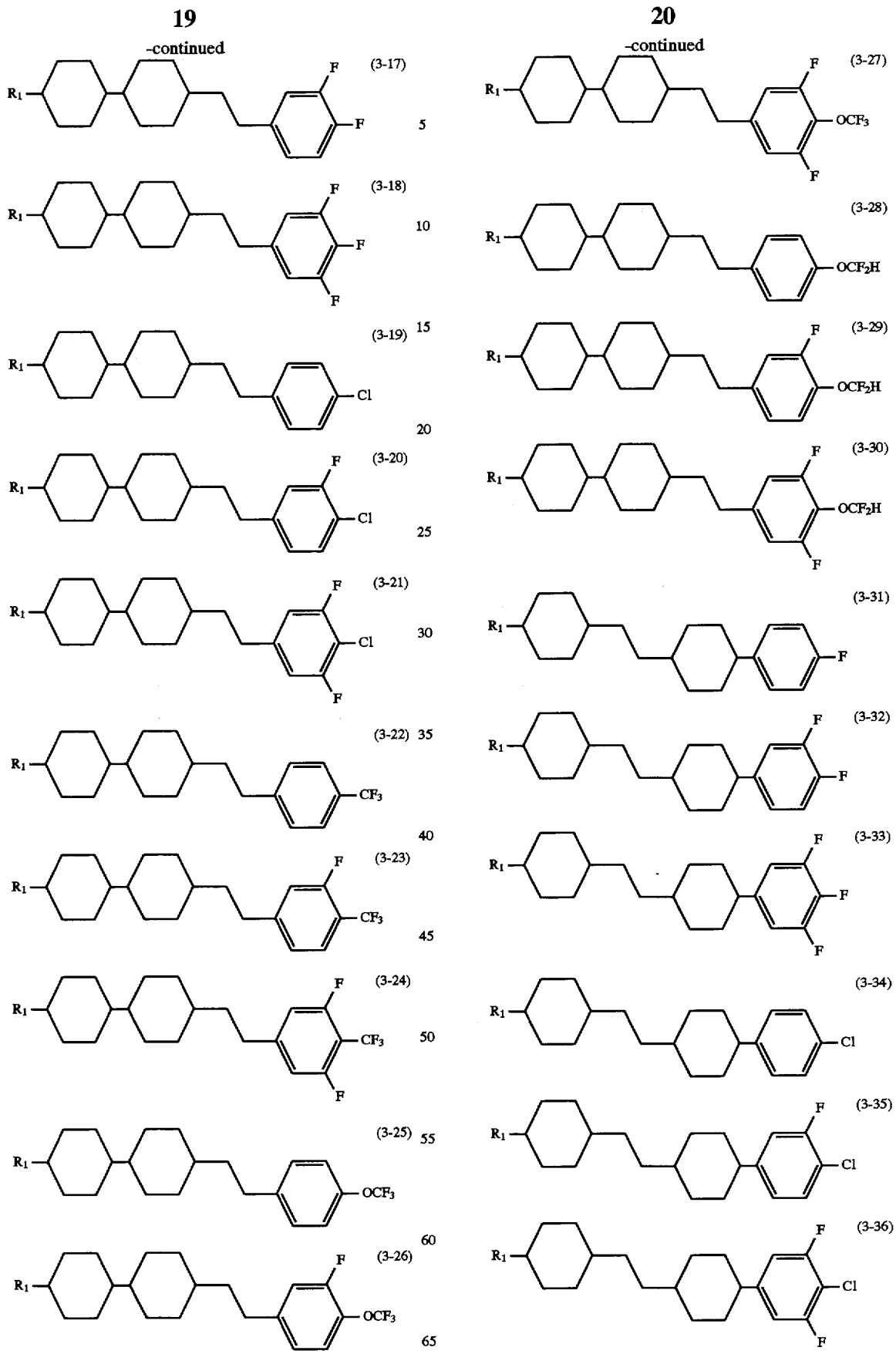

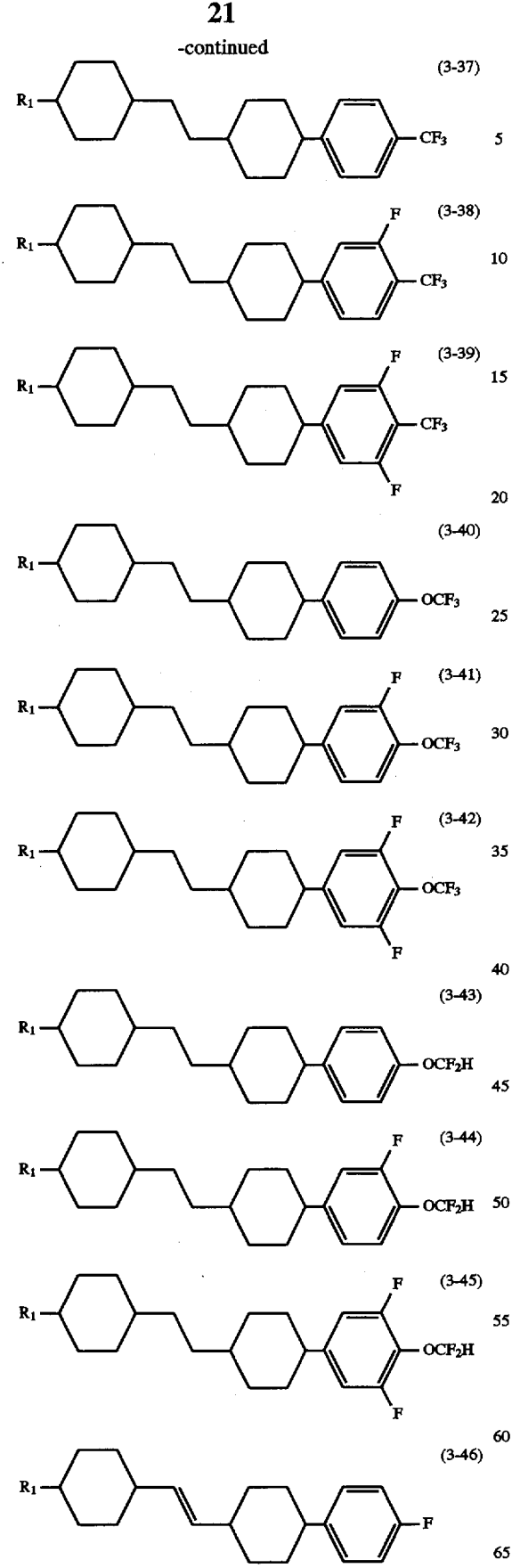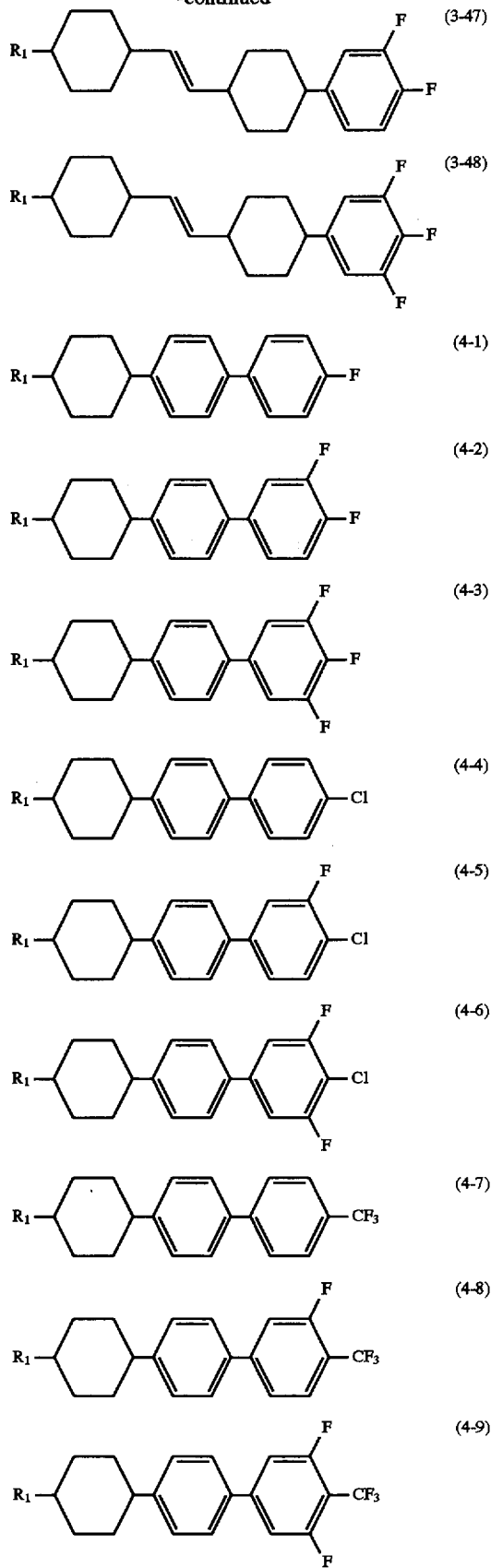

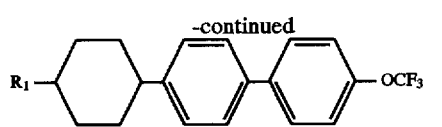 (4-10)
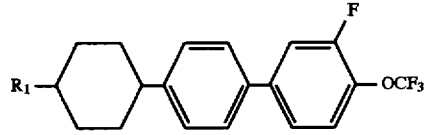 (4-11)
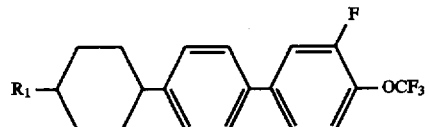 (4-12)
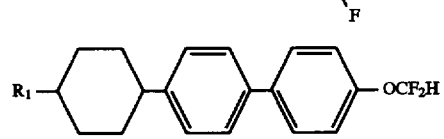 (4-13)
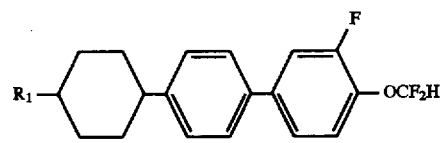 (4-14)
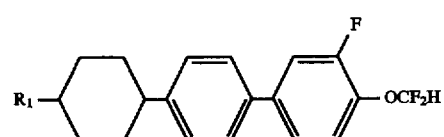 (4-15)
 (4-16)
 (4-17)
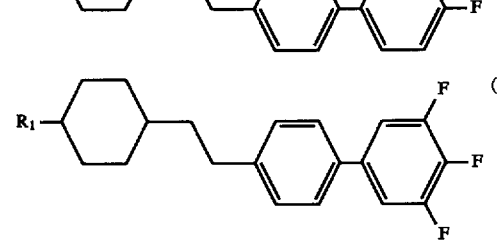 (4-18)
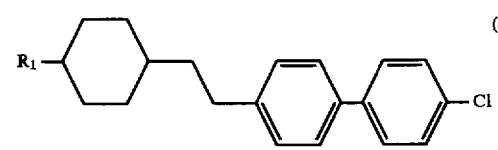 (4-19)
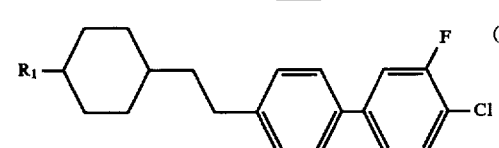 (4-20)
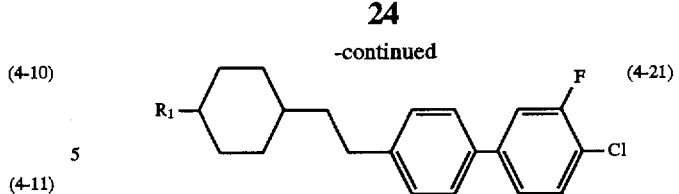 (4-21)
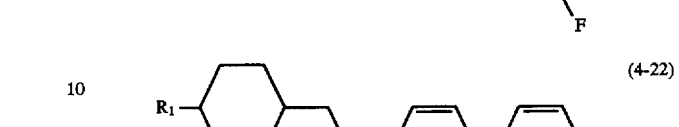 (4-22)
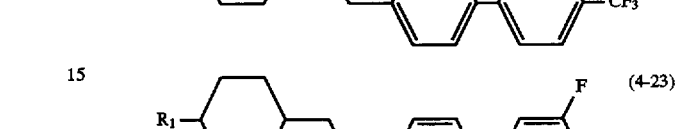 (4-23)
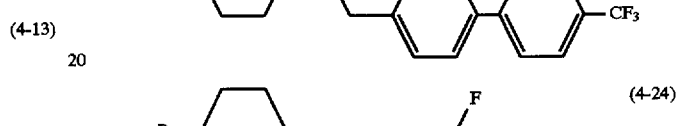 (4-24)
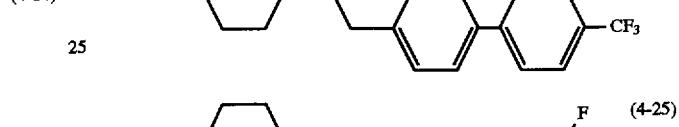 (4-25)
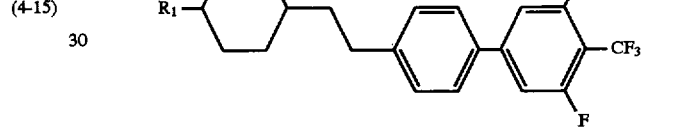 (4-26)
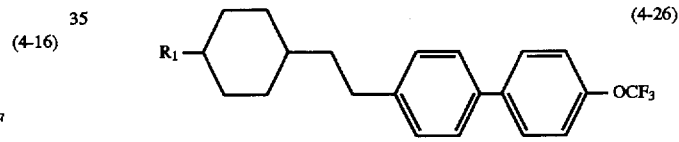 (4-27)
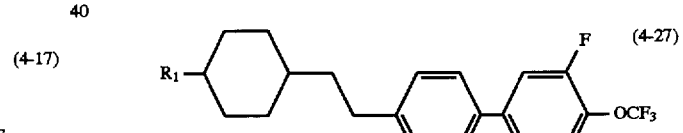 (4-28)
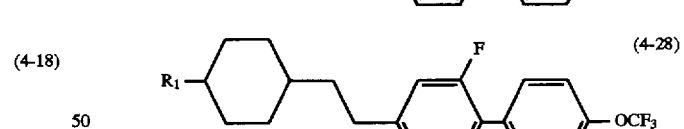 (4-29)
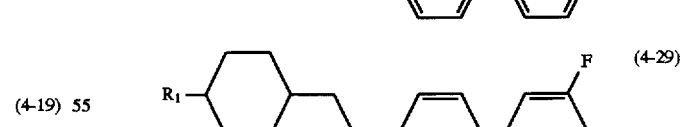 (4-29)
 (4-30)
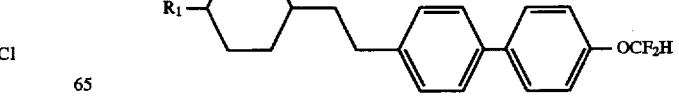

-continued

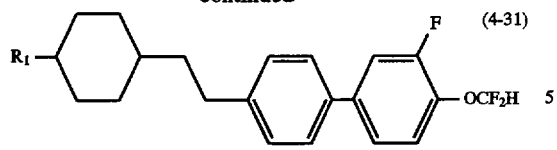 (4-31)

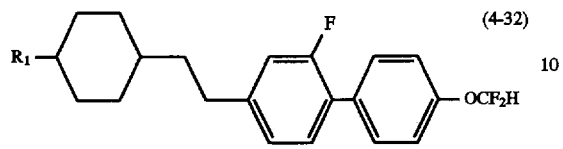 (4-32)

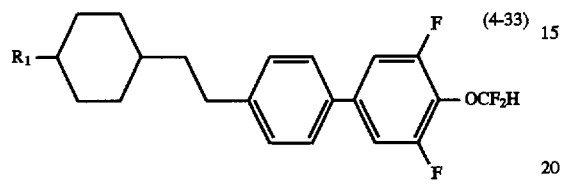 (4-33)

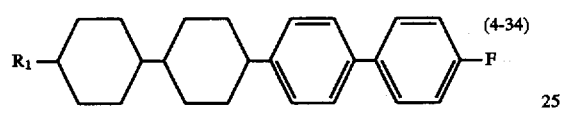 (4-34)

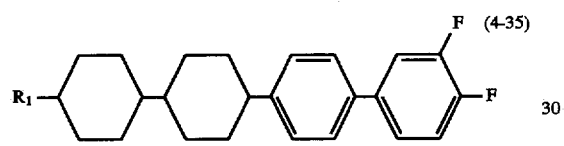 (4-35)

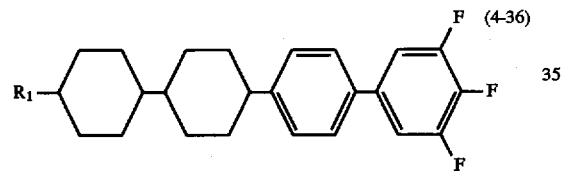 (4-36)

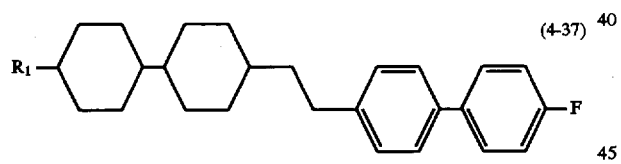 (4-37)

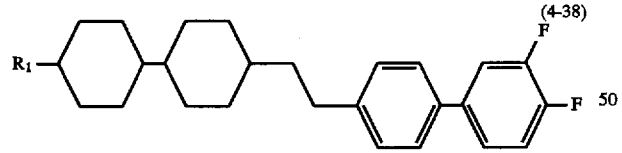 (4-38)

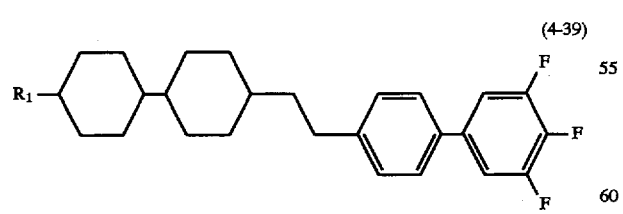 (4-39)

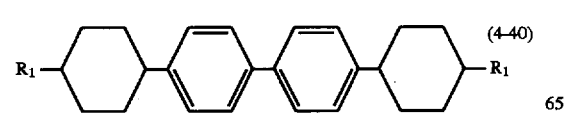 (4-40)

-continued

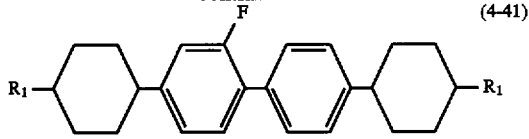 (4-41)

These compounds expressed by the formulas (2) to (4) exhibit positive dielectric anisotropy and are far superior in the heat stability and the chemical stability.

The quantity of these compounds used is in the range of 1 to 99% by weight, preferably 10 to 97% by weight and more preferably 40 to 95% by weight.

Next, among compounds of the second B components, the following (5-1) to (5-27), (6-1) to (6-3) and (7-1) to (7-11) are mentioned as preferable exmaples of compounds included in the formulas (5), (6) and (7), respectively:

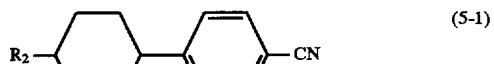 (5-1)

 (5-2)

 (5-3)

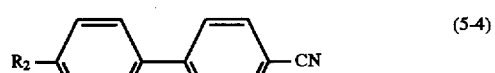 (5-4)

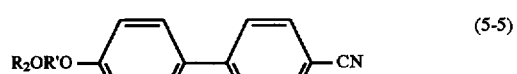 (5-5)

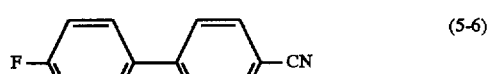 (5-6)

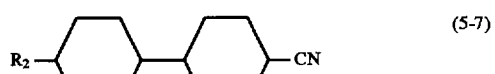 (5-7)

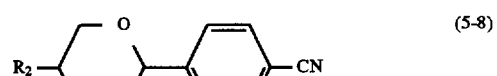 (5-8)

 (5-9)

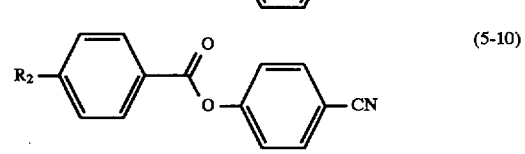 (5-10)

-continued
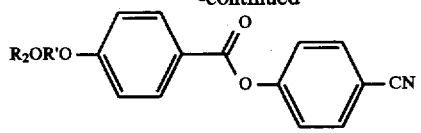 (5-11)
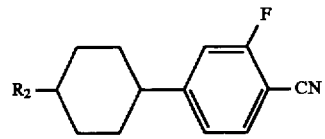 (5-12)
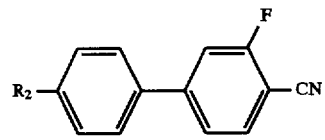 (5-13)
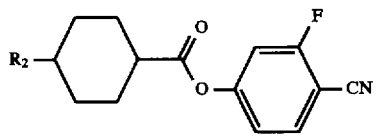 (5-14)
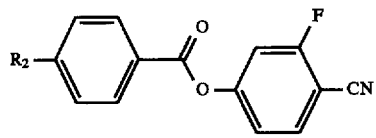 (5-15)
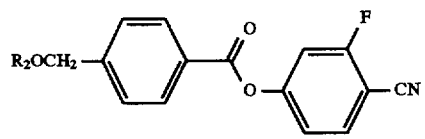 (5-16)
 (5-17)
 (5-18)
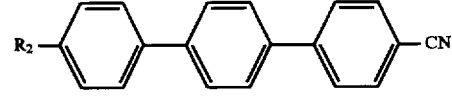 (5-19)
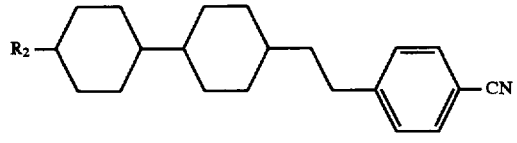 (5-20)
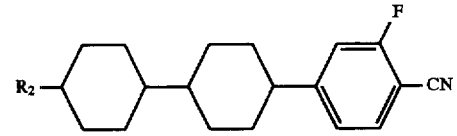 (5-21)
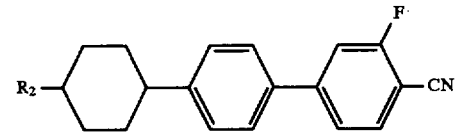 (5-22)
-continued
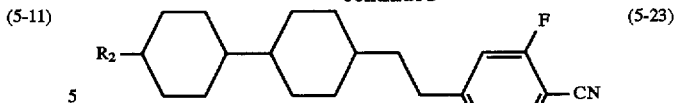 (5-23)
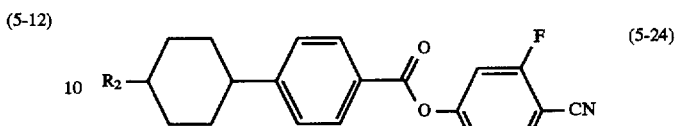 (5-24)
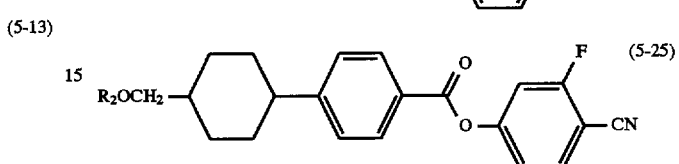 (5-25)
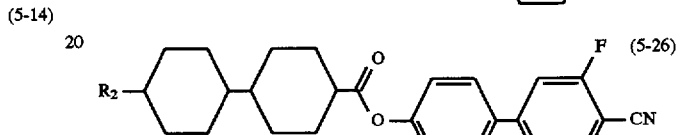 (5-26)
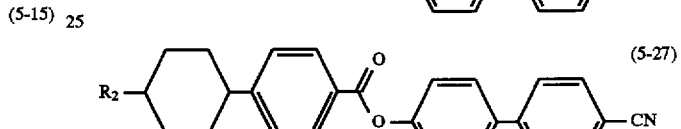 (5-27)
(R' represents an alkylene)
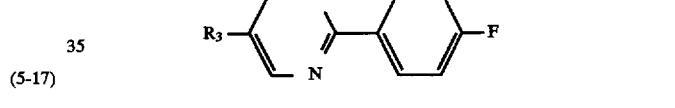 (6-1)
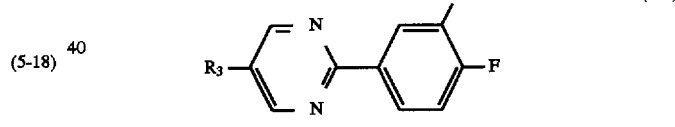 (6-2)
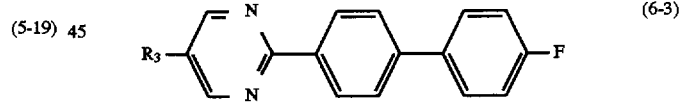 (6-3)
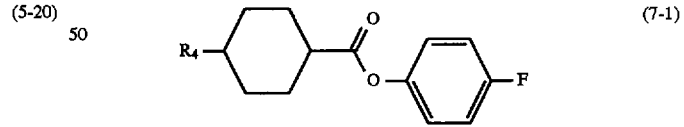 (7-1)
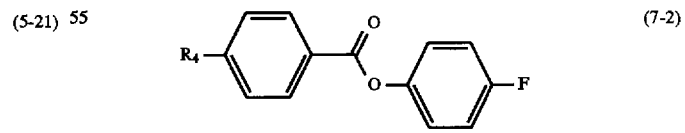 (7-2)
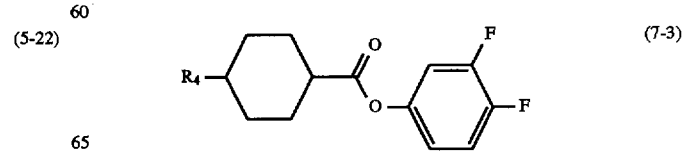 (7-3)

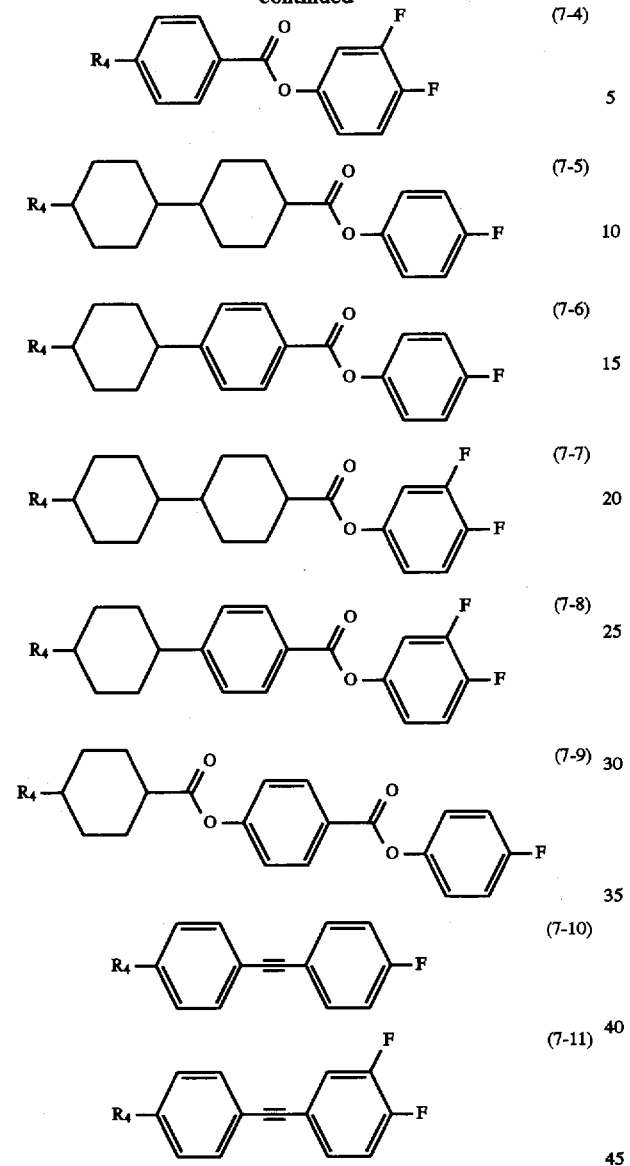

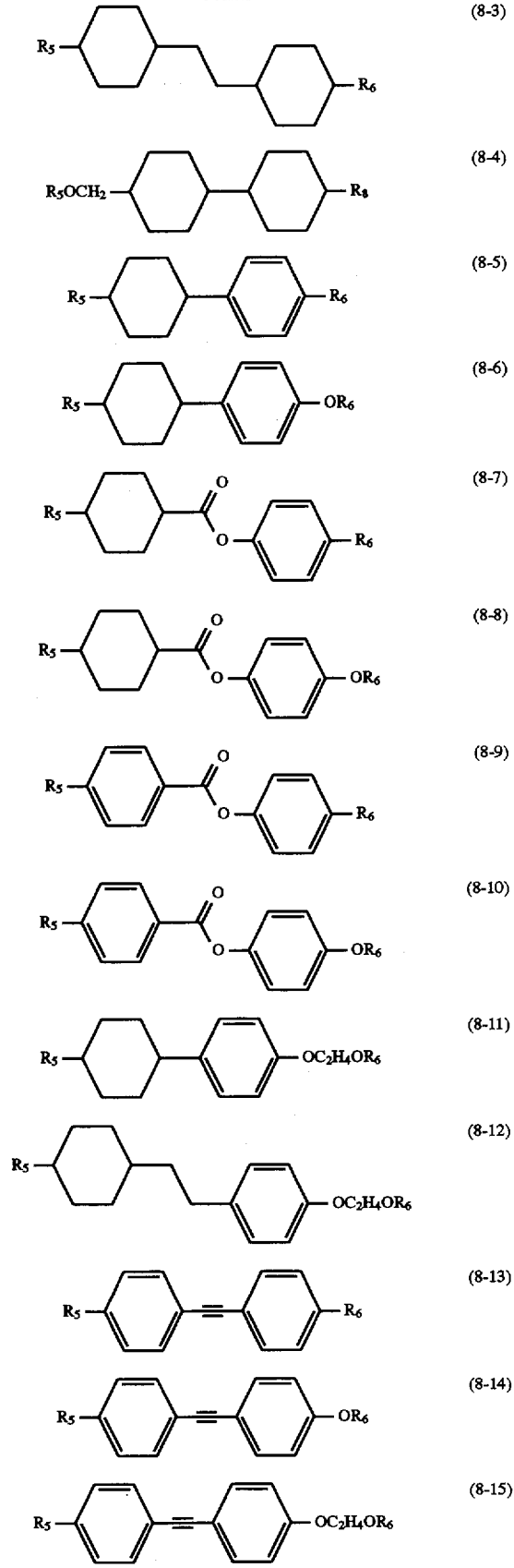

These compounds expressed by the formulas (5) to (7) have a positive dielectric anisotropy whose value is large, and are used as the composition component, particularly in order to reduce the threshold voltage. Further, they are used also for adjustment of the viscosity, adjustment of the optical anisotropy, broadening of the liquid crystal phase temperature range, etc., and also for improvement of the steepness.

Further, among the compounds of the second B component, (8-1) to (8-15) and (9-1) to (9-14) are mentioned as preferable examples of compounds included in the formulas (8) and (9).

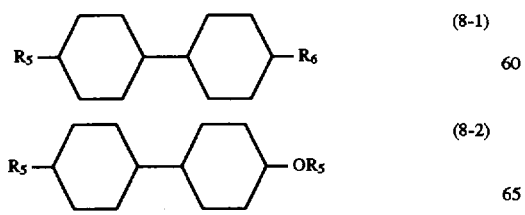

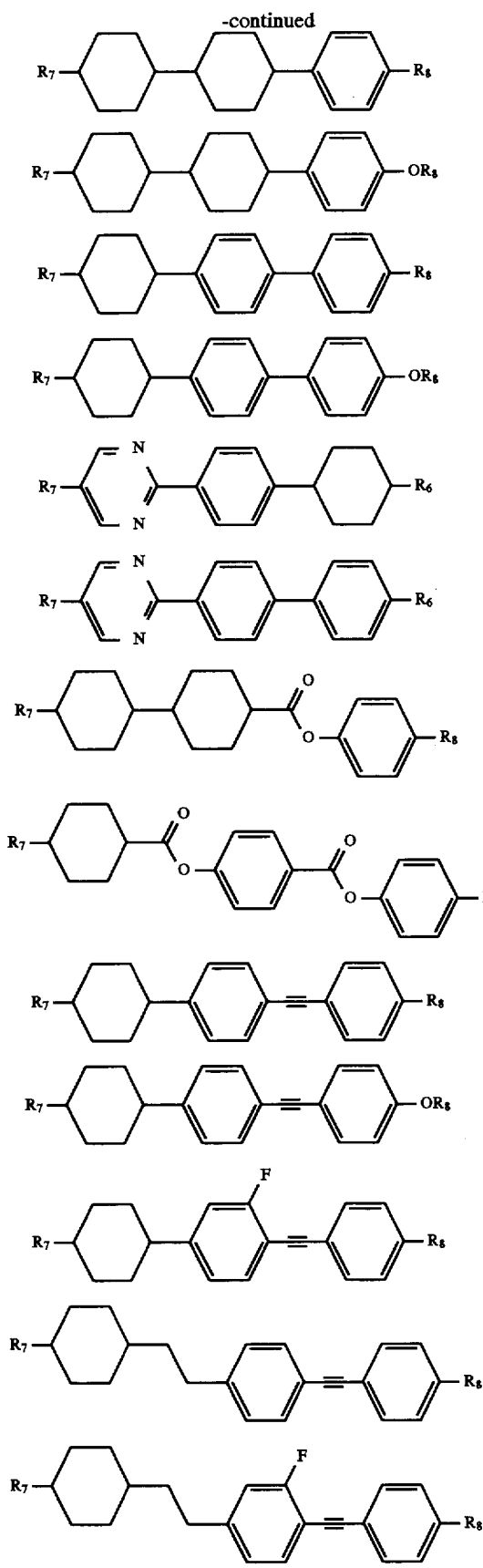

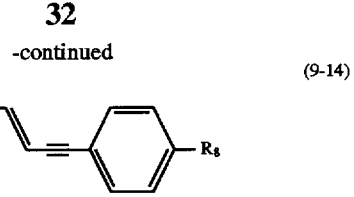

These compounds expressed by the formulas (8) and (9) have a negative or weakly positive dielectric anisotropy, and among these compounds, those expressed by the formula (8) are used as composition components, mainly for reducing the viscosity and adjusting the optical anisotropy and those expressed by the formula (9) are used thereas mainly for broadening the liquid crystal temperature range and/or for adjusting the optical anisotropy.

Compounds expressed by the formulas (5) to (9) are indispensable when liquid crystal compositions particularly for STN type display mode and for usual TN type display mode are prepared.

The quantity of the compounds used for preparing the liquid crystal compositions for usual STN type display mode and TN type display mode is suitably in the range of 1 to 99% by weight based upon the total weight of the liquid crystal compositions, preferably 10 to 97% by weight, more preferably 40 to 95% by weight.

The liquid crystal compositions provided according to the present invention are preferred to contain at least one kind of the liquid crystalline compounds expressed by the formula (1) in a proportion of 0.1 to 99% by weight, in order to exhibit superior characteristics. The liquid crystal compositions are generally prepared according to known process, for example a process of mutually dissolving various components at high temperatures. Further, if necessary, a suitable additive is added, whereby improvement according to aimed use applications is made to optimize the compositions. Such additives have been known to person of ordinary skill in the art and described in literatures in detail. Usually, there are added a chiral dopant or the like having an effect of inducing the helical structure of liquid crystals to adjust necessary twist angle and thereby prevent reverse twist.

Further, when a dichroic pigment such as those of merocyanine group, styryl group, azo group, azoxy group, quinophthalone group, anthraquinone group, tetrazine group, etc. is added, the resulting compositions can also be used as those for GH type mode. The compositions according to the present invention can be used not only for NCAP prepared by micro-encapsulating nematic liquid crystals, polymer-dispersed type liquid crystal display element (PDLCD) such as polymer network liquid crystal display element (PNLCD), but also as liquid crystal compositions of birefringence adjusted (ECB) type and DS type.

As examples of the liquid crystal compositions containing the compounds of the present invention, the following compositions can be mentioned, and in addition, Nos. of the compounds are the same as those shown in the Examples mentioned later:

COMPOSITION EXAMPLE 1

(E)-(trans-4-(trans-4-(4-fluorobutenyl)cyclohexyl)cyclohexyl)-4-fluorobenzene (No. 177) 5% by weight (E)-(2-(trans-4-(trans-4-(4-fluorobutenyl)cyclohexyl)cyclohexyl)ethyl)-3,4-difluorobenzene (No. 266) 5% by weight (E)-4-(trans-4-(4-fluorobutenyl)cyclohexyl)-3',4'-difluorobiphenyl (No. 76) 5% by weight (E)-(trans-4-(trans-4-(4-fluorobutenyl)cyclohexyl)cyclohexyl)-3,4-difluorobenzene (No. 176) 5% by weight (E)-(trans-4-(trans-4-(4-fluorobutenyl)cyclohexyl) cyclohexyl)-4-ethylbenzene (No. 204) 4% by weight (trans-4-(trans-4-ethylcyclohexyl)cyclohexyl)-3,4-difluorobenzene 9% by weight (trans-4-(trans-4-propylcyclohexyl)cyclohexyl)-3,4-difluorobenzene 9% by weight (trans-4-(trans-4-pentylcyclohexyl)cyclohexyl)-3,4-difluorobenzene 9% by weight 4-(trans-4-ethylcyclohexyl)-3',4'-difluorobiphenyl 4% by weight 4-(trans-4-propylcyclohexyl)-3',4'-difluorobiphenyl 4% by weight 4-(trans-4-pentylcyclohexyl)-3',4'-difluorobiphenyl 8% by weight (trans-4-(trans-4-propylcyclohexyl)cyclohexyl)-3,4,5-trifluorobenzene 7% by weight (trans-4-(trans-4-pentylcyclohexyl)cyclohexyl)-3,4,5-trifluorobenzene 3% by weight (2-(trans-4-(trans-4-propylcyclohexyl)cyclohexyl)-ethyl)-3,4,5-trifluorobenzene 5% by weight (2-(trans-4-(trans-4-pentylcyclohexyl)cyclohexyl)ethyl)-3,4,5-trifluorobenzene 5% by weight (trans-4-(2-trans-4-pentylcyclohexyl)ethyl)cyclohexyl)-3,4,5-trifluorobenzene 5% by weight trans-4-propylcyclohexyl-4-ethoxybenzene 4% by weight (trans-4-(trans-4-propylcyclohexyl)cyclohexyl)-4-methoxybenzene 4% by weight

COMPOSITION EXAMPLE 2

(E)-4-(trans-4-(4-fluorobutenyl)cyclohexyl)-4'-fluorobiphenyl (No. 73) 4% by weight (E)-(trans-4-(trans-4-(4-fluorobutenyl)cyclohexyl) cyclohexyl)-3-fluoro-chlorobenzene (No. 179) 5% by weight (E)-(2-(trans-4-(trans-4-(4-fluorobutenyl)cyclohexyl) cyclohexyl)ethyl-3-fluoro-4-chlorobenzene (No. 267) 5% by weight (E)-(trans-4-(4-fluorobutenyl)cyclohexyl)-4-fluorobenzene (No. 2) 6% by weight (E)-(trans-4-(trans-4-(4-fluorobutenyl)cyclohexyl) cyclohexyl)-3,4,5-trifluorobenzene (No. 180) 5% by weight trans-4-heptylcyclohexyl-3,4-difluorobenzene 4% by weight (2-(trans-4-pentylcyclohexyl)ethyl)-3,4-difluorobenzene 6% by weight (trans-4-(trans-4-ethylcyclohexyl)cyclohexyl)-3,4-difluorobenzene 5% by weight (trans-4-(trans-4-propylcyclohexyl)cyclohexyl)-3,4-difluorobenzene 5% by weight (trans-4-(trans-4-pentylcyclohexyl)cyclohexyl)-3,4-difluorobenzene 5% by weight (trans-4-(2-(trans-4-ethylcyclohexyl)ethyl)cyclohexyl)-3,4-difluorobenzene 4% by weight (trans-4-(2-(trans-4-propylcyclohexyl)ethyl)cyclohexyl)-3,4-difluorobenzene 2% by weight (trans-4-(2-(trans-4-pentylcyclohexyl)ethyl)cyclohexyl)-3,4-difluorobenzene 4% by weight 4-(trans-4-ethylcyclohexyl)-3',4'-difluorobiphenyl 5% by weight 4-(trans-4-propylcyclohexyl)-3',4'-difluorobiphenyl 5% by weight 4-(trans-4-pentylcyclohexyl)-3',4'-difluorobiphenyl 10% by weight 4-(trans-4-ethylcyclohexyl)-4'-fluorobiphenyl 4% by weight 4-(trans-4-propylcyclohexyl)-4'-fluorobiphenyl 4% by weight 4-(trans-4-pentylcyclohexyl)-4'-fluorobiphenyl 2% by weight (trans-4-(trans-4-propylcyclohexyl)cyclohexyl)-4-fluorobenzene 4% by weight (trans-4-(trans-4-propylcyclohexyl)cyclohexyl)-4-methylbenzene 6% by weight

COMPOSITION EXAMPLE 3

(E)-4-(trans-4-(4-fluorobutenyl)cyclohexyl)-3',4',5'-trifluorobiphenyl (No. 81) 5% by weight (E)-4-(trans-4-(4-fluorobutenyl)cyclohexyl)-3'-fluoro-4'-chlorobiphenyl (No. 77) 4% by weight (E)-(trans-4-(trans-4-(4-fluorobutenyl)cyclohexyl) cyclohexyl)-3-fluoro-4-trifluoromethylbenzene (No. 138) 4% by weight (E)-(trans-4-(trans-4-(4-fluorobutenyl)cyclohexyl) cyclohexyl)-3,5-difluoro-4-chlorobenzene (No. 181) 4% by weight (trans-4-propylcyclohexyl)-4-chlorobenzene 5% by weight (trans-4-pentylcyclohexyl)-4-chlorobenzene 5% by weight (trans-4-heptylcyclohexyl)-4-chlorobenzene 5% by weight 4-(trans-4-ethylcyclohexyl)-3',4'-difluorobiphenyl 8% by weight 4-(trans-4-propylcyclohexyl)-3',4'-difluorobiphenyl 8% by weight 4-(trans-4-pentylcyclohexyl)-3',4'-difluorobiphenyl 8% by weight (trans-4-(trans-4-ethylcyclohexyl)cyclohexyl)-4-chlorobenzene 5% by weight (trans-4-(trans-4-propylcyclohexyl)cyclohexyl)-4-chlorobenzene 8% by weight (trans-4-(trans-4-pentylcyclohexyl)cyclohexyl)-4-chlorobenzene 7% by weight 4-(trans-4-propylcyclohexyl)-3',4',5'-trifluorobiphenyl 6% by weight 4-(trans-4-pentylcyclohexyl)-3',4',5'-trifluorobiphenyl 6% by weight 2-fluoro-4-(trans-4-propylcyclohexyl)-4'-ethyltolan 4% by weight (trans-4-(2-(trans-4-propylcyclohexyl)ethyl)cyclohexyl)-3-fluoro-4-chlorobenzene 7% by weight

COMPOSITION EXAMPLE 4

(E)-(trans-4-(trans-4-(4-fluorobutenyl)cyclohexyl) cyclohexyl-4-trifluoromethoxybenzene (No. 141) 3% by weight (E)-(2-trans-4-(trans-4-(4-fluorobutenyl)cyclohexyl) cyclohexyl)ethyl)-3-fluoro-4-trifluoromethylbenzene (No. 270) 3% by weight (E)-4-(trans-4-(4-fluorobutenyl)cyclohexyl)-3'-fluoro-4'-trifluoromethoxybiphenyl (No. 80) 4% by weight (E)-(trans-4-(trans-4-(4-fluorobutenyl)cyclohexyl) cyclohexyl)-3,5-difluoro-4-trifluoromethylbenzene (No. 145) 4% by weight 4-(trans-4-ethylcyclohexyl)-3',4'-difluorobiphenyl 5% by weight 4-(trans-4-propylcyclohexyl)-3',4'-difluorobiphenyl 5% by weight 4-(trans-4-pentylcyclohexyl)-3',4'-difluorobiphenyl 5% by weight 4-(trans-4-ethylcyclohexyl)-4'-fluorobiphenyl 4% by weight 4-(trans-4-propylcyclohexyl)-4'-fluorobiphenyl 4% by weight (trans-4-(2-(trans-4-propylcyclohexyl)ethyl)cyclohexyl)-3,4,5-trifluorobenzene 5% by weight (trans-4-(2-(trans-4-butylcyclohexyl)ethyl)cyclohexyl)-3,4,5-trifluorobenzene 5% by weight (trans-4-(2-(trans-4-pentylcyclohexyl)ethyl)cyclohexyl)-3,4,5-trifluorobenzene 5% by weight (trans-4-(trans-4-propylcyclohexyl)cyclohexyl)-3,4,5-trifluorobenzene 4% by weight (trans-4-(trans-4-butylcyclohexyl)cyclohexyl)-3,4,5-trifluorobenzene 4% by weight (2-(trans-4-(trans-4-propylcyclohexyl)cyclohexyl)ethyl)-3,4,5-trifluorobenzene 6% by weight (2-(trans-4-(trans-4-pentylcyclohexyl)cyclohexyl)ethyl)-3,4,5-trifluorobenzene 6% by weight 4-(trans-4-propylcyclohexyl)-3',4',5'-trifluorobiphenyl 5% by weight 4-(trans-4-pentylcyclohexyl)-3',4',5'-trifluorobiphenyl 5% by weight (trans-4-(trans-4-propylcyclohexyl)cyclohexyl)-4-chlorobenzene 4% by weight (trans-4-(trans-4-pentylcyclohexyl)cyclohexyl)-4-chlorobenzene 4% by weight

COMPOSITION EXAMPLE 5

(E)-4-(trans-4-(4-fluorobutenyl)cyclohexyl)-4'-chlorobiphenyl (No. 72) 4% by weight (E)-(2-(trans-4-(trans-4-(4-fluorobutenyl)cyclohexyl)cyclohexyl)ethyl)-3,4,5-trifluorobenzene (No. 272) 6% by weight (E)-4-(trans-4-(4-fluorobutenyl)cyclohexyl)-3',5'-difluoro-4'-chlorobiphenyl (No. 82) 5% by weight (E)-(2-(trans-4-(trans-4-(4-fluorobutenyl)cyclohexyl)cyclohexyl)ethyl-4-fluorobenzene (No. 261) 5% by weight trans-4-heptylcyclohexyl-3,4,5-trifluorobenzene 5% by weight (trans-4-(trans-4-ethylcyclohexyl)cyclohexyl)-3,4-difluorobenzene 10% by weight (trans-4-(trans-4-propylcyclohexyl)cyclohexyl)-3,4-difluorobenzene 10% by weight (trans-4-(trans-4-pentylcyclohexyl)cyclohexyl)-3,4-difluorobenzene 10% by weight (trans-4-(2-(trans-4-ethylcyclohexyl)ethyl)cyclohexyl)-3,4-difluorobenzene 6% by weight (trans-4-(2-(trans-4-propylcyclohexyl)ethyl)cyclohexyl)-3,4-difluorobenzene 3% by weight (trans-4-(2-(trans-4-pentylcyclohexyl)ethyl)cyclohexyl)-3,4-difluorobenzene 6% by weight (trans-4-(trans-4-propylcyclohexyl)cyclohexyl)-4-fluorobenzene 4% by weight (trans-4-(trans-4-ethylcyclohexyl)cyclohexyl)-3,4,5-trifluorobenzene 5% by weight (trans-4-(trans-4-propylcyclohexyl)cyclohexyl)-3,4,5-trifluorobenzene 5% by weight 4-fluorophenyl-trans-4-(trans-4-propylcyclohexyl)cyclohexanecarboxylate 4% by weight 4-fluorophenyl-trans-4-(trans-4-pentylcyclohexyl)cyclohexanecarboxylate 4% by weight (trans-4-(trans-4-propylcyclohexyl)cyclohexyl)-4-methylbenzene 4% by weight (trans-4-(trans-4-propylcyclohexyl)cyclohexyl)-4-methoxybenzene 4% by weight

COMPOSITION EXAMPLE 6

(E)-(2-(trans-4-(trans-4-(4-fluorobutenyl)cyclohexyl)cyclohexyl)ethyl)-3,5-difluoro-4-chlorobenzene (No. 273) 5% by weight (E)-(2-(trans-4-(trans-4-(4-fluorobutenyl)cyclohexyl)cyclohexyl)ethyl)-3,5-difluoro-4-trifluoromethylbenzene (No. 276) 5% by weight (E)-(trans-4-(4-fluorobutenyl)cyclohexyl)-3-fluoro-4-trifluoromethoxybenzene (No. 16) 5% by weight (E)-4-(trans-4-(4-fluorobutenyl)cyclohexyl)-3',5'-difluoro-4'-trifluoromethylbiphenyl (No. 84) 5% by weight trans-4-heptylcyclohexyl-3,4,5-trifluorobenzene 8% by weight (trans-4-(2-(trans-4-propylcyclohexyl)ethyl)cyclohexyl)-3,4,5-trifluorobenzene 9% by weight (trans-4-(2-(trans-4-butylcyclohexyl)ethyl)cyclohexyl)-3,4,5-trifluorobenzene 9% by weight (trans-4-(2-(trans-4-pentylcyclohexyl)ethyl)cyclohexyl)-3,4,5-trifluorobenzene 9% by weight (trans-4-(trans-4-propylcyclohexyl)cyclohexyl)-3,4,5-trifluorobenzene 9% by weight (trans-4-(trans-4-butylcyclohexyl)cyclohexyl)-3,4,5-trifluorobenzene 5% by weight (2-(trans-4-(trans-4-propylcyclohexyl)cyclohexyl)ethyl)-3,4,5-trifluorobenzene 8% by weight (2-(trans-4-(trans-4-pentylcyclohexyl)cyclohexyl)ethyl)-3,4,5-trifluorobenzene 7% by weight 4-(trans-4-propylcyclohexyl)-3',4',5'-trifluorobiphenyl 8% by weight 2-(trans-4-pentylcyclohexyl)-3',4',5'-trifluorobiphenyl 8% by weight

COMPOSITION EXAMPLE 7

(E)-4-(trans-4-(4-fluorobutenyl)cyclohexyl)benzonitrile (No. 1) 7% by weight (E)-4-(2-trans-4-(5-fluoropentenyl)cyclohexyl)ethyl)-benzonitrile (No. 245) 7% by weight (E)-4-(trans-4-(4-fluorobutenyl)cyclohexyl)-4'-ethylbiphenyl (No. 36) 7% by weight (E)-(trans-4-(4-fluorobutenyl)cyclohexyl)-4-ethylbenzene (No. 9) 6% by weight 3-fluoro-4-cyanophenyl-4-propoxymethylbenzoate 5% by weight 4-(trans-4-ethylcyclohexyl)benzonitrile 5% by weight 4-(trans-4-propylcyclohexyl)benzonitrile 10% by weight trans,trans-4-propyl-4'-butylbicyclohexane 7% by weight trans,trans-4-propyl-4'-pentylbicyclohexane 3% by weight 4-ethyl-4'-methoxytolan 3% by weight 4-propyl-4'-methoxytolan 3% by weight
4-butyl-4'-methoxytolan 3% by weight
4-butyl-4'-ethoxytolan 3% by weight
4-pentyl-4'-methoxytolan 3% by weight
4-(trans-4-(trans-4-ethylcyclohexyl)cyclohexyl)benzonitrile 5% by weight
4-(trans-4-(trans-4-propylcyclohexyl)cyclohexyl)benzonitrile 5% by weight
4-(trans-4-(trans-4-butylcyclohexyl)cyclohexyl)benzonitrile 5% by weight
2-(4'-fluorobiphenyl-4-yl)-5-propylpyrimidine 5% by weight
(trans-4-(trans-4-propylcyclohexyl)cyclohexyl)-4-methylbenzene 5% by weight
(trans-4-(trans-4-propylcyclohexyl)cyclohexyl)-4-methoxybenzene 3% by weight

COMPOSITION EXAMPLE 8

(E)-4-(trans-4-(5-fluoropentenyl)cyclohexyl)benzonitrile (No. 19) 5% by weight
(E)-4-(2-(trans-4-(trans-4-(4-fluorobutenyl)cyclohexyl)cyclohexyl)ethyl)benzonitrile (No. 260) 5% by weight
(E)-trans-(trans-4-(4-fluorobutenyl)cyclohexyl)-4-ethylcyclohexane (No. 375) 4% by weight
(E)-4-(trans-4-(3-butenyl)cyclohexyl)benzonitrile 10% by weight
(E)-4-(trans-4-(3-pentenyl)cyclohexyl)benzonitrile 10% by weight
4-(trans-4-propylcyclohexyl)benzonitrile 7% by weight
trans,trans-4-methoxymethyl-4'-propylcyclohexane 5% by weight
trans,trans-4-propyl-4'-butylbicyclohexane 8% by weight
4-ethyl-4'-methyltolan 4% by weight
4-methyl-4'-hexyltolan 8% by weight
4,4'-dibutyltolan 4% by weight
4-(trans-4-(trans-4-propylcyclohexyl)cyclohexyl)benzonitrile 5% by weight
2-(4-(trans-4-propylcyclohexyl)phenyl)-5-ethylpyrimidine 5% by weight
2-(4-(trans-4-propylcyclohexyl)phenyl)-5-propylpyrimidine 5% by weight
2-(4'-fluorobiphenyl-4-yl)-5-propylpyrimidine 7% by weight
(trans-4-(trans-4-propylcyclohexyl)cyclohexyl)-4-methylbenzene 4% by weight
2-(4'-propylbiphenylyl-4-yl)-5-butylpyrimidine 4% by weight

COMPOSITION EXAMPLE 9

(E)-(trans-4-(4-fluorobutenyl)cyclohexyl)-4-trifluoromethoxybenzene (No. 8) 4% by weight
(E)-4-(2-(trans-4-(4-fluorobutenyl)cyclohexyl)ethyl)benzonitrile (No. 232) 8% by weight
(E)-(trans-4-(trans-4-(4-fluorobutenyl)cyclohexyl)cyclohexyl) (No. 205) 4% by weight
4-ethyl-4'-cyanobiphenyl 7% by weight
4-(4-fluorophenyl)-5-pentylpyrimidine 4% by weight
4-(trans-4-methoxymethylcyclohexyl)benzonitrile 10% by weight
4-(trans-4-ethoxymethylcyclohexyl)benzonitrile 8% by weight
4-cyanophenyl-4-ethylbenzoate 5% by weight
2-(4-ethylphenyl)-5-ethylpyrimidine 3% by weight
2-(4-ethylphenyl)-5-propylpyrimidine 3% by weight
2-(4-ethylphenyl)-5-butylpyrimidine 3% by weight
(trans-4-(trans-4-ethylcyclohexyl)cyclohexyl)-4-methylbenzene 4% by weight
(trans-4-(trans-4-propylcyclohexyl)cyclohexyl)-4-methylbenzene 5% by weight
(trans-4-(trans-4-propylcyclohexyl)cyclohexyl)-4-propylbenzene 8% by weight
2-(4-(trans-4-propylcyclohexyl)phenyl)-5-ethylpyrimidine 5% by weight
2-(4-(trans-4-propylcyclohexyl)phenyl)-5-propylpyrimidine 5% by weight
2-(4-(trans-4-propylcyclohexyl)phenyl)-5-butylpyrimidine 5% by weight
2-(4'-fluorobiphenyl-4-yl)-5-propylpyrimidine 5% by weight
2-(4-ethoxyphenyl)-5-propylpyrimidine 4% by weight

COMPOSITION EXAMPLE 10

(E)-4-(trans-4-(trans-4-(5-fluoropentenyl)cyclohexyl)cyclohexyl)benzonitrile (No. 120) 6% by weight
(E)-4-(trans-4-(5-fluoropentenyl)cyclohexyl)-4'-cyanobiphenyl (No. 41) 7% by weight
(E)-trans-(trans-4-(4-fluorobutenyl)cyclohexyl)-4-propylcyclohexane (No. 376) 6% by weight
2-(3,4-difluorophenyl)-5-propylpyrimidine 8% by weight
2-(4-ethylphenyl)-5-ethylpyrimidine 5% by weight
2-(4-ethylphenyl)-5-propylpyrimidine 5% by weight
2-(4-ethylphenyl)-5-butylpyrimidine 5% by weight
4-butoxyphenyl-trans-4-propylcyclohexanecarboxylate 6% by weight
4-ethoxyphenyl-trans-4-butylcyclohexanecarboxylate 6% by weight
4-methoxyphenyl-trans-4-pentylcyclohexanecarboxylate 4% by weight
2-(4'-fluorobiphenyl-4-yl)-5-propylpyrimidine 5% by weight
2-(4'-fluorobiphenyl-4-yl)-5-butylpyrimidine 5% by weight
2-(4'-fluorobiphenyl-4-yl)-5-pentylpyrimidine 5% by weight
4-(2-(trans-4-ethylcyclohexyl)ethyl)-4'-butyltolan 4% by weight
4-(2-(trans-4-propylcyclohexyl)ethyl)-4'-butyltolan 4% by weight
(trans-4-(trans-4-propylcyclohexyl)cyclohexyl)-4-methylbenzene 5% by weight
(trans-4-(trans-4-propylcyclohexyl)cyclohexyl)-4-propylbenzene 5% by weight
4'-cyanobiphenyl-4-yl-trans-4-(trans-4-propylcyclohexyl)cyclohexanecarboxylate 3% by weight
4'-cyanobiphenyl-4-yl-trans-4-(trans-4-pentylcyclohexyl)cyclohexanecarboxylate 3% by weight
4'-cyanobiphenyl-4-yl-4-(trans-4-propylcyclohexyl)benzoate 3% by weight

COMPOSITION EXAMPLE 11

(E)-4-(trans-4-(4-fluorobutenyl)cyclohexyl)benzonitrile (No. 1) 5% by weight (E)-4-(2-(trans-4-(trans-4-(5-fluoropentenyl)cyclohexyl)
cyclohexyl)ethyl)benzonitrile (No. 282) 5% by weight (E)-trans-(2-(trans-4-(5-fluoropentenyl)cyclohexyl)ethyl)
-4-propylcyclohexane (No. 396) 5% by weight (E)-(trans-4-(trans-4-(4-fluorobutenyl)cyclohexyl)
cyclohexyl)-4-propylbenzene (No. 205) 5% by weight 3-fluoro-4-cyanophenyl-4-ethoxymethylbenzoate 4% by weight 3-fluoro-4-cyanophenyl-4-propoxymethylbenzoate 11% by weight 4-(trans-4-ethylcyclohexyl)-2-fluorobenzonitrile 7% by weight 4-(trans-4-propylcyclohexyl)-2-fluorobenzonitrile 8% by weight (trans-4-(trans-4-ethylcyclohexyl)cyclohexyl)-3,4-difluorobenzene 5% by weight (trans-4-(trans-4-propylcyclohexyl)cyclohexyl)-3,4-difluorobenzene 5% by weight (trans-4-(trans-4-pentylcyclohexyl)cyclohexyl)-3,4-difluorobenzene 5% by weight 4-(trans-4-(trans-4-propylcyclohexyl)cyclohexyl)-2-fluorobenzonitrile 4% by weight (trans-4-(trans-4-propylcyclohexyl)cyclohexyl)-4-propylbenzene 4% by weight (trans-4-(trans-4-propylcyclohexyl)cyclohexyl)-4-methylbenzene 5% by weight (trans-4-(trans-4-propylcyclohexyl)cyclohexyl)-4-methoxybenzene 4% by weight 4-(2-(trans-4-propylcyclohexyl)ethyl)-4'-ethyltolan 3% by weight 4-(2-(trans-4-propylcyclohexyl)ethyl)-4'-propyltolan 3% by weight 4-(2-(trans-4-propylcyclohexyl)ethyl)-4'-butyltolan 3% by weight 2-fluoro-4-(trans-4-propylcyclohexyl)-4'-ethyltolan 3% by weight 2-fluoro-4-(trans-4-propylcyclohexyl)-4'-propyltolan 3% by weight 2-fluoro-4-(trans-4-propylcyclohexyl)-4'-butyltolan 3% by weight

COMPOSITION EXAMPLE 12

(E)-4-(trans-4-(5-fluoropentenyl)cyclohexyl)benzonitrile (No. 19) 4% by weight (E)-4-(trans-4-(trans-4-(4-fluorobutenyl)cyclohexyl)cyclohexyl)benzonitrile (No. 117) 4% by weight (E)-4-(trans-4-(4-fluorobutenyl)cyclohexyl)-4'-propylbiphenyl (No. 37) 3% by weight (E)-trans-(trans-4-(4-fluorobutenyl)cyclohexyl)-4-propylcyclohexane (No. 376) 3% by weight (E)-(trans-4-(4-fluorobutenyl)cyclohexyl)-4-fluorobenzene (No. 2) 4% by weight (E)-4-(trans-4-(3-butenyl)cyclohexyl)benzonitrile 9% by weight (E)-4-(trans-4-(3-pentenyl)cyclohexyl)benzonitrile 9% by weight 4-(trans-4-propylcyclohexyl)benzonitrile 13% by weight 4-(trans-4-pentylcyclohexyl)benzonitrile 7% by weight 4-(trans-4-methoxymethylcyclohexyl)benzonitrile 5% by weight 4-(trans-4-ethoxymethylcyclohexyl)benzonitrile 5% by weight 4-ethyl-4'-methoxytolan 5% by weight trans,trans-4-propyl-4'-butylbicyclohexane 4% by weight (trans-4-(trans-4-propylcyclohexyl)cyclohexyl)-4-fluorobenzene 4% by weight (trans-4-(trans-4-propylcyclohexyl)cyclohexyl)-4-methoxybenzene 4% by weight (trans-4-(trans-4-propylcyclohexyl)cyclohexyl)-4-methylbenzene 5% by weight (trans-4-(trans-4-propylcyclohexyl)cyclohexyl)-4-propylbenzene 8% by weight 2-fluoro-4-(trans-4-propylcyclohexyl)-4'-ethyltolan 4% by weight

COMPOSITION EXAMPLE 13

(E)-4-(trans-4-(4-fluorobutenyl)cyclohexyl)benzonitrile (No. 1) 4% by weight (E)-4-(trans-4-(4-fluorobutenyl)cyclohexyl)-4'-cyanobiphenyl (No. 35) 4% by weight (E)-trans-(trans-4-(trans-4-(4-fluorobutenyl)cyclohexyl)cyclohexyl)-4-propylcyclohexane (No. 408) 4% by weight 3-fluoro-4-cyanophenyl-4-ethoxymethylbenzoate 3% by weight 3-fluoro-4-cyanophenyl-4-propoxymethylbenzoate 8% by weight 3-fluoro-4-cyanophenyl-4-butoxymethylbenzoate 5% by weight methyl-trans-4-(trans-4-propylcyclohexyl)cyclohexanecarboxylate 7% by weight trans-4-propylcyclohexyl-4-ethoxybenzene 10% by weight 4-butoxyphenyl-trans-4-propylcyclohexanecarboxylate 4% by weight 4-propylphenyl-trans-4-butylcyclohexanecarboxylate 4% by weight 4-butylphenyl-trans-4-butylcyclohexanecarboxylate 4% by weight 2-(4-(trans-4-propylcyclohexyl)phenyl)-5-ethylpyrimidine 4% by weight 2-(4-(trans-4-propylcyclohexyl)phenyl)-5-propylpyrimidine 4% by weight 2-(4-(trans-4-propylcyclohexyl)phenyl)-5-butylpyrimidine 4% by weight (trans-4-(trans-4-ethylcyclohexyl)cyclohexyl)-3,4-difluorobenzene 4% by weight (trans-4-(trans-4-propylcyclohexyl)cyclohexyl)-3,4-difluorobenzene 4% by weight (trans-4-(trans-4-pentylcyclohexyl)cyclohexyl)-3,4-difluorobenzene 4% by weight (trans-4-(trans-4-propylcyclohexyl)cyclohexyl)-4-methylbenzene 5% by weight 4-fluorophenyl-trans-4-(trans-4-propylcyclohexyl)cyclohexanecarboxylate 5% by weight 4-fluorophenyl-trans-4-(trans-4-pentylcyclohexyl)cyclohexanecarboxylate 5% by weight 4-fluorophenyl-trans-4-propylcyclohexanecarboxylate 4% by weight

COMPOSITION EXAMPLE 14

(E)-4-(2-(trans-4-(4-fluorobutenyl)cyclohexyl)ethyl)benzonitrile (No. 232) 4% by weight (E)-4-(trans-4-(trans-4-(4-fluorobutenyl)cyclohexyl) cyclohexyl)benzonitrile (No. 117) 4% by weight (E)-(trans-4-(trans-4-(4-fluorobutenyl)cyclohexyl) cyclohexyl)-4-fluorobenzene (No. 177) 4% by weight (E)-trans-(trans-4-(4-fluorobutenyl)cyclohexyl)-4-ethylcyclohexane (No. 375) 5% by weight 2-(4-cyanophenyl)-5-propyldioxane 6% by weight 2-(4-cyanophenyl)-5-butyldioxane 6% by weight 4-(trans-4-methoxymethylcyclohexyl)benzonitrile 7% by weight 2-(4-ethylphenyl)-5-ethylpyrimidine 8% by weight 2-(4-ethylphenyl)-5-propylpyrimidine 8% by weight 2-(4-ethylphenyl)-5-butylpyrimidine 8% by weight trans,trans-4-methoxymethyl-4'-pentylbicyclohexane 7% by weight 2-(4-trans-4-propylcyclohexyl)phenyl)-5-ethylpyrimidine 6% by weight 2-(4-trans-4-propylcyclohexyl)phenyl)-5-propylpyrimidine 6% by weight 2-(4-trans-4-propylcyclohexyl)phenyl)-5-butylpyrimidine 6% by weight 2-fluoro-4-(trans-4-propylcyclohexyl)-4'-ethyltolan 5% by weight 2-fluoro-4-(trans-4-propylcyclohexyl)-4'-propyltolan 5% by weight 2-fluoro-4-(trans-4-propylcyclohexyl)-4'-butyltolan 5% by weight

COMPOSITION EXAMPLE 15

(E)-4-(trans-4-(4-fluorobutenyl)cyclohexyl)-4'-cyanobiphenyl (No. 35) 5% by weight (E)-(trans-(trans-4-(4-fluorobutenyl)cyclohexyl) cyclohexyl)-4-trifluoromethoxybenzene (No. 141) 5% by weight (E)-4-(trans-4-(4-fluorobutenyl)cyclohexyl)-4'-fluorobiphenyl (No. 73) 5% by weight (E)-(2-(trans-4-(5-fluoropentenyl)cyclohexyl)ethyl)-4-ethylbenzene (No. 249) 5% by weight 4-cyanophenyl-4-ethylbenzoate 6% by weight 4-ethyl-4'-cyanobiphenyl 12% by weight 4-(trans-4-propylcyclohexyl)benzonitrile 6% by weight 4-ethylphenyl-4-methoxybenzoate 6% by weight 4-butoxyphenyl-trans-4-propylcyclohexanecarboxylate 8% by weight 4-ethoxyphenyl-trans-4-butylcyclohexanecarboxylate 8% by weight 4-methoxyphenyl-trans-4-pentylcyclohexanecarboxylate 8% by weight 4-fluorophenyl-4-(trans-4-propylcyclohexyl)benzoate 6% by weight 4-fluorophenyl-trans-4-(trans-4-propylcyclohexyl)cyclohexanecarboxylate 5% by weight 4-fluorophenyl-trans-4-(trans-4-pentylcyclohexyl)cyclohexanecarboxylate 5% by weight 4-fluorophenyl-4-(trans-4-propylcyclohexylcarbonyloxy) benzoate 5% by weight 4-ethylphenyl-4-(trans-4-propylcyclohexylcarbonyloxy) benzoate 5% by weight

COMPOSITION EXAMPLE 16

(E)-4-(trans-4-(5-fluoropentenyl)cyclohexyl)benzonitrile (No. 19) 8% by weight (E)-3,5-difluoro-4-cyanophenyl-4-(3-pentenyl)benzoate 16% by weight 3-fluoro-4-cyanophenyl-4-ethoxymethylbenzoate 5% by weight 3-fluoro-4-cyanophenyl-4-propoxymethylbenzoate 13% by weight 4-(trans-4-propylcyclohexyl)-2-fluorobenzonitrile 11% by weight 4-(trans-4-propylcyclohexyl)benzonitrile 13% by weight 4-(trans-4-(trans-4-propylcyclohexyl)cyclohexyl)-2-fluorobenzonitrile 11% by weight 2-(4'-fluorobiphenyl-4-yl)-5-propylpyrimidine 8% by weight 2-(4'-fluorobiphenyl-4-yl)-5-butylpyrimidine 8% by weight 2-(4'-fluorobiphenyl-4-yl)-5-pentylpyrimidine 7% by weight

COMPOSITION EXAMPLE 17

(E)-(trans-4-(4-fluorobutenyl)cyclohexyl)-4-trifluoromethylbenzene (No. 7) 5% by weight (E)-(trans-4-(trans-4-(4-fluorobutenyl)cyclohexyl) cyclohexyl)-3,4-difluorobenzene (No. 176) 5% by weight (E)-4-(trans-4-(4-fluorobutenyl)cyclohexyl)-3'-fluoro-4'-trifluoromethoxybiphenyl (No. 80) 5% by weight trans,trans-4-propyl-4'-methoxybicyclohexane 4% by weight trans,trans-4-propyl-4'-propoxybicyclohexane 4% by weight trans,trans-4-pentyl-4'-methoxybicyclohexane 6% by weight trans-4-pentylcyclohexyl-4-fluorobenzene 6% by weight (trans-4-(trans-4-ethylcyclohexyl)cyclohexyl)-4-trifluoromethoxybenzene 4% by weight (trans-4-(trans-4-propylcyclohexyl)cyclohexyl)-4-trifluoromethoxybenzene 4% by weight (trans-4-(trans-4-butylcyclohexyl)cyclohexyl)-4-trifluoromethoxybenzene 6% by weight (trans-4-(trans-4-pentylcyclohexyl)cyclohexyl)-4-trifluoromethoxybenzene 6% by weight (2-(trans-4-(trans-4-propylcyclohexyl)cyclohexyl)ethyl)-3,4-fifluorobenzene 6% by weight (2-(trans-4-(trans-4-pentylcyclohexyl)cyclohexyl)ethyl)-3,4-difluorobenzene 6% by weight (trans-4-(trans-4-propylcyclohexyl)cyclohexyl)-3,5-difluoro-4-difluoromethoxybenzene 10% by weight 3,4-difluorophenyl-trans-4-(trans-4-propylcyclohexyl) cyclohexanecarboxylate 5% by weight 4-(trans-4-pentylcyclohexyl)-3',4'-difluorobiphenyl 3% by weight 4-(trans-4-pentylcyclohexyl)-3'-fluoro-4'-ethylbiphenyl 3% by weight (trans-4-(trans-4-propylcyclohexyl)cyclohexyl)-4-difluoromethoxybenzene 6% by weight (trans-4-(trans-4-pentylcyclohexyl)cyclohexyl)-4-difluoromethoxybenzene 6% by weight

COMPOSITION EXAMPLE 18

(E)-4-(trans-4-(4-fluorobutenyl)cyclohexyl)-3',4'-difluorobiphenyl (No. 76) 6% by weight (E)-(trans-4-(trans-4-(4-fluorobutenyl)cyclohexyl)cyclohexyl)-3,5-difluoro-4-trifluoromethylbenzene (No. 145) 6% by weight
(E)-4-(trans-4-(4-fluorobutenyl)cyclohexyl)-3',4',5'-trifluorobiphenyl (No. 81) 5% by weight
(trans-4-pentylcyclohexyl)-4-fluorobenzene 9% by weight
(trans-4-hexylcyclohexyl)-4-fluorobenzene 9% by weight
(trans-4-heptylcyclohexyl)-4-fluorobenzene 9% by weight
(trans-4-(trans-4-ethylcyclohexyl)cyclohexyl)-4-trifluoromethoxybenzene 6% by weight
(trans-4-(trans-4-propylcyclohexyl)cyclohexyl)-4-trifluoromethoxybenzene 6% by weight
(trans-4-(trans-4-butylcyclohexyl)cyclohexyl)-4-trifluoromethoxybenzene 6% by weight
(trans-4-(trans-4-pentylcyclohexyl)cyclohexyl)-4-trifluoromethoxybenzene 6% by weight
(2-(trans-4-(trans-4-propylcyclohexyl)cyclohexyl)ethyl)-4-trifluoromethoxybenzene 5% by weight
(2-(trans-4-(trans-4-pentylcyclohexyl)cyclohexyl)ethyl)-4-trifluoromethoxybenzene 5% by weight
4-(trans-4-propylcyclohexyl)-3',4'-difluorobiphenyl 8% by weight
4-(trans-4-pentylcyclohexyl)-3',4'-difluorobiphenyl 8% by weight
4,4'-bis(trans-4-propylcyclohexyl)-2-fluorobiphenyl 3% by weight
2-fluoro-4-(trans-4-pentylcyclohexyl)-4'-(trans-4-propylcyclohexyl)biphenyl 3% by weight

COMPOSITION EXAMPLE 19

(E)-4-(trans-4-(4-fluorobutenyl)cyclohexyl)benzonitrile (No. 1) 9% by weight
(E)-(trans-4-(trans-4-(4-fluorobutenyl)cyclohexyl)cyclohexyl)-4-propylbenzene (No. 205) 8% by weight
(E)-4-(trans-4-(4-fluorobutenyl)cyclohexyl)-4'-fluorobiphenyl (No. 73) 8% by weight
(E)-4-(trans-4-(2-propenyl)cyclohexyl)benzonitrile 3% by weight
4-butyl-4'-ethylbiphenyl 3% by weight
4-propyl-4'-cyanobiphenyl 5% by weight
4-pentyl-4'-cyanobiphenyl 5% by weight
4-(trans-4-ethylcyclohexyl)-2-fluorobenzonitrile 5% by weight
(2-(trans-4-propylcyclohexyl)ethyl)-4-ethoxybenzene 4% by weight
(2-(trans-4-pentylcyclohexyl)ethyl)-4-propoxybenzene 8% by weight
4-cyanophenyl-propylbenzoate 5% by weight
4-methoxyphenyl-trans-4-pentylcyclohexanecarboxylate 11% by weight
4-propoxyphenyl-trans-4-pentylcyclohexanecarboxylate 11% by weight
4"-pentyl-4-cyanoterphenyl 3% by weight
2-(4-cyanophenyl)-5-(4-butylphenyl)pyrimidine 3% by weight
2-(4-pentylphenyl)-5-(4-butylphenyl)pyrimidine 3% by weight
(2-(4-(trans-4-pentylcyclohexyl)phenyl)ethyl)-4-butylbenzene 3% by weight
(2-(4-(trans-4-pentylcyclohexyl)biphenyl)-4'-yl)ethyl)-4-propylbenzene 3% by weight

COMPOSITION EXAMPLE 20

(E)-4-(trans-4-(trans-4-(4-fluorobutenyl)cyclohexyl)cyclohexyl)benzonitrile (No. 117) 7% by weight
(E)-4-(trans-4-(4-fluorobutenyl)cyclohexyl)-4'-cyanobiphenyl (No. 35) 7% by weight
(E)-(trans-4-(4-fluorobutenyl)cyclohexyl)-4-propylbenzene (No. 10) 6% by weight
3,4-difluorophenyl-trans-4-butylcyclohexanecarboxylate 5% by weight
3,4-difluorophenyl-trans-4-pentylcyclohexanecarboxylate 5% by weight
3-fluoro-4-cyanophenyl-ethylbenzoate 4% by weight
3-fluoro-4-cyanophenyl-propylbenzoate 4% by weight
3-fluoro-4-cyanophenyl-butylbenzoate 6% by weight
3-fluoro-4-cyanophenyl-pentylbenzoate 6% by weight
4-(trans-4-methoxypropylcyclohexyl)-2-fluorobenzonitrile 10% by weight
3,4-difluorophenyl-trans-4-(trans-4-propylcyclohexyl)cyclohexanecarboxylate 4% by weight
3,4-difluorophenyl-trans-4-(trans-4-pentylcyclohexyl)cyclohexanecarboxylate 6% by weight
3-fluoro-4-cyanophenyl-4-(trans-4-ethylcyclohexyl)benzoate 4% by weight
3-fluoro-4-cyanophenyl-4-(trans-4-propylcyclohexyl)benzoate 4% by weight
3-fluoro-4-cyanophenyl-4-(trans-4-butylcyclohexyl)benzoate 6% by weight
3-fluoro-4-cyanophenyl-4-(trans-4-pentylcyclohexyl)benzoate 6% by weight
4-(trans-4-propylcyclohexyl)-4'-ethyltolan 10% by weight

COMPOSITION EXAMPLE 21

(E)-4-(trans-4-(4-fluorobutenyl)cyclohexyl)-4-fluorobiphenyl (No. 73) 6% by weight
(E)-4-(trans-4-(4-fluorobutenyl)cyclohexyl)-3',4'-difluorobiphenyl (No. 76) 6% by weight
(E)-4-(trans-4-(4-fluorobutenyl)cyclohexyl)-4'-ethylbiphenyl (No. 36) 5% by weight
(trans-4-(trans-4-ethylcyclohexyl)cyclohexyl)-3,4-difluorobenzene 10% by weight
(trans-4-(trans-4-propylcyclohexyl)cyclohexyl)-3,4-difluorobenzene 10% by weight
(trans-4-(trans-4-pentylcyclohexyl)cyclohexyl)-3,4-difluorobenzene 10% by weight
4-(trans-4-ethylcyclohexyl)-3',4'-difluorobiphenyl 5% by weight
4-(trans-4-propylcyclohexyl)-3',4'-difluorobiphenyl 5% by weight
4-(trans-4-pentylcyclohexyl)-3',4'-difluorobiphenyl 10% by weight
(trans-4-(trans-4-propylcyclohexyl)cyclohexyl)-3,4,5-trifluorobenzene 7% by weight
(trans-4-(trans-4-pentylcyclohexyl)cyclohexyl)-3,4,5-trifluorobenzene 3% by weight
(2-(trans-4-(trans-4-propylcyclohexyl)cyclohexyl)ethyl)-3,4,5-trifluorobenzene 5% by weight
(2-(trans-4-(trans-4-pentylcyclohexyl)cyclohexyl)ethyl)-3,4,5-trifluorobenzene 5% by weight (trans-4-(2-(trans-pentylcyclohexyl)ethyl)cyclohexyl)-3,4,5-trifluorobenzene 5% by weight trans-4-propylcyclohexyl-4-ethoxybenzene 4% by weight (trans-4-(trans-4-propylcyclohexyl)cyclohexyl)-4-methoxybenzene 4% by weight

COMPOSITION EXAMPLE 22

(E)-4-(trans-4-(4-fluorobutenyl)cyclohexyl)-4'-fluorobiphenyl (No. 73) 5% by weight (E)-4-(trans-4-(4-fluorobutenyl)cyclohexyl)-4'-chlorobiphenyl (No. 72) 5% by weight (E)-4-(trans-4-(4-fluorobutenyl)cyclohexyl)-4'-ethylbiphenyl (No. 36) 5% by weight (E)-4-(trans-4-(4-fluorobutenyl)cyclohexyl)-3',4'-difluorobiphenyl (No. 76) 5% by weight (E)-4-(trans-4-(4-fluorobutenyl)cyclohexyl)-4'-trifluoromethylbiphenyl (No. 78) 5% by weight trans-4-heptylcyclohexyl-3,4-difluorobenzene 4% by weight (2-(trans-4-pentylcyclohexyl)ethyl)-3,4-difluorobenzene 6% by weight (trans-4-(trans-4-ethylcyclohexyl)cyclohexyl)-3,4-difluorobenzene 5% by weight (trans-4-(trans-4-propylcyclohexyl)cyclohexyl)-3,4-difluorobenzene 5% by weight (trans-4-(trans-4-pentylcyclohexyl)cyclohexyl)-3,4-difluorobenzene 5% by weight (trans-4-(2-(trans-4-ethylcyclohexyl)ethyl)cyclohexyl)-3,4-difluorobenzene 4% by weight (trans-4-(2-(trans-4-propylcyclohexyl)ethyl)cyclohexyl)-3,4-difluorobenzene 2% by weight (trans-4-(2-trans-4-pentylcyclohexyl)ethyl)cyclohexyl)-3,4-difluorobenzene 4% by weight 4-(trans-4-ethylcyclohexyl)-3',4'-difluorobiphenyl 5% by weight 4-(trans-4-propylcyclohexyl)-3',4'-difluorobiphenyl 5% by weight 4-(trans-4-pentylcyclohexyl)-3',4'-difluorobiphenyl 10% by weight 4-(trans-4-ethylcyclohexyl)-4'-fluorobiphenyl 4% by weight 4-(trans-4-propylcyclohexyl)-4'-fluorobiphenyl 4% by weight 4-(trans-4-pentylcyclohexyl)-4'-fluorobiphenyl 2% by weight (trans-4-(trans-4-propylcyclohexyl)cyclohexyl)-4-fluorobenzene 4% by weight (trans-4-(trans-4-propylcyclohexyl)cyclohexyl)-4-methylbenzene 6% by weight

COMPOSITION EXAMPLE 23

(E)-4-(trans-4-(4-fluorobutenyl)cyclohexyl)-3',4'-difluorobiphenyl (No. 76) 5% by weight (E)-4-(trans-4-(4-fluorobutenyl)cyclohexyl)-4'-trifluoromethylbiphenyl (No. 78) 5% by weight (E)-4-(trans-4-(4-fluorobutenyl)cyclohexyl)-4'-chlorobiphenyl (No. 72) 8% by weight (trans-4-propylcyclohexyl)-4-chlorobenzene 5% by weight (trans-4-pentylcyclohexyl)-4-chlorobenzene 5% by weight (trans-4-heptylcyclohexyl)-4-chlorobenzene 5% by weight 4-(trans-4-ethylcyclohexyl)-3',4'-difluorobiphenyl 8% by weight 4-(trans-4-propylcyclohexyl)-3',4'-difluorobiphenyl 8% by weight 4-(trans-4-pentylcyclohexyl)-3',4'-difluorobiphenyl 8% by weight (trans-4-(trans-4-ehtylcyclohexyl)cyclohexyl)-4-chlorobenzene 5% by weight (trans-4-(trans-4-propylcyclohexyl)cyclohexyl)-4-chlorobenzene 8% by weight (trans-4-(trans-4-pentylcyclohexyl)cyclohexyl)-4-chlorobenzene 7% by weight 4-(trans-4-propylcyclohexyl)-3',4',5'-trifluorobiphenyl 6% by weight 4-(trans-4-pentylcyclohexyl)-3',4',5'-trifluorobiphenyl 6% by weight 2-fluoro-4-(trans-4-propylcyclohexyl)-4'-ethyltolan 4% by weight (trans-4-(2-(trans-4-propylcyclohexyl)ethyl)cyclohexyl)-3-fluoro-4-chlorobenzene 7% by weight

COMPOSITION EXAMPLE 24

(E)-4-(trans-4-(4-fluorobutenyl)cyclohexyl)-4'-chlorobiphenyl (No. 72) 4% by weight (E)-4-(trans-4-(4-fluorobutenyl)cyclohexyl)-3',4'-difluorobiphenyl (No. 76) 5% by weight (E)-4-(trans-4-(4-fluorobutenyl)cyclohexyl)-4'-fluorobiphenyl (No. 73) 5% by weight trans-4-heptylcyclohexyl-3,4,5-trifluorobenzene 5% by weight (trans-4-(trans-4-ethylcyclohexyl)cyclohexyl)-3,4-difluorobenzene 12% by weight (trans-4-(trans-4-propylcyclohexyl)cyclohexyl)-3,4-difluorobenzene 12% by weight (trans-4-(trans-4-pentylcyclohexyl)cyclohexyl)-3,4-difluorobenzene 12% by weight (trans-4-(2-(trans-4-ethylcyclohexyl)ethyl)cyclohexyl)-3,4-difluorobenzene 6% by weight (trans-4-(2-(trans-4-propylcyclohexyl)ethyl)cyclohexyl)-3,4-difluorobenzene 3% by weight (trans-4-(2-(trans-4-pentylcyclohexyl)ethyl)cyclohexyl)-3,4-difluorobenzene 6% by weight (trans-4-(trans-4-propylcyclohexyl)cyclohexyl)-4-fluorobenzene 4% by weight (trans-4-(trans-4-ethylcyclohexyl)cyclohexyl)-3,4,5-trifluorobenzene 5% by weight (trans-4-(trans-4-propylcyclohexyl)cyclohexyl)-3,4,5-trifluorobenzene 5% by weight 4-fluorophenyl-trans-4-(trans-4-propylcyclohexyl)cyclohexanecarboxylate 4% by weight 4-(fluorophenyl-trans-4-(trans-4-pentylcyclohexyl)cyclohexanecarboxylate 4% by weight (trans-4-(trans-4-propylcyclohexyl)cyclohexyl)-4-methylbenzene 4% by weight (trans-4-(trans-4-propylcyclohexyl)cyclohexyl)-4-methoxybenzene 4% by weight

COMPOSITION EXAMPLE 25

(E)-4-(trans-4-(4-fluorobutenyl)cyclohexyl)-4'-fluorobiphenyl (No. 73) 4% by weight (E)-4-(trans-4-(4-fluorobutenyl)cyclohexyl)-4'-chlorobiphenyl (No. 72) 4% by weight (E)-4-(trans-4-(4-fluorobutenyl)cyclohexyl)-4'-trifluoromethylbiphenyl (No. 78) 4% by weight trans-4-heptylcyclohexyl-3,4,5-trifluorobenzene 16% by weight (trans-4-(2-(trans-4-propylcyclohexyl)ethyl)cyclohexyl)-3,4,5-trifluorobenzene 9% by weight (trans-4-(2-(trans-4-butylcyclohexyl)ethyl)cyclohexyl)-3,4,5-trifluorobenzene 9% by weight (trans-4-(2-(trans-4-pentylcyclohexyl)ethyl)cyclohexyl)-3,4,5-trifluorobenzene 9% by weight (trans-4-(trans-4-propylcyclohexyl)cyclohexyl)-3,4,5-trifluorobenzene 9% by weight (trans-4-(trans-4-butylcyclohexyl)cyclohexyl)-3,4,5-trifluorobenzene 5% by weight (2-(trans-4-(trans-4-propylcyclohexyl)cyclohexyl)ethyl)-3,4,5-trifluorobenzene 8% by weight (2-(trans-4-(trans-4-pentylcyclohexyl)cyclohexyl)ethyl)-3,4,5-trifluorobenzene 7% by weight 4-(trans-4-propylcyclohexyl)-3',4',5'-trifluorobiphenyl 8% by weight 2-(trans-4-pentylcyclohexyl)-3',4',5'-trifluorobiphenyl 8% by weight

COMPOSITION EXAMPLE 26

(E)-4-(trans-4-(4-fluorobutenyl)cyclohexyl)benzonitrile (No. 1) 7% by weight (E)-4-(trans-4-(5-fluoropentenyl)cyclohexyl)benzonitrile (No. 19) 7% by weight (E)-4-(trans-4-(4-fluorobutenyl)cyclohexyl)-4'-ethylbiphenyl (No. 36) 7% by weight (E)-(trans-4-(4-fluorobutenyl)cyclohexyl)-4-(trans-4-propylcyclohexyl)benzene (No. 207) 6% by weight 3-fluoro-4-cyanophenyl-4-propoxymethylbenzoate 5% by weight 4-(trans-4-ethylcyclohexyl)benzonitrile 5% by weight 4-(trans-4-propylcyclohexyl)benzonitrile 10% by weight trans,trans-4-propyl-4'-butylcyclohexane 7% by weight trans,trans-4-propyl-4'-pentylcyclohexane 3% by weight 4-ethyl-4'-methoxytolan 3% by weight 4-propyl-4'-methoxytolan 3% by weight 4-butyl-4'-methoxytolan 3% by weight 4-butyl-4'-ethoxytolan 3% by weight 4-pentyl-4'-methoxytolan 3% by weight 4-(trans-4-(trans-4-ethylcyclohexyl)cyclohexyl)benzonitrile 5% by weight 4-(trans-4-(trans-4-propylcyclohexyl)cyclohexyl)benzonitrile 5% by weight 4-(trans-4-(trans-4-butylcyclohexyl)cyclohexyl)benzonitrile 5% by weight 2-(4'-fluorobiphenyl-4-yl)-5-propylpyridine 5% by weight (trans-4-(trans-4-propylcyclohexyl)cyclohexyl)-4-methylbenzene 5% by weight (trans-4-(trans-4-propylcyclohexyl)cyclohexyl)-4-methoxybenzene 3% by weight

COMPOSITION EXAMPLE 27

(E)-4-(trans-4-(5-fluoropentenyl)cyclohexyl)benzonitrile (No. 19) 5% by weight (E)-4-(2-(trans-4-(trans-4-(4-fluorobutenyl)cyclohexyl)cyclohexyl)ethyl)benzonitrile (No. 260) 5% by weight (E)-4-(trans-4-(5,5,5-trifluoropentenyl)cyclohexyl)benzonitrile (No. 312) 4% by weight (E)-4-(trans-4-(3-butenyl)cyclohexyl)benzonitrile 10% by weight (E)-4-(trans-4-(3-pentenyl)cyclohexyl)benzonitrile 10% by weight 4-(trans-4-propylcyclohexyl)benzonitrile 7% by weight trans,trans-4-methoxymethyl-4'-propylcyclohexane 5% by weight trans,trans-4-propyl-4'-butylbicyclohexane 8% by weight 4-ethyl-4'-methyltolan 4% by weight 4-methyl-4'-hexyltolan 8% by weight 4,4'-dibutyltolan 4% by weight 4-(trans-4-(trans-4-propylcyclohexyl)cyclohexyl)benzonitrile 5% by weight 2-(4-(trans-4-propylcyclohexyl)phenyl)-5-ethylpyrimidine 5% by weight 2-(4-(trans-4-propylcyclohexyl)phenyl)-5-propylpyrimidine 5% by weight 2-(4'-fluorobiphenyl-4-yl)-5-propylpyrimidine 7% by weight (trans-4-(trans-4-propylcyclohexyl)cyclohexyl)-4-methylbenzene 4% by weight 2-(4'-propylbiphenylyl-4-yl)-5-butylpyrimidine 4% by weight

COMPOSITION EXAMPLE 28

(E)-4-(trans-4-(4-fluorobutenyl)cyclohexyl)benzonitrile (No. 1) 8% by weight (E)-(trans-4-(4-fluorobutenyl)cyclohexyl)-4-(trans-4-propylcyclohexyl)benzene (No. 207) 4% by weight (E)-4-(trans-4-(4-fluorobutenyl)cyclohexyl)-4'-trifluoromethylbiphenyl (No. 78) 4% by weight 4-ethyl-4'-cyanobiphenyl 7% by weight 2-(4-fluorophenyl)-5-pentylpyrimidine 4% by weight 4-(trans-4-methoxymethylcyclohexyl)benzonitrile 10% by weight 4-(trans-4-ethoxymethylcyclohexyl)benzonitrile 8% by weight 4-cyanophenyl-4-ethylbenzoate 5% by weight 2-(4-ethylphenyl)-5-ethylpyrimidine 3% by weight 2-(4-ethylphenyl)-5-propylpyrimidine 3% by weight 2-(4-ethylphenyl)-5-butylpyrimidine 3% by weight (trans-4-(trans-4-ethylcyclohexyl)cyclohexyl)-4-methylbenzene 4% by weight (trans-4-(trans-4-propylcyclohexyl)cyclohexyl)-4-methylbenzene 5% by weight (trans-4-(trans-4-propylcyclohexyl)cyclohexyl)-4-propylbenzene 8% by weight 2-(4-(trans-4-propylcyclohexyl)phenyl)-5-ethylpyrimidine 5% by weight 2-(4-(trans-4-propylcyclohexyl)phenyl)-5-propylpyrimidine 5% by weight 2-(4-(trans-4-propylcyclohexyl)phenyl)-5-butylpyrimidine 5% by weight 2-(4'-fluorobiphenyl-4-yl)-5-propylpyrimidine 5% by weight 2-(4-ethoxyphenyl)-5-propylpyrimidine 4% by weight

COMPOSITION EXAMPLE 29

(E)-4-(trans-4-(trans-4-(4-fluorobutenyl)cyclohexyl)cyclohexyl)benzonitrile (No. 117) 6% by weight (E)-4-(trans-4-(5-fluoropentenyl)cyclohexyl)-4'-cyanobiphenyl (No. 41) 7% by weight (E)-4-(trans-4-(4-fluorobutenyl)cyclohexyl)-4'-ethylbiphenyl (No. 36) 6% by weight 2-(3,4-difluorophenyl)-5-propylpyrimidine 8% by weight 2-(4-ethylphenyl)-5-ethylpyrimidine 5% by weight 2-(4-ethylphenyl)-5-propylpyrimidine 5% by weight 2-(4-ethylphenyl)-5-butylpyrimidine 5% by weight 4-butoxyphenyl-trans-4-propylcyclohexanecarboxylate 6% by weight 4-ethoxyphenyl-trans-4-butylcyclohexanecarboxylate 6% by weight 4-methoxyphenyl-trans-4-pentylcyclohexanecarboxylate 4% by weight 2-(4'-fluorobiphenyl-4-yl)-5-propylpyrimidine 5% by weight 2-(4'-fluorobiphenyl-4-yl)-5-butylpyrimidine 5% by weight 2-(4'-fluorobiphenyl-4-yl)-5-pentylpyrimidine 5% by weight 4-(2-(trans-4-ethylcyclohexyl)ethyl)-4'-butyltolan 4% by weight 4-(2-(trans-4-propylcyclohexyl)ethyl)-4'-butyltolan 4% by weight (trans-4-(trans-4-propylcyclohexyl)cyclohexyl)-4-methylbenzene 5% by weight (trans-4-(trans-4-propylcyclohexyl)cyclohexyl)-4-propylbenzene 5% by weight 4'-cyanobiphenyl-4-yl-trans-4-(trans-4-propylcyclohexyl)cyclohexanecarboxylate 3% by weight 4'-cyanobiphenyl-4-yl-trans-4-(trans-4-pentylcyclohexyl)cyclohexanecarboxylate 3% by weight 4'-cyanobiphenyl-4-yl-4-(trans-4-propylcyclohexyl)benzoate 3% by weight

COMPOSITION EXAMPLE 30

(E)-4-(trans-4-(4-fluorobutenyl)cyclohexyl)benzonitrile (No. 1) 5% by weight (E)-4-(2-trans-4-(trans-4-(4-fluorobutenyl)cyclohexyl)cyclohexyl)ethyl)benzonitrile (No. 260) 5% by weight (E)-4-(trans-4-(4-fluorobutenyl)cyclohexyl)-4'-ethylbiphenyl (No. 36) 5% by weight (E)-(trans-4-(4-fluorobutenyl)cyclohexyl)-4-(trans-4-propylcyclohexyl)benzene (No. 207) 5% by weight 3-fluoro-4-cyanophenyl-4-ethoxymethylbenzoate 4% by weight 3-fluoro-4-cyanophenyl-4-propoxymethylbenzoate 11% by weight 4-(trans-4-ethylcyclohexyl)-2-fluorobenzonitrile 7% by weight 4-(trans-4-propylcyclohexyl)-2-fluorobenzonitrile 8% by weight (trans-4-(trans-4-ethylcyclohexyl)cyclohexyl)-3,4-difluorobenzene 5% by weight (trans-4-(trans-4-propylcyclohexyl)cyclohexyl)-3,4-difluorobenzene 5% by weight (trans-4-(trans-4-pentylcyclohexyl)cyclohexyl)-3,4-difluorobenzene 5% by weight 4-(trans-4-(trans-4-propylcyclohexyl)cyclohexyl)-2-fluorobenzonitrile 4% by weight (trans-4-(trans-4-propylcyclohexyl)cyclohexyl)-4-propylbenzene 4% by weight (trans-4-(trans-4-propylcyclohexyl)cyclohexyl)-4-methylbenzene 5% by weight (trans-4-(trans-4-propylcyclohexyl)cyclohexyl)-4-methoxybenzene 4% by weight 4-(2-trans-4-propylcyclohexyl)ethyl)-4'-ethyltolan 3% by weight 4-(2-(trans-4-propylcyclohexyl)ethyl)-4'-propyltolan 3% by weight 4-(2-(trans-4-propylcyclohexyl)ethyl)-4'-butyltolan 3% by weight 2-fluoro-4-(trans-4-propylcyclohexyl)-4'-ethyltolan 3% by weight 2-fluoro-4-(trans-4-propylcyclohexyl)-4'-propyltolan 3% by weight 2-fluoro-4-(trans-4-propylcyclohexyl)-4'-butyltolan 3% by weight

COMPOSITION EXAMPLE 31

(E)-4-(trans-4-(5-fluoropentenyl)cyclohexyl)benzonitrile (No. 19) 4% by weight (E)-4-(trans-4-(trans-4-(4-fluorobutenyl)cyclohexyl)cyclohexyl)benzonitrile (No. 117) 4% by weight (E)-4-(trans-4-(4-fluorobutenyl)cyclohexyl)-4'-propylbiphenyl (No. 37) 3% by weight (E)-(trans-4-(4-fluorobutenyl)cyclohexyl)-4-(trans-4-propylcyclohexyl)benzene (No. 207) 3% by weight (E)-4-(trans-4-(6-fluoro-3-hexenyl)cyclohexyl)benzonitrile (No. 29) 4% by weight (E)-4-(trans-4-(3-butenyl)cyclohexyl)benzonitrile 9% by weight (E)-4-(trans-4-(3-pentenyl)cyclohexyl)benzonitrile 9% by weight 4-(trans-4-propylcyclohexyl)benzonitrile 13% by weight 4-(trans-4-pentylcyclohexyl)benzonitrile 7% by weight 4-(trans-4-methoxymethylcyclohexyl)benzonitrile 5% by weight 4-(trans-4-ethoxymethylcyclohexyl)benzonitrile 5% by weight 4-ethyl-4'-methoxytolan 5% by weight trans,trans-4-propyl-4'-butylcyclohexane 4% by weight (trans-4-(trans-4-propylcyclohexyl)cyclohexyl)-4-fluorobenzene 4% by weight (trans-4-(trans-4-propylcyclohexyl)cyclohexyl)-4-methoxybenzene 4% by weight (trans-4-(trans-4-propylcyclohexyl)cyclohexyl)-4-methylbenzene 5% by weight (trans-4-(trans-4-propylcyclohexyl)cyclohexyl)-4-propylbenzene 8% by weight 2-fluoro-4-(trans-4-propylcyclohexyl)-4'-ethyltolan 4% by weight

COMPOSITION EXAMPLE 32

(E)-4-(trans-4-(4-fluorobutenyl)cyclohexyl)benzonitrile (No. 1) 5% by weight (E)-4-(trans-4-(4-fluorobutenyl)cyclohexyl)-4'-cyanobiphenyl (No. 35) 4% by weight (E)-4-(trans-4-(4-fluorobutenyl)cyclohexyl)-4'-(trans-4-butylcyclohexyl)biphenyl (No. 212) 3% by weight 3-fluoro-4-cyanophenyl-4-ethoxymethylbenzoate 3% by weight 3-fluoro-4-cyanophenyl-4-propoxymethylbenzoate 8% by weight 3-fluoro-4-cyanophenyl-4-butoxymethylbenzoate 5% by weight methyl-trans-4-(trans-4-propylcyclohexyl)cyclohexanecarboxylate 7% by weight trans-4-propylcyclohexyl-4-ethoxybenzene 10% by weight 4-butoxyphenyl-trans-4-propylcyclohexanecarboxylate 4% by weight 4-propylphenyl-trans-4-butylcyclohexanecarboxylate 4% by weight 4-butylphenyl-trans-4-butylcyclohexanecarboxylate 4% by weight 2-(4-(trans-4-propylcyclohexyl)phenyl)-5-ethylpyrimidine 4% by weight 2-(4-(trans-4-propylcyclohexyl)phenyl)-5-propylpyrimidine 4% by weight 2-(4-(trans-4-propylcyclohexyl)phenyl)-5-butylpyrimidine 4% by weight (trans-4-(trans-4-ethylcyclohexyl)cyclohexyl)-3,4-difluorobenzene 4% by weight (trans-4-(trans-4-propylcyclohexyl)cyclohexyl)-3,4-difluorobenzene 4% by weight (trans-4-(trans-4-pentylcyclohexyl)cyclohexyl)-3,4-difluorobenzene 4% by weight (trans-4-(trans-4-propylcyclohexyl)cyclohexyl)-4-methylbenzene 5% by weight 4-fluorophenyl-trans-4-(trans-4-propylcyclohexyl)cyclohexanecarboxylate 5% by weight 4-fluorophenyl-trans-4-(trans-4-pentylcyclohexyl)cyclohexanecarboxylate 5% by weight 4-fluorophenyl-trans-4-ethylcyclohexanecarboxylate 4% by weight

COMPOSITION EXAMPLE 33

(E)-4-(trans-4-(4-fluorobutenyl)cyclohexyl)benzonitrile (No. 1) 5% by weight (E)-4-(trans-4-(trans-4-(4-fluorobutenyl)cyclohexyl)cyclohexyl)benzonitrile (No. 117) 4% by weight (E)-4-(trans-4-(4-fluorobutenyl)cyclohexyl)-4'-fluorobiphenyl (No. 73) 4% by weight (E)-trans-(2-(trans-4-(4-fluorobutenyl)cyclohexyl)ethyl)-4-propylcyclohexane (No. 393) 4% by weight 2-(4-cyanophenyl)-5-propyldioxane 6% by weight 2-(4-cyanophenyl)-5-butyldioxane 6% by weight 4-(trans-4-methoxymethylcyclohexyl)benzonitrile 7% by weight 2-(4-ethylphenyl)-5-ethylpyrimidine 8% by weight 2-(4-ethylphenyl)-5-propylpyrimidine 8% by weight 2-(4-ethylphenyl)-5-butylpyrimidine 8% by weight trans,trans-4-methoxymethyl-4'-pentylbicyclohexane 7% by weight 2-(4-(trans-4-propylcyclohexyl)phenyl)-5-ethylpyrimidine 6% by weight 2-(4-(trans-4-propylcyclohexyl)phenyl)-5-propylpyrimidine 6% by weight 2-(4-(trans-4-propylcyclohexyl)phenyl)-5-butylpyrimdine 6% by weight 2-fluoro-4-(trans-4-propylcyclohexyl)-4'-ethyltolan 5% by weight 2-fluoro-4-(trans-4-propylcyclohexyl)-4'-propyltolan 5% by weight 2-fluoro-4-(trans-4-propylcyclohexyl)-4'-butyltolan 5% by weight

COMPOSITION EXAMPLE 34

(E)-4-(trans-4-(4-fluorobutenyl)cyclohexyl)-4'-cyanobiphenyl (No. 35) 5% by weight (E)-4-(trans-4-(4-fluorobutenyl)cyclohexyl)-4'-trifluoromethylbiphenyl (No. 78) 5% by weight (E)-4-(trans-4-(4-fluorobiphenyl)cyclohexyl)-4'fluorobiphenyl (No. 73) 5% by weight (E)-trans-(2-(trans-4-(4-fluorobutenyl)cyclohexyl)ethyl)-4-propylcyclohexane (No. 393) 5% by weight 4-cyanophenyl-4-ethylbenzoate 6% by weight 4-ethyl-4'-cyanobiphenyl 12% by weight 4-(trans-4-propylcyclohexyl)benzonitrile 6% by weight 4-ethylphenyl-4-methoxybenzoate 6% by weight 4-butoxyphenyl-trans-4-propylcyclohexanecarboxylate 8% by weight 4-ethoxyphenyl-trans-4-butylcyclohexanecarboxylate 8% by weight 4-methoxyphenyl-trans-4-pentylcyclohexanecarboxylate 8% by weight 4-fluorophenyl-4-(trans-4-propylcyclohexyl)benzoate 6% by weight 4-fluorophenyl-trans-4-(trans-4-propylcyclohexyl)cyclohexanecarboxylate 5% by weight 4-fluorophenyl-trans-4-(trans-4-pentylcyclohexyl)cyclohexanecarboxylate 5% by weight 4-fluorophenyl-4-(trans-4-propylcyclohexylcarbonyloxybenzoate 5% by weight 4-ethylphenyl-4-(trans-4-propylcyclohexylcarbonyloxy)benzoate 5% by weight

COMPOSITION EXAMPLE 35

(E)-4-(trans-4-(5-fluoropentenyl)cyclohexyl)benzonitrile (No. 19) 8% by weight (E)-3,5-difluoro-4-cyanophenyl-4-(3-pentenyl)benzoate 16% by weight 3-fluoro-4-cyanophenyl-4-ethoxymethylbenzoate 5% by weight 3-fluoro-4-cyanophenyl-4-propoxymethylbenzoate 13% by weight 4-(trans-4-propylcyclohexyl)-2-fluorobenzonitrile 11% by weight 4-(trans-4-propylcyclohexyl)benzonitrile 13% by weight 4-(trans-4-(trans-4-propylcyclohexyl)cyclohexyl)-2-fluorobenzonitrile 11% by weight 2-(4'-fluorobiphenyl-4-yl)-5-propylpyrimidine 8% by weight 2-(4'-fluorobiphenyl-4-yl)-5-butylpyrimidine 8% by weight 2-(4'-fluorobiphenyl-4-yl)-5-pentylpyrimidine 7% by weight

COMPOSITION EXAMPLE 36

(E)-(trans-4-(4-fluorobutenyl)cyclohexyl)-4-(trans-4-propylcyclohexyl)benzene (No. 207) 7% by weight (E)-4-(trans-4-(4-fluorobutenyl)cyclohexyl)-4'-fluorobiphenyl (No. 73) 5% by weight (E)-4-(trans-4-(4-fluorobutenyl)cyclohexyl)-4'-ethylbiphenyl (No. 36) 5% by weight (E)-4-(trans-4-(4-fluorobutenyl)cyclohexyl)-4'-trifluoromethylbiphenyl (No. 78) 5% by weight 4-(trans-4-ethylcyclohexyl)-3',4'-difluorobiphenyl 7% by weight 4-(trans-4-propylcyclohexyl)-3',4'-difluorobiphenyl 7% by weight 4-(trans-4-pentylcyclohexyl)-3',4'-difluorobiphenyl 14% by weight (trans-4-pentylcyclohexyl)-4-fluorobenzene 5% by weight (trans-4-heptylcyclohexyl)-4-fluorobenzene 5% by weight (trans-4-(trans-4-pentylcyclohexyl)cyclohexyl)-4-trifluoromethoxybenzene 8% by weight (trans-4-(2-(trans-4-propylcyclohexyl)ethyl)cyclohexyl)-4-trifluoromethoxybenzene 8% by weight (trans-4-(2-trans-4-pentylcyclohexyl)ethyl)cyclohexyl)-4-trifluoromethoxybenzene 8% by weight (2-(trans-4-(trans-4-propylcyclohexyl)cyclohexyl)ethyl)-4-trifluoromethoxybenzene 8% by weight (2-(trans-4-(trans-4-pentylcyclohexyl)cyclohexyl)ethyl)-4-trifluoromethoxybenzene 8% by weight

EXAMPLE

The present invention will be described in more detail by way of Examples, but it should not be construed to be limited thereto.

In addition, in these Examples, Cr represent crystal, N represents nematic phase, $S_B$ represents smectic B phase, $I_{so}$ represents isotropic liquid, and the unit of the phase transition points refers to ° C.

Example 1

Preparation of (E)-4-(trans-4-(4-fluorobutenyl) cyclohexyl)benzonitrile (a compound of No. 1 of the formula (1) wherein Q represents $CFH_2$; l represents 1; m, o and p all represent 0; $A_3$ represents trans-1,4-cyclohexylene group; ring B represents 1,4-phenylene group; $Z_3$ represents covalent bond; $L_1$ and $L_2$ both represent H; and $L_3$ represents CN).

A mixture of (3-fluoropropyl)triphenylphosphonium bromide (10.0 g, 24.8 millimols) with THF (50 ml) was cooled down to −20° C., followed by adding t-BuOK (3.1 g, 27.3 millimols) to the mixture, stirring the resulting mixture for 30 minutes, dropwise adding to the mixture, a THF (60 ml) solution of trans-4-(4-cyanophenyl) cyclohexanecarbaldehyde (5.8 g, 27.3 millimols) so as to keep the temperature at −20° C. or lower, stirring the mixture at the same temperature for 2 hours, adding water (50 ml) to the reaction product after completion of the reaction, extracting the product with ethyl acetate (300 ml), three times washing the resulting organic layer with water, drying it over anhydrous magnesium sulfate, distilling off the solvent under reduced pressure, and subjecting the residue to silica gel column chromatography (eluent: toluene), to obtain raw 4-(trans-4-(4-fluorobutenyl) cyclohexyl)benzonitrile (5.0 g).

This raw product (5.0 g, 19.4 millimols) was mixed with sodium benzenesulfinate dihydrate (5.8 g, 29.1 millimols), 6N-hydrochloric acid (4.9 ml, 29.1 millimols) and ethanol (30 ml), followed by heating the mixture under reflux for 12 hours, adding water (100 ml) to the reaction product after completion of the reaction, extracting the mixture with ethyl acetate (300 ml), three times washing the resulting organic layer with a saturated sodium carbonate aqueous solution and then three times with water, drying it over anhydrous sodium sulfate, distilling off the solvent under reduced pressure and subjecting the residue to silica gel column chromatography (eluent: toluene), to obtain raw (E)-4-(trans-4-(4-fluorobutenyl)cyclohexyl)benzonitrile (4.8 g). This raw product was recrystallized from ethanol to obtain the captioned product (1.0 g) (yield 15%).

Cr 38.0–38.6N 51.9–52.0 $I_{so}$

The following compounds (No. 2 to No. 34) were prepared according to the process of Example 1:

No.
2. (E)-(trans-4-(4-fluorobutenyl)cyclohexyl)-4-fluorobenzene
3. (E)-(trans-4-(4-fluorobutenyl)cyclohexyl)-4-bromobenzene
4. (E)-(trans-4-(4-fluorobutenyl)cyclohexyl)-4-fluoromethylbenzene
5. (E)-(trans-4-(4-fluorobutenyl)cyclohexyl)-4-difluoromethylbenzene
6. (E)-(trans-4-(4-fluorobutenyl)cyclohexyl)-4-difluoromethoxybenzene
7. (E)-(trans-4-(4-fluorobutenyl)cyclohexyl)-4-trifluoromethylbenzene
8. (E)-(trans-4-(4-fluorobutenyl)cyclohexyl)-4-trifluoromethoxybenzene
9. (E)-(trans-4-(4-fluorobutenyl)cyclohexyl)-4-ethylbenzene
10. (E)-(trans-4-(4-fluorobutenyl)cyclohexyl)-4-propylbenzene
11. (E)-(trans-4-(4-fluorobutenyl)cyclohexyl)-4-pentylbenzene
Cr 2.4–2.7 $I_{so}$
12. (E)-(trans-4-(4-fluorobutenyl)cyclohexyl)-3,4-difluorobenzene
13. (E)-(trans-4-(4-fluorobutenyl)cyclohexyl)-3-fluoro-4-chlorobenzene
14. (E)-4-(trans-4-(4-fluorobutenyl)cyclohexyl)-2-fluorobenzonitrile
15. (E)-4-(trans-4-(4-fluorobutenyl)cyclohexyl)-3-fluoro-4-trifluoromethylbenzene
16. (E)-4-(trans-4-(4-fluorobutenyl)cyclohexyl)-3-fluoro-4-trifluoromethoxybenzene
17. (E)-4-(trans-4-(4-fluorobutenyl)cyclohexyl)-3,5-difluoro-4-trifluoromethylbenzene
18. (E)-4-(trans-4-(4-fluorobutenyl)cyclohexyl)-3,4,5-trifluorobenzene
19. (E)-4-(trans-4-(5-fluoropentenyl)cyclohexyl) benzonitrile
Cr 19.1–19.5N 43.2–43.3 $I_{so}$
20. (E)-4-(trans-4-(5-fluoropentenyl)cyclohexyl)-4-trifluoromethoxybenzene
21. (E)-(trans-4-(5-fluoropentenyl)cyclohexyl)-4-hexyloxybenzene
22. (E)-(trans-4-(5-fluoropentenyl)cyclohexyl)-3-fluoro-4-difluoromethoxybenzene
23. (E)-(trans-4-(5-fluoropentenyl)cyclohexyl)-3-fluoro-4-trifluoromethylbenzene
24. (E)-(trans-4-(5-fluoropentenyl)cyclohexyl)-3,5-difluoro-4-difluoromethylbenzene
25. (E)-4-(trans-4-(5-fluoro-3-pentenyl)cyclohexyl) benzonitrile 26. (E)-(trans-4-(5-fluoro-3-pentenyl)cyclohexyl)-4-trifluoromethylbenzene
27. (E)-4-(trans-4-(6-fluoro-2-hexenyl)cyclohexyl)benzonitrile
28. (E)-(trans-4-(6-fluoro-2-hexenyl)cyclohexyl)-4-propylbenzene
29. (E)-4-(trans-4-(6-fluoro-3-hexenyl)cyclohexyl)benzonitrile
   Cr 47.0–48.0 (N 45.7–45.8) $I_{so}$
30. (E)-(trans-4-(6-fluoro-3-hexenyl)cyclohexyl)-3-fluoro-4-difluoromethylbenzene
31. (E)-(trans-4-(6-fluoro-3-hexenyl)cyclohexyl)-4-methoxyethylbenzene
32. (E)-(trans-4-(7-fluoro-3-heptenyl)cyclohexyl)-4-methoxymethylbenzene
33. (E)-4-(trans-4-(7-fluoro-4-heptenyl)cyclohexyl)benzonitrile
34. (E)-(trans-4-(7-fluoro-4-heptenyl)cyclohexyl)-4-ethylbenzene Example 2

Preparation of (E)-4-(trans-4-(4-fluorobutenyl)cyclohexyl-4'-cyanobiphenyl (a compound (No. 35) of the formula (1) wherein Q represents $CFH_2$; l represents 1; m and o both represents 0; p represents 1; $A_2$ represents trans-1,4-cyclohexylene group; $A_3$ and ring B both represent 1,4-phenylene group; $Z_2$ and $Z_3$ both represent covalent bond; $L_1$ and $L_2$ both represents H; and $L_3$ represents CN).

A mixture of (3-fluoropropyl)triphenylphosphonium bromide (17.6 g, 43.7 millimols) with THF (85 ml) was cooled down to –20° C., followed by adding to the mixture, t-BuOK (4.9 g, 43.7 millimols) stirring for one hour, dropwise adding to the mixture, a THF (110 ml) solution of trans-4-(4"-cyanobiphenyl)cyclohexanecarbaldehyde (11.0 g, 38.0 millimols) so as to keep the temperature at –20° C. or lower, stirring the mixture at the same temperature for 2 hours, adding water (100 ml) to the reaction product after completion of the reaction, extracting with ethyl acetate (600 ml), three times washing the resulting organic layer with water, drying over anhydrous magnesium sulphate, distilling off the solvent under reduced pressure, and subjecting the residue to silica gel column chromatography (eluent: toluene), to obtain raw 4-(trans-4-(4-fluorobutenyl)cyclohexyl)-4'-cyanobiphenyl (11.1 g).

This raw product (11.1 g, 33.2 millimols) was mixed with sodium benzenesulfinate dihydride (10.0 g, 49.8 millimols), 6N-hydrochloric acid (8.3 ml, 49.8 millimols) and a mixed solvent of toluene/ethanol (1/1) (50 ml), heating the mixture under reflux for 16 hours, adding water (100 ml) to the reaction product after completion of the reaction, extracting with toluene (200 ml), three times washing the resulting organic layer with a saturated sodium carbonate aqueous solution and three times with water, drying over anhydrous sodium sulfate, distilling off the solvent under reduced pressure and subjecting the residue to silica gel column chromatography (eluent: toluene), to obtain raw (E)-4-(trans-4-(4-fluorobutenyl)cyclohexyl)-4'-cyanobiphenyl (16.5 g). This product was recrystallized from a mixed solvent of ethyl acetate/heptane (3/7), to obtain the captioned compound (6.1 g, yield 48%).

Cr 130.3–131.1N 216.4–217.1 $I_{so}$

The following compounds (No. 36 to No. 71) were prepared according to the process of Example 2.
No.
36. (E)-4-(trans-4-(4-fluorobutenyl)cyclohexyl)-4'-ethylbiphenyl
   Cr room temperature or lower $S_B$ 166.9–167.5N 181.0 $I_{so}$
37. (E)-4-(trans-4-(4-fluorobutenyl)cyclohexyl)-4'-propylbiphenyl
   Cr room temperature or lower $S_B$ 177.8–178.8N 196.9–197.1 $I_{so}$
38. (E)-4-(trans-4-(4-fluorobutenyl)cyclohexyl)-4'-propoxyethylbiphenyl
39. (E)-4-(trans-4-(4-fluorobutenyl)cyclohexyl)-3'-fluoro-4'-cyanobiphenyl
40. (E)-4-(trans-4-(4-fluorobutenyl)cyclohexyl)-3',5'-difluoro-4'-cyanobiphenyl
41. (E)-4-(trans-4-(5-fluoropentenyl)cyclohexyl)-4'-cyanobiphenyl
   Cr 118.9–119.8N 191.5–191.7 $I_{so}$
42. (E)-4-(trans-4-(5-fluoropentenyl)cyclohexyl)-4'-methoxymethylbiphenyl
43. (E)-4-(trans-4-(5-fluoropentenyl)cyclohexyl)-3'-fluoro-4'-cyanobiphenyl
44. (E)-4-(trans-4-(5-fluoropentenyl)cyclohexyl)-3',5'-difluoro-4'-cyanobiphenyl
45. (E)-4-(trans-4-(5-fluoro-3-pentenyl)cyclohexyl)-4'-cyanobiphenyl
46. (E)-4-(trans-4-(5-fluoro-3-pentenyl)cyclohexyl)-4'-butylbiphenyl
47. (E)-4-(trans-4-(5-fluoro-3-pentenyl)cyclohexyl)-3'-fluoro-4'-cyanobiphenyl
48. (E)-4-(trans-4-(5-fluoro-3-pentenyl)cyclohexyl)-3',5'-difluoro-4'-cyanobiphenyl
49. (E)-4-(trans-4-(6-fluoro-2-hexenyl)cyclohexyl)-4'-cyanobiphenyl
50. (E)-4-(trans-4-(6-fluoro-2-hexenyl)cyclohexyl)-4'-butoxybiphenyl
51. (E)-4-(trans-4-(6-fluoro-3-hexenyl)cyclohexyl)-4'-ethylbiphenyl
52. (E)-4-(trans-4-(7-fluoro-4-heptenyl)cyclohexyl)-4'-cyanobiphenyl
53. (E)-4-(trans-4-(7-fluoro-4-heptenyl)cyclohexyl)-4'-methylbiphenyl
54. (E)-4-(2-(trans-4-(4-fluorobutenyl)cyclohexyl)ethyl-4'-cyanobiphenyl
55. (E)-4-(2-(trans-4-(4-fluorobutenyl)cyclohexyl)ethyl)-4'-ethylbiphenyl
56. (E)-4-(2-(trans-4-(4-fluorobutenyl)cyclohexyl)ethyl)-4'-propylbiphenyl
57. (E)-4-(2-(trans-4-(4-fluorobutenyl)cyclohexyl)ethyl)-4'-pentylbiphenyl
58. (E)-4-(2-(trans-4-(4-fluorobutenyl)cyclohexyl)ethyl)-3'-fluoro-4'-cyanobiphenyl
59. (E)-4-(2-(trans-4-(4-fluorobutenyl)cyclohexyl)ethyl)-3',5'-difluoro-4'-cyanobiphenyl
60. (E)-4-(2-(trans-4-(5-fluoropentenyl)cyclohexyl)ethyl)-4'-cyanobiphenyl
61. (E)-4-(2-(trans-4-(5-fluoropentenyl)cyclohexyl)ethyl)-4'-butylbiphenyl
62. (E)-4-(2-(trans-4-(5-fluoropentenyl)cyclohexyl)ethyl)-4'-propoxymethylbiphenyl
63. (E)-4-(2-(trans-4-(5-fluoropentenyl)cyclohexyl)ethyl)-3'-fluoro-4'-cyanobiphenyl
64. (E)-4-(2-(trans-4-(5-fluoro-2-pentenyl)cyclohexyl)ethyl)-4'-cyanobiphenyl
65. (E)-4-(2-(trans-4-(5-fluoro-3-pentenyl)cyclohexyl)ethyl)-4'-heptylbiphenyl
66. (E)-4-(2-(trans-4-(6-fluoro-3-hexenyl)cyclohexyl)ethyl)-4'-cyanobiphenyl
67. (E)-4-(2-(trans-4-(6-fluoro-3-hexenyl)cyclohexyl)ethyl)-4'-methoxyethylbiphenyl
68. (E)-4-(2-(trans-4-(7-fluoroheptenyl)cyclohexyl)ethyl)-4'-methoxymethylbiphenyl 69. (E)-4-(2-trans-4-(7-fluoro-3-heptenyl)cyclohexyl)ethyl)-3'-fluoro-4'-cyanobiphenyl 70. (E)-4-(2-(trans-4-(7-fluoro-4-heptenyl)cyclohexyl)ethyl)-3',5'-difluoro-4'-cyanobiphenyl 71. (E)-4-(2-(trans-4-(7-fluoro-4-heptenyl)cyclohexyl)ethyl)-4'-methylbiphenyl Example 3

Preparation of (E)-4-(trans-4-(4-fluorobutenyl)cyclohexyl)-4'-chlorobiphenyl (a compound of No. 72 of the formula (1) wherein Q represents $CFH_2$; l represents 1; m and o both represent 0; p represents 1; $A_2$ represents trans-1,4-cyclohexylene group; $A_3$ and ring B both represent 1,4-phenylene group; $Z_2$ and $Z_3$ both represent covalent bond; $L_1$ and $L_2$ both represent H; and $L_3$ represents Cl)

A mixture of (3-fluoropropyl)triphenylphosphonium bromide (14.0 g, 34.6 millimols) with THF (65 ml) was cooled down to −20° C., followed by adding to the mixture, t-BuOK (4.0 g, 34.6 millimols), stirring the mixture for one hour, dropwise adding thereto a THF (100 ml) solution of trans-4-(4''-chlorobiphenyl)cyclohexanecarbaldehyde (9.0 g, 34.6 millimols) so as to keep the temperature at −20° C. or lower, stirring at the same temperature for 2 hours, and treating the reaction product in the same manner as in Example 2 except that the quantity of ethyl acetate used for extraction was made 500 ml, to obtain raw 4-(trans-4-(4-fluorobutenyl)cyclohexyl)-4'-chlorobiphenyl (9.2 g).

This raw product (9.2 g, 26.7 millimols) was mixed with sodium benzenesulfinate dihydrate (8.0 g, 40.0 millimols), 6N-hydrochloric acid (6.7 ml, 40.0 millimols) and a mixed solvent of toluene/ethanol (1/1) (70 ml), followed by heating the mixture under reflux for 12 hours, and treating the reaction product in the same manner as in Example 2 except that the toluene of effluent was made a mixed solution of ethyl acetate/heptane (6/4), to obtain raw (E)-4-(trans-4-(4-fluorobutenyl)cyclohexyl)-4'-chlorobiphenyl (9.2 g).

This product was recrystallized from a mixed solvent of ethyl acetate/heptane (4/6), to obtain the captioned compound (2.9 g, yield 28%).

Cr 158.2–159.1N 180.9–181.1 $I_{so}$

The following compounds (No. 73 to No. 116) were prepared according to the process of Example 3.
No.

73. (E)-4-(trans-4-(4-fluorobutenyl)cyclohexyl)-4'-fluorobiphenyl
Cr 105.2–106.3N 162.0–162.2 $I_{so}$ 74. (E)-4-(trans-4-(4-fluorobutenyl)cyclohexyl)-4'-bromobiphenyl 75. (E)-4-(trans-4-(4-fluorobutenyl)cyclohexyl)-4'-difluoromethylbiphenyl 76. (E)-4-(trans-4-(4-fluorobutenyl)cyclohexyl)-3',4'-difluorobiphenyl
Cr 51.6–52.7N 118.1–118.2 $I_{so}$ 77. (E)-4-(trans-4-(4-fluorobutenyl)cyclohexyl)-3'-fluoro-4'-chlorobiphenyl 78. (E)-4-(trans-4-(4-fluorobutenyl)cyclohexyl)-4'-trifluoromethylbiphenyl
Cr 111.4–112.0N 128.7–128.8 $I_{so}$ 79. (E)-4-(trans-4-(4-fluorobutenyl)cyclohexyl)-3'-fluoro-4'-difluoromethoxybiphenyl 80. (E)-4-(trans-4-(4-fluorobutenyl)cyclohexyl)-3'-fluoro-4'-trifluoromethoxybiphenyl 81. (E)-4-(trans-4-(4-fluorobutenyl)cyclohexyl)-3',4',5'-trifluorobiphenyl 82. (E)-4-(trans-4-(4-fluorobutenyl)cyclohexyl)-3',5'-difluoro-4'-chlorobiphenyl 83. (E)-4-(trans-4-(4-fluorobutenyl)cyclohexyl)-3',5'-difluoro-4'-fluoromethylbiphenyl 84. (E)-4-(trans-4-(4-fluorobutenyl)cyclohexyl)-3',5'-difluoro-4'-trifluoromethylbiphenyl 85. (E)-4-(trans-4-(5-fluoropentenyl)cyclohexyl)-4'-chlorobiphenyl 86. (E)-4-(trans-4-(5-fluoropentenyl)cyclohexyl)-4'-fluoromethylbiphenyl 87. (E)-4-(trans-4-(5-fluoropentenyl)cyclohexyl)-3',4',5'-trifluorobiphenyl 88. (E)-4-(trans-4-(5-fluoropentenyl)cyclohexyl)-3',5'-difluoro-4-trifluoromethylbiphenyl 89. (E)-4-(trans-4-(5-fluoro-3-pentenyl)cyclohexyl)-3'-fluoro-4'-difluoromethylbiphenyl 90. (E)-4-(trans-4-(5-fluoro-3-pentenyl)cyclohexyl)-3',4',5'-trifluorobiphenyl 91. (E)-4-(trans-4-(5-fluoro-3-pentenyl)cyclohexyl)-3',5'-difluoro-4'-trifluoromethoxybiphenyl 92. (E)-4-(trans-4-(6-fluoro-2-hexenyl)cyclohexyl)-3',5'-difluoro-4'-trifluoromethoxybiphenyl 93. (E)-4-(trans-4-(6-fluoro-3-hexenyl)cyclohexyl)-4'-difluoromethoxybiphenyl 94. (E)-4-(trans-4-(7-fluoro-4-heptenyl)cyclohexyl)-3'-fluoro-4'-trifluoromethoxybiphenyl 95. (E)-4-(2-(trans-4-(4-fluorobutenyl)cyclohexyl)ethyl)-4'-fluorobiphenyl 96. (E)-4-(2-(trans-4-(4-fluorobutenyl)cyclohexyl)ethyl)-4'-bromobiphenyl 97. (E)-4-(2-(trans-4-(4-fluorobutenyl)cyclohexyl)ethyl)-4'-chlorobiphenyl 98. (E)-4-(2-(trans-4-(4-fluorobutenyl)cyclohexyl)ethyl)-4'-difluoromethylbiphenyl 99. (E)-4-(2-(trans-4-(4-fluorobutenyl)cyclohexyl)ethyl)-3',4'-difluorobiphenyl 100. (E)-4-(2-(trans-4-(4-fluorobutenyl)cyclohexyl)ethyl)-3'-fluoro-4'-trifluoromethylbiphenyl 101. (E)-4-(2-(trans-4-(4-fluorobutenyl)cyclohexyl)ethyl)-3'-fluoro-4'-trifluoromethoxybiphenyl 102. (E)-4-(2-(trans-4-(4-fluorobutenyl)cyclohexyl)ethyl)-3',4',5'-trifluorobiphenyl 103. (E)-4-(2-(trans-4-(4-fluorobutenyl)cyclohexyl)ethyl)-3',5'-difluoro-4'-trifluoromethylbiphenyl 104. (E)-4-(2-trans-4-(5-fluoropentenyl)cyclohexyl)ethyl)-3',4'-difluorobiphenyl 105. (E)-4-(2-trans-4-(5-fluoropentenyl)cyclohexyl)ethyl)-3'-fluoro-4'-chlorobiphenyl 106. (E)-4-(2-trans-4-(5-fluoropentenyl)cyclohexyl)ethyl)-3',5'-difluoro-4'-difluoromethoxybiphenyl 107. (E)-4-(2-trans-4-(5-fluoro-2-pentenyl)cyclohexyl)ethyl)-3',4',5'-trifluorobiphenyl 108. (E)-4-(2-(trans-4-(5-fluoro-3-pentenyl)cyclohexyl)ethyl)-3'-fluoro-4'-trifluoromethylbiphenyl 109. (E)-4-(2-(trans-4-(5-fluoro-3-pentenyl)cyclohexyl)ethyl)-3',5'-difluoro-4'-fluoromethylbiphenyl 110. (E)-4-(2-(trans-4-(6-fluorohexenyl)cyclohexyl)ethyl)-3',5'-difluoro-4'-trifluoromethoxybiphenyl 111. (E)-4-(2-(trans-4-(6-fluorohexenyl)cyclohexyl)ethyl)-3'-fluoro-4'-difluoromethylbiphenyl 112. (E)-4-(2-trans-4-(6-fluoro-2-hexenyl)cyclohexyl)ethyl)-3',5'-difluoro-4'-chlorobiphenyl 113. (E)-4-(2-trans-4-(7-fluoro-2-pentenyl)cyclohexyl)ethyl)-3'-fluoro-4'-trifluoromethoxybiphenyl 114. (E)-4-(2-trans-4-(7-fluoro-3-pentenyl)cyclohexyl)ethyl)-4'-fluorobiphenyl 115. (E)-4-(2-trans-4-(7-fluoro-3-pentenyl)cyclohexyl)ethyl)-4'-difluoromethoxybiphenyl 116. (E)-4-(2-(trans-4-(7-fluoro-4-pentenyl)cyclohexyl)ethyl)-4'-trifluoromethylbiphenyl

Example 4

Preparation of (E)-4-(trans-4-(trans-4-(4-fluorobutenyl)cyclohexyl)cyclohexyl)benzonitrile (a compound No. 117 of the formula (1) wherein Q represents $CFH_2$; l represents 1; m and o both represent 0; p represents 1; $A_2$ and $A_3$ both represent trans-1,4-cyclohexylene group; ring B represents 1,4-phenylene group; $Z_2$ and $Z_3$ both represent covalent bond; $L_1$ and $L_2$ both represent H; and $L_3$ represents CN.

A mixture of (3-fluoropropyl)triphenylphosphonium bromide (15.0 g, 37.2 millimols) with THF (75 ml) was cooled down to −20° C., followed by adding t-BuOK (4.2 g, 37.2 millimols) to the mixture, stirring for one hour, dropwise adding to the mixture, a THF (100 ml) solution of trans-4-(trans-4-(4-cyanophenyl)cyclohexyl)cyclohexanecarbaldehyde (10.0 g, 37.2 millimols) so as to keep the temperature at −20° C. or lower, stirring the mixture at the same temperature for 2 hours, and treating the reaction product in the same manner as in Example 3, to obtain raw (E)-4-(trans-4-(trans-4-(4-fluorobutenyl)cyclohexyl)cyclohexyl)benzonitrile (9.9 g).

This raw product (9.9 g, 29.2 millimols) was mixed with sodium benzenesulfinate dihydrate (8.8 g, 43.7 millimols), 6N-hydrochloric acid (7.3 ml, 43.7 millimols) and a mixed solvent of toluene/ethanol (1/1) (50 ml), followed by heating the mixture under reflux for 12 hours, treating the resulting product in the same manner as in Example 3, to obtain raw (E)-4-(trans-4-(trans-4-(4-fluorobutenyl)cyclohexyl)cyclohexyl)benzonitrile (9.9 g). This product was recrystallized from a mixed solvent of ethyl acetate/heptane (3/7), to obtain the captioned compound (3.9 g, yield 33.9%).

Cr 111.4–112.0N 211.3–211.6 $I_{so}$

The following compounds (No. 118 to No. 137) were prepared according to the process of Example 4:
No.
118. (E)-4-(trans-4-(trans-4-(4-fluorobutenyl)cyclohexyl)cyclohexyl)-2-fluorobenzonitrile
119. (E)-4-(trans-4-(trans-4-(4-fluorobutenyl)cyclohexyl)cyclohexyl)-2,6-difluorobenzonitrile
120. (E)-4-(trans-4-(trans-4-(5-fluoropentenyl)cyclohexyl)cyclohexyl)benzonitrile
121. (E)-4-(trans-4-(trans-4-(5-fluoropentenyl)cyclohexyl)cyclohexyl)-2-fluorobenzonitrile
122. (E)-4-(trans-4-(trans-4-(5-fluoropentenyl)cyclohexyl)cyclohexyl)-2,6-difluorobenzonitrile
123. (E)-4-(trans-4-(trans-4-(5-fluoro-3-pentenyl)cyclohexyl)cyclohexyl)benzonitrile
124. (E)-4-(trans-4-(trans-4-(5-fluoro-3-pentenyl)cyclohexyl)cyclohexyl)-2-fluorobenzonitrile
125. (E)-4-(trans-4-(trans-4-(5-fluoro-2-pentenyl)cyclohexyl)cyclohexyl)benzonitrile
126. (E)-4-(trans-4-(trans-4-(7-fluoro-3-heptenyl)cyclohexyl)cyclohexyl)benzonitrile
127. (E)-4-(trans-4-(2-(trans-4-(4-fluorobutenyl)cyclohexyl)ethyl)cyclohexyl)benzonitrile
128. (E)-4-(trans-4-(2-(trans-4-(4-fluorobutenyl)cyclohexyl)ethyl)cyclohexyl)-2-fluorobenzonitrile
129. (E)-4-(trans-4-(2-(trans-4-(4-fluorobutenyl)cyclohexyl)ethyl)cyclohexyl)-2,6-difluorobenzonitrile
130. (E)-4-(trans-4-(2-(trans-4-(5-fluoropentenyl)cyclohexyl)ethyl)cyclohexyl)benzonitrile
131. (E)-4-(trans-4-(2-(trans-4-(5-fluoropentenyl)cyclohexyl)ethyl)cyclohexyl)-2-fluorobenzonitrile
132. (E)-4-(trans-4-(2-(trans-4-(5-fluoro-2-pentenyl)cyclohexyl)ethyl)cyclohexyl)-2-fluorobenzonitrile
133. (E)-4-(trans-4-(2-trans-4-(6-fluorohexenyl)cyclohexyl)ethyl)cyclohexyl)benzonitrile
134. (E)-4-(trans-4-(2-(trans-4-(6-fluorohexenyl)cyclohexyl)ethyl)cyclohexyl)-2,6-difluorobenzonitrile
135. (E)-4-(trans-4-(2-(trans-4-(7-fluoro-2-heptenyl)cyclohexyl)ethyl)cyclohexyl)benzonitrile
136. (E)-4-(trans-4-(2-(trans-4-(7-fluoro-3-heptenyl)cyclohexyl)ethyl)cyclohexyl)-2-fluorobenzonitrile
137. (E)-4-(trans-4-(2-(trans-4-(7-fluoro-4-heptenyl)cyclohexyl)ethyl)cyclohexyl)benzonitrile

Example 5

Preparation of (E)-(trans-4-(trans-4-(4-fluorobutenyl)cyclohexyl)cyclohexyl)-3-fluoro-4-trifluoromethylbenzene (a compound No. 138 of the formula (1) wherein Q represents $CFH_2$; l represents 1; m and o both represent 0; p represent 1; $A_2$ and $A_3$ both represent trans-1,4-cyclohexylene group; ring B represents 2-fluoro-1,4-phenylene group ($L_1$=F); $Z_2$ and $Z_3$ both represent covalent bond; $L_2$ represents H; and $L_3$ represents $CF_3$)

A mixture of (3-fluoropropyl)triphenylphosphonium bromide (11.2 g, 27.8 millimols) with THF (50 ml) was cooled down to −20° C., followed by adding t-BuOK (3.1 g, 27.8 millimols) to the mixture, stirring for one hour, dropwise adding to the mixture, a THF (100 ml) solution of trans-4-(trans-4-(3-fluoro-4-trifluoromethylphenyl)cyclohexyl)cyclohexanecarbaldehyde (9.0 g, 25.3 millimols) so as to keep the temperature at −20° C. or lower, stirring the mixture at the same temperature for 2 hours, and treating the reaction product in the same manner as in Example 2 except that the quantity of ethyl acetate used for extraction was made 400 ml, to obtain raw (trans-4-(trans-4-(4-fluorobutenyl)cyclohexyl)cyclohexyl)-3-fluoro-4-trifluoromethylbenzene (8.9 g).

This raw product (8.9 g, 22.2 millimols) was mixed with sodium benzenesulfinate dihydrate (6.7 g, 33.3 millimols), 6N-hydrochloric acid (5.6 ml, 33.3 millimols) and a mixed solvent of toluene/ethanol (1/1) (45 ml) , followed by heating the mixture under reflux for 12 hours, and treating the reaction product in the same manner as in Example 2, to obtain raw (E)-(trans-4-(trans-4-(4-fluorobutenyl)cyclohexyl)cyclohexyl-3-fluoro-4-trifluoromethylbenzene (8.9 g). This product was recrystallized from a mixed solvent of ethyl acetate/heptane (3/7), to obtain the captioned compound (3.3 g, yield: 32.7%).

The following compounds (No. 139 to No. 175) were prepared according to the process of Example 5:
139. (E)-(trans-4-(trans-4-(4-fluorobutenyl)cyclohexyl)cyclohexyl)-4-trifluoromethylbenzene
140. (E)-(trans-4-(trans-4-(4-fluorobutenyl)cyclohexyl)cyclohexyl)-4-difluoromethoxybenzene
141. (E)-(trans-4-(trans-4-(4-fluorobutenyl)cyclohexyl)cyclohexyl)-4-trifluoromethoxybenzene
142. (E)-(trans-4-(trans-4-(4-fluorobutenyl)cyclohexyl)cyclohexyl)-3-fluoro-4-difluoromethylbenzene
143. (E)-(trans-4-(trans-4-(4-fluorobutenyl)cyclohexyl)cyclohexyl)-3-fluoro-4-trifluoromethoxybenzene
144. (E)-(trans-4-(trans-4-(4-fluorobutenyl)cyclohexyl)cyclohexyl)-3,5-difluoro-4-fluoromethylbenzene
145. (E)-(trans-4-(trans-4-(4-fluorobutenyl)cyclohexyl)cyclohexyl)-3,5-difluoro-4-trifluoromethylbenzene
146. (E)-(trans-4-(trans-4-(4-fluorobutenyl)cyclohexyl)cyclohexyl)-3,5-difluoro-4-trifluoromethoxybenzene
147. (E)-(trans-4-(trans-4-(5-fluoropentenyl)cyclohexyl)cyclohexyl)-4-fluoromethylbenzene
148. (E)-(trans-4-(trans-4-(5-fluoropentenyl)cyclohexyl)cyclohexyl)-4-trifluoromethylbenzene
149. (E)-(trans-4-(trans-4-(5-fluoropentenyl)cyclohexyl)cyclohexyl)-4-trifluoromethoxybenzene 150. (E)-(trans-4-(trans-4-(5-fluoropentenyl)cyclohexyl)cyclohexyl)-3-fluoro-4-trifluoromethylbenzene
151. (E)-(trans-4-(trans-4-(5-fluoropentenyl)cyclohexyl)cyclohexyl)-3-fluoro-4-difluoromethoxybenzene
152. (E)-(trans-4-(trans-4-(5-fluoropentenyl)cyclohexyl)cyclohexyl)-3-fluoro-4-trifluoromethoxybenzene
153. (E)-(trans-4-(trans-4-(5-fluoropentenyl)cyclohexyl)cyclohexyl)-3,5-difluoro-4-trifluoromethylbenzene
154. (E)-(trans-4-(trans-4-(5-fluoro-3-pentenyl)cyclohexyl)cyclohexyl)-3,5-difluoro-4-trifluoromethylbenzene
155. (E)-(trans-4-(trans-4-(6-fluoro-2-hexenyl)cyclohexyl)cyclohexyl)-4-trifluoromethylbenzene
156. (E)-(trans-4-(trans-4-(7-fluoro-2-heptenyl)cyclohexyl)cyclohexyl)-4-difluoromethylbenzene
157. (E)-(trans-4-(trans-4-(7-fluoro-2-heptenyl)cyclohexyl)cyclohexyl)-3-fluoro-4-trifluoromethoxybenzene
158. (E)-(trans-4-(trans-4-(7-fluoro-4-heptenyl)cyclohexyl)cyclohexyl)-3,4-difluoro-5-trifluoromethoxybenzene
159. (E)-(trans-4-(2-(trans-4-(4-fluorobutenyl)cyclohexyl)ethyl)cyclohexyl)-4-difluoromethylbenzene
160. (E)-(trans-4-(2-(trans-4-(4-fluorobutenyl)cyclohexyl)ethyl)cyclohexyl)-4-trifluoromethylbenzene
161. (E)-(trans-4-(2-(trans-4-(4-fluorobutenyl)cyclohexyl)ethyl)cyclohexyl)-4-trifluoromethoxybenzene
162. (E)-(trans-4-(2-(trans-4-(4-fluorobutenyl)cyclohexyl)ethyl)cyclohexyl)-3-fluoro-4-trifluoromethylbenzene
163. (E)-(trans-4-(2-(trans-4-(4-fluorobutenyl)cyclohexyl)ethyl)cyclohexyl)-3-fluoro-4-difluoromethoxybenzene
164. (E)-(trans-4-(2-(trans-4-(4-fluorobutenyl)cyclohexyl)ethyl)cyclohexyl)-3-fluoro-4-trifluoromethoxybenzene
165. (E)-(trans-4-(2-(trans-4-(4-fluorobutenyl)cyclohexyl)ethyl)cyclohexyl)-3,5-difluoro-4-trifluoromethylbenzene
166. (E)-(trans-4-(2-(trans-4-(4-fluorobutenyl)cyclohexyl)ethyl)cyclohexyl)-3,5-difluoro-4-trifluoromethoxybenzene
167. (E)-(trans-4-(2-(trans-4-(5-fluoropentenyl)cyclohexyl)ethyl)cyclohexyl)-3-fluoro-4-trifluoromethoxybenzene
168. (E)-(trans-4-(2-(trans-4-(5-fluoropentenyl)cyclohexyl)ethyl)cyclohexyl)-3,5-difluoro-4-fluoromethylbenzene
169. (E)-(trans-4-(2-(trans-4-(5-fluoropentenyl)cyclohexyl)ethyl)cyclohexyl)-3,5-difluoro-4-trifluoromethylbenzene
170. (E)-(trans-4-(2-(trans-4-(6-fluorohexenyl)cyclohexyl)ethyl)cyclohexyl)-4-trifluoromethoxybenzene
171. (E)-(trans-4-(2-(trans-4-(6-fluoro-2-hexenyl)cyclohexyl)ethyl)cyclohexyl)-3-fluoro-4-trifluoromethylbenzene
172. (E)-(trans-4-(2-(trans-4-(6-fluoro-3-hexenyl)cyclohexyl)ethyl)cyclohexyl)-3,5-difluoro-4-trifluoromethylbenzene
173. (E)-(trans-4-(2-(trans-4-(7-fluoroheptenyl)cyclohexyl)ethyl)cyclohexyl)-4-trifluoromethylbenzene
174. (E)-(trans-4-(2-(trans-4-(7-fluoroheptenyl)cyclohexyl)ethyl)cyclohexyl)-3-fluoro-4-difluoromethoxybenzene
175. (E)-(trans-4-(2-(trans-4-(7-fluoro-4-heptenyl)cyclohexyl)ethyl)cyclohexyl)-3,5-difluoro-4-trifluoromethoxybenzene Example 6

Preparation of (E)-(trans-4-(trans-4-(4-fluorobutenyl)cyclohexyl)cyclohexyl)-3,4-difluorobenzene (a compound of No. 176 of the formula (1), wherein Q represents $CFH_2$; l represent 1; m and o both represent 0; p represents 1; $A_2$ and $A_3$ both represent trans-1,4-cyclohexylene group; ring B represents 2-fluoro-1,4-phenylene group ($L_1$=F); $Z_2$ and $Z_3$ both represent covalent bond; $L_3$ represents F; and $L_2$ represents H.

A mixture of (3-fluoropropyl)triphenylphosphonium bromide (13.8 g, 34.1 millimols) with THF (60 ml) was cooled down to -20° C., followed by adding t-BuOK (3.5 g, 34.1 millimols) to the mixture, stirring for one hour, dropwise adding to the mixture, a THF (120 ml) solution of trans-4-(trans-4-(3,4-difluorophenyl)cyclohexyl)cyclohexanecarbaldehyde (9.5 g, 31.0 millimols) so as to keep the temperature at -20° C. or lower, stirring the mixture at the same temperature for 2 hours, and treating the reaction product in the same manner as in Example 2, to obtain raw (trans-4-(trans-4-(4-fluorobutenyl)cyclohexyl)cyclohexyl)-3,4-difluorobenzene (9.2 g).

This raw product (9.2 g, 25.4 millimols) was mixed with sodium benzenesulfinate dihydrate (7.9 g, 39.4 millimols), 6N-hydrochloric acid (6.6 ml, 39.4 millimols) and a mixed solvent of toluene/ethanol (1/1) (50 ml), followed by heating the mixture under reflux for 12 hours, and treating the reaction product in the same manner as in Example 2, to obtain raw (E)-(trans-4-(trans-4-(4-fluorobutenyl)cyclohexyl)cyclohexyl)-3,4-difluorobenzene (9.1 g). This product was recrystallized from a mixed solvent of ethyl acetate/heptane (3/7), to obtain the captioned product (4.9 g, yield: 45.0%).

The following compounds (No. 177 to No. 203) were prepared according to Example 6:
No.
177. (E)-(trans-4-(trans-4-(4-fluorobutenyl)cyclohexyl)cyclohexyl)-4-fluorobenzene
178. (E)-(trans-4-(trans-4-(4-fluorobutenyl)cyclohexyl)cyclohexyl)-4-bromobenzene
179. (E)-(trans-4-(trans-4-(4-fluorobutenyl)cyclohexyl)cyclohexyl)-3-fluoro-4-chlorobenzene
180. (E)-(trans-4-(trans-4-(4-fluorobutenyl)cyclohexyl)cyclohexyl)-3,4,5-trifluorobenzene
181. (E)-(trans-4-(trans-4-(4-fluorobutenyl)cyclohexyl)cyclohexyl)-3,5-difluoro-4-chlorobenzene
182. (E)-(trans-4-(trans-4-(5-fluoropentenyl)cyclohexyl)cyclohexyl)-4-chlorobenzene
183. (E)-(trans-4-(trans-4-(5-fluoropentenyl)cyclohexyl)cyclohexyl)-4-fluorobenzene
184. (E)-(trans-4-(trans-4-(5-fluoropentenyl)cyclohexyl)cyclohexyl)-3,4-difluorobenzene
185. (E)-(trans-4-(trans-4-(5-fluoropentenyl)cyclohexyl)cyclohexyl)-3,4,5-trifluorobenzene
186. (E)-(trans-4-(trans-4-(5-fluoro-3-pentenyl)cyclohexyl)cyclohexyl)-3,4,5-trifluorobenzene
187. (E)-(trans-4-(trans-4-(6-fluoro-2-hexenyl)cyclohexyl)cyclohexyl)-3,4,5-trifluorobenzene
188. (E)-(trans-4-(trans-4-(7-fluoro-4-heptenyl)cyclohexyl)cyclohexyl)-3,4,5-trifluorobenzene
189. (E)-(trans-4-(2-(trans-4-(4-fluorobutenyl)cyclohexyl)ethyl)cyclohexyl)-4-fluorobenzene
190. (E)-(trans-4-(2-(trans-4-(4-fluorobutenyl)cyclohexyl)ethyl)cyclohexyl)-4-bromobenzene
191. (E)-(trans-4-(2-(trans-4-(4-fluorobutenyl)cyclohexyl)ethyl)cyclohexyl)-4-chlorobenzene
192. (E)-(trans-4-(2-(trans-4-(4-fluorobutenyl)cyclohexyl)ethyl)cyclohexyl)-3,4-difluorobenzene
193. (E)-(trans-4-(2-(trans-4-(4-fluorobutenyl)cyclohexyl)ethyl)cyclohexyl)-3-fluoro-4-chlorobenzene
194. (E)-(trans-4-(2-(trans-4-(4-fluorobutenyl)cyclohexyl)ethyl)cyclohexyl)-3,4,5-trifluorobenzene
195. (E)-(trans-4-(2-(trans-4-(5-fluoropentenyl)cyclohexyl)ethyl)cyclohexyl)-3,4,5-trifluorobenzene
196. (E)-(trans-4-(2-(trans-4-(5-fluoropentenyl)cyclohexyl)ethyl)cyclohexyl)-3,5-difluoro-4-chlorobenzene
197. (E)-(trans-4-(2-trans-4-(5-fluoro-2-pentenyl)cyclohexyl)ethyl)cyclohexyl)-3,4-difluorobenzene
198. (E)-(trans-4-(2-trans-4-(6-fluorohexenyl)cyclohexyl)ethyl)cyclohexyl)-4-fluorobenzene 199. (E)-(trans-4-(2-(trans-4-(6-fluoro-2-hexenyl)cyclohexenyl)ethyl)cyclohexyl)-3-fluoro-4-chlorobenzene
200. (E)-(trans-4-(2-(trans-4-(6-fluoro-3-hexenyl)cyclohexenyl)ethyl)cyclohexyl)-3,4,5-trifluorobenzene
201. (E)-(trans-4-(2-(trans-4-(7-fluoroheptyl)cyclohexyl)ethyl)cyclohexyl)-4-chlorobenzene
202. (E)-(trans-4-(2-(trans-4-(7-fluoro-2-heptenyl)cyclohexyl)ethyl)cyclohexyl)-3,4,5-trifluorobenzene
203. (E)-(trans-4-(2-(trans-4-(7-fluoro-4-heptenyl)cyclohexyl)ethyl)cyclohexyl)-3,5-difluoro-4-chlorobenzene

Example 7

Preparation of (E)-(trans-4-(trans-4-(4-fluorobutenyl)cyclohexyl)cyclohexyl)-4-ethylbenzene (a compound of No. 204 of the formula (1) wherein Q represents $CFH_2$; l represents 1; m and o both represent 0; p represents 1; $A_2$ and $A_3$ both represent trans-1,4-cyclohexylene group; ring B represents 1,4-phenylene group; $Z_2$ and $Z_3$ both represent covalent bond; $L_1$ and $L_2$ both represent H; and $L_3$ represents $C_2H_5$.

A mixture of (3-fluoropropyl)triphenylphosphonium bromide (13.4 g, 33.2 millimols) with THF (50 ml) was cooled down to $-20°$ C., followed by adding t-BuOK (3.7 g, 33.2 millimols) to the mixture, stirring for one hour, dropwise adding to the mixture, a THF (90 ml) solution of trans-4-(trans-4-(4-ethylphenyl)cyclohexyl)cyclohexanecarbaldehyde (9.0 g, 30.2 millimols) so as to keep the temperature at $-20°$ C. or lower, stirring the mixture at the same temperature for 2 hours, and treating the reaction product in the same manner as in Example 2 except that the quantity of ethyl acetate used for extraction was made 400 ml, to obtain raw (trans-4-(trans-4-fluorobutenyl)cyclohexyl)cyclohexyl)-4-ethylbenzene (9.1 g).

This raw product (9.1 g, 26.6 millimols) was mixed with sodium benzenesulfinate dihydrate (8.0 g, 39.8 millimols), 6N-hydrochloric acid and a mixed solvent of toluene/ethanol (1/1) (50 ml), followed by heating the mixture under reflux for 20 hours, and treating it in the same manner as in Example 2 except that toluene as an effluent was made heptane, to obtain raw (E)-(trans-4-(trans-4-(4-fluorobutenyl)cyclohexyl)cyclohexyl)-4-ethylbenzene (9.1 g). This product was recrystallized from a mixed solvent of ethyl acetate/heptane (2/8), to obtain the captioned compound (1.8 g, yield: 17.5%).

The following compounds (No. 205 to No. 231) were prepared according to the process of Example 7:
No.
205. (E)-(trans-4-(trans-4-(4-fluorobutenyl)cyclohexyl)cyclohexyl)-4-propylbenzene
206. (E)-(trans-4-(trans-4-(4-fluorobutenyl)cyclohexyl)cyclohexyl)-4-butylbenzene
207. (E)-(trans-4-(4-fluorobutenyl)cyclohexyl)-4-(trans-4-propylcyclohexyl)benzene
  Cr room temperature or lower $S_B$159.5–159.6N 176.1–176.2 $I_{so}$
208. (E)-(trans-4-(trans-4-(4-fluorobutenyl)cyclohexyl)cyclohexyl)-4-heptylbenzene
209. (E)-(trans-4-(trans-4-(4-fluorobutenyl)cyclohexyl)cyclohexyl)-4-ethoxybenzene
210. (E)-(trans-4-(trans-4-(4-fluorobutenyl)cyclohexyl)cyclohexyl)-4-pentyloxybenzene
211. (E)-(trans-4-(trans-4-(4-fluorobutenyl)cyclohexyl)cyclohexyl)-4-methoxymethylbenzene
212. (E)-4-(trans-4-(4-fluorobutenyl)cyclohexyl)-4'-(trans-4-butylcyclohexyl)biphenyl
  Cr 210.4–210.9N 241.2–243.3 $I_{so}$
213. (E)-(trans-4-(trans-4-(5-fluoropentenyl)cyclohexyl)cyclohexyl)-4-ethylbenzene
214. (E)-(trans-4-(trans-4-(5-fluoropentenyl)cyclohexyl)cyclohexyl)-4-ethoxybenzene
215. (E)-(trans-4-(trans-4-(5-fluoropentenyl)cyclohexyl)cyclohexyl)-4-methoxymethylbenzene
216. (E)-(trans-4-(trans-4-(5-fluoro-3-pentenyl)cyclohexyl)cyclohexyl)-4-propylbenzene
217. (E)-(trans-4-(trans-4-(5-fluoro-3-pentenyl)cyclohexyl)cyclohexyl)-4-heptylbenzene
218. (E)-(trans-4-(trans-4-(6-fluoro-2-hexenyl)cyclohexyl)cyclohexyl)-4-ethylbenzene
219. (E)-(trans-4-(trans-4-(6-fluoro-3-hexenyl)cyclohexyl)cyclohexyl)-4-propoxybenzene
220. (E)-(trans-4-(trans-4-(7-fluoroheptenyl)cyclohexyl)cyclohexyl)-4-methylbenzene
221. (E)-(trans-4-(trans-4-(7-fluoro-4-heptenyl)cyclohexyl)cyclohexyl)-4-ethoxybenzene
222. (E)-(trans-4-(2-(trans-4-(4-fluorobutenyl)cyclohexyl)ethyl)cyclohexyl)-4-propylbenzene
223. (E)-(trans-4-(2-(trans-4-(4-fluorobutenyl)cyclohexyl)ethyl)cyclohexyl)-4-pentylbenzene
224. (E)-(trans-4-(2-(trans-4-(4-fluorobutenyl)cyclohexyl)ethyl)cyclohexyl)-4-heptylbenzene
225. (E)-(trans-4-(2-(trans-4-(5-fluoropentenyl)cyclohexyl)ethyl)cyclohexyl)-4-ethylbenzene
226. (E)-(trans-4-(2-(trans-4-(5-fluoro-2-pentenyl)cyclohexyl)ethyl)cyclohexyl)-4-propoxybenzene
227. (E)-(trans-4-(2-(trans-4-(6-fluorohexenyl)cyclohexyl)ethyl)cyclohexyl)-4-methoxypropylbenzene
228. (E)-(trans-4-(2-(trans-4-(6-fluoro-3-hexenyl)cyclohexyl)ethyl)cyclohexyl)-4-methoxymethylbenzene
229. (E)-(trans-4-(2-(trans-4-(7-fluoro-2-heptenyl)cyclohexyl)ethyl)cyclohexyl)-4-butylbenzene
230. (E)-(trans-4-(2-(trans-4-(7-fluoro-3-heptenyl)cyclohexyl)ethyl)cyclohexyl)-4-pentylbenzene
231. (E)-(trans-4-(2-(trans-4-(7-fluoro-4-heptenyl)cyclohexyl)ethyl)cyclohexyl)-4-methylbenzene

Example 8

Preparation of (E)-4-(2-(trans-4-(4-fluorobutenyl)cyclohexyl)ethyl)benzonitrile (a compound of No. 232 of the formula (1) wherein Q represents $CFH_2$; l represents 1; l, m and o each represents 0; $A_3$ represents trans-1,4-cyclohexylene group; ring B represents 1,4-phenylene group; $Z_3$ represents —$(CH_2)_2$—; $L_1$ and $L_2$ both represent H; and $L_3$ represents CN)

A mixture of (3-fluoropropyl)triphenylphosphonium bromide (14.7 g, 36.5 millimols) with THF (60 ml) was cooled down to $-20°$ C., followed by adding t-BuOK (4.1 g, 36.5 millimols) to the mixture, stirring for one hour, dropwise adding to the mixture, a THF (50 ml) solution of trans-4-(2-(4-cyanophenyl)ethyl)cyclohexanecarbaldehyde (9.0 g, 30.2 millimols so as to keep the temperature at $-20°$ C. or lower, stirring the mixture at the same temperature for 2 hours, and treating the product in the same manner as in Example 1 except that the quantity used for extraction was made 200 ml, to obtain raw 4-(2-(trans-4-(4-fluorobutenyl)cyclohexyl)ethyl)benzonitrile (8.1 g).

This raw product (8.1 g, 28.4 millimols) was mixed with sodium benzenesulfinate dihydrate (8.5 g, 42.6 millimols), 6N-hydrochloric acid (7.1 ml, 42.6 millimols), and ethanol (30 ml), followed by heating the mixture under reflux for 12 hours, and treating the product in the same manner as in Example 1 except that the quantity of ethyl acetate used for extraction was made 150 ml, to obtain raw (E)-4-(2-trans- 4-(4-fluorobutenyl)cyclohexyl)ethyl-benzonitrile (7.8 g). This product was recrystallized from ethanol, to obtain the captioned compound (1.3 g, yield: 13.7%).

The following compounds (No. 233 to No. 259) were prepared according to the process of Example 8:
No.
233. (E)-(2-trans-4-(4-fluorobutenyl)cyclohexyl)ethyl)-4-fluorobenzene
234. (E)-(2-trans-4-(4-fluorobutenyl)cyclohexyl)ethyl)-4-difluoromethylbenzene
235. (E)-(2-trans-4-(4-fluorobutenyl)cyclohexyl)ethyl)-4-trifluoromethoxybenzene
236. (E)-(2-(trans-4-(4-fluorobutenyl)cyclohexyl)ethyl)-3,4-difluorobenzene
237. (E)-(2-(trans-4-(4-fluorobutenyl)cyclohexyl)ethyl)-3-fluoro-4-difluoromethylbenzene
238. (E)-(2-(trans-4-(4-fluorobutenyl)cyclohexyl)ethyl)-3-fluoro-4-trifluoromethoxybenzene
239. (E)-4-(2-(trans-4-(4-fluorobutenyl)cyclohexyl)ethyl)-2-fluorobenzonitrile
240. (E)-(2-(trans-4-(4-fluorobutenyl)cyclohexyl)ethyl)-3,4,5-trifluorobenzene
241. (E)-(2-(trans-4-(4-fluorobutenyl)cyclohexyl)ethyl)-3,5-difluoro-4-trifluoromethylbenzene
242. (E)-(2-(trans-4-(4-fluorobutenyl)cyclohexyl)ethyl)-3,5-difluoro-4-difluoromethoxybenzene
243. (E)-(2-(trans-4-(4-fluorobutenyl)cyclohexyl)ethyl)-4-propylbenzene
244. (E)-(2-(trans-4-(4-fluorobutenyl)cyclohexyl)ethyl)-4-heptylbenzene
245. (E)-4-(2-trans-4-(5-fluoropentenyl)cyclohexyl)ethyl)benzonitrile
246. (E)-(2-(trans-4-(5-fluoropentenyl)cyclohexyl)ethyl)-4-difluoromethoxybenzene
247. (E)-(2-(trans-4-(5-fluoropentenyl)cyclohexyl)ethyl)-3,4,5-trifluorobenzene
248. (E)-(2-(trans-4-(5-fluoropentenyl)cyclohexyl)ethyl)-3,5-difluoro-4-trifluoromethoxybenzene
249. (E)-(2-(trans-4-(5-fluoropentenyl)cyclohexyl)ethyl)-4-ethylbenzene
250. (E)-4-(2-(trans-4-(5-fluoro-3-pentenyl)cyclohexyl)ethyl)benzonitrile
251. (E)-(2-(trans-4-(5-fluoro-3-pentenyl)cyclohexyl)ethyl)-3,4,5-trifluorobenzene
252. (E)-4-(2-trans-4-(6-fluorohexenyl)cyclohexyl)ethyl)benzonitrile
253. (E)-(2-(trans-4-(6-fluorohexenyl)cyclohexyl)ethyl)-3,5-difluoro-4-difluoromethylbenzene
254. (E)-(2-(trans-4-(6-fluorohexenyl)cyclohexyl)ethyl)-4-propoxybenzene
255. (E)-4-(2-(trans-4-(6-fluoro-2-hexenyl)cyclohexyl)ethyl)benzonitrile
256. (E)-4-(2-(trans-4-(7-fluoroheptenyl)cyclohexyl)ethyl)benzonitrile
257. (E)-(2-trans-4-(7-fluoroheptenyl)cyclohexyl)ethyl)-3-fluoro-4-fluoromethylbenzene
258. (E)-(2-(trans-4-(7-fluoroheptenyl)cyclohexyl)ethyl)-4-butylbenzene
259. (E)-4-(2-(trans-4-(7-fluoro-4-heptenyl)cyclohexyl)ethyl)benzonitrile Example 9

Preparation of (E)-4-(2-(trans-4-(trans-4-(4-fluorobutenyl)cyclohexyl)cyclohexyl)ethyl)benzonitrile (a compound No. 260 of the formula (1) wherein Q represents $CFH_2$; l represents 1; 1, m and o each represent 0; p represents 1; $A_2$ and $A_3$ both represent trans-1,4-cyclohexylene group; ring B represents 1,4-phenylene group; $Z_2$ represents covalent bond; $Z_3$ represents —$(CH_2)_2$—; $L_1$ and $L_2$ both represent H; and $L_3$ represents CN.

A mixture of (3-fluoropropyl)triphenylphosphonium bromide (15.1 g, 37.4 millimols) with THF (70 ml) was cooled down to −20° C., followed by adding t-BuOK (4.2 g, 37.4 millimols) to the mixture, stirring for one hour, dropwise adding to the mixture, a THF (100 ml) solution of trans-4-(trans-4-(2-(4-cyanophenyl)ethyl)cyclohexyl)cyclohexanecarbaldehyde (11.0 g, 34.0 millimols) so as to keep the temperature at −20° C. or lower, stirring the mixture at the same temperature for 2 hours, and treating the reaction product in the same manner as in Example 2, except that the quantity of ethyl acetate was made 500 ml, to obtain raw 4-(2-(trans-4-(trans-4-(4-fluorobutenyl)cyclohexyl)cyclohexyl)ethyl)benzonitrile (11.3 g).

This raw product (11.3 g, 30.7 millimols) was mixed with sodium benzenesulfinate dihydrate (9.2 g, 46.1 millimols), 6N-hydrochloric acid (7.7 ml, 46.1 millimols) and a mixed solvent of toluene/ethanol (1/1) (70 ml), followed by heating the mixture under reflux for 16 hours, and treating the reaction product in the same manner as in Example 2, to obtain raw (E)-4-(2-(trans-4-(trans-4-(4-fluorobutenyl)cyclohexyl)cyclohexyl)ethyl)benzonitrile (11.0 g). This product was recrystallized from a mixed solvent of ethyl acetate/heptane (2/8), to obtain the captioned compound (4.8 g, yield: 38.4%).

Cr 105.9–106.6N 197.2–198.0 $I_{so}$

The following compounds (No. 261 to No. 295) were prepared according to the process of Example 9:
No.
261. (E)-(2-(trans-4-(trans-4-(4-fluorobutenyl)cyclohexyl)cyclohexyl)ethyl)-4-fluorobenzene
262. (E)-(2-(trans-4-(trans-4-(4-fluorobutenyl)cyclohexyl)cyclohexyl)ethyl)-4-chlorobenzene
263. (E)-(2-(trans-4-(trans-4-(4-fluorobutenyl)cyclohexyl)cyclohexyl)ethyl)-4-bromobenzene
264. (E)-(2-(trans-4-(trans-4-(4-fluorobutenyl)cyclohexyl)cyclohexyl)ethyl)-4-trifluoromethylbenzene
265. (E)-(2-(trans-4-(trans-4-(4-fluorobutenyl)cyclohexyl)cyclohexyl)ethyl)-4-difluoromethoxybenzene
266. (E)-(2-(trans-4-(trans-4-(4-fluorobutenyl)cyclohexyl)cyclohexyl)ethyl)-3,4-difluorobenzene
267. (E)-(2-(trans-4-(trans-4-(4-fluorobutenyl)cyclohexyl)cyclohexyl)ethyl)-3-fluoro-4-chlorobenzene
268. (E)-4-(2-(trans-4-(trans-4-(4-fluorobutenyl)cyclohexyl)cyclohexyl)ethyl)-2-fluorobenzonitrile
269. (E)-(2-(trans-4-(trans-4-(4-fluorobutenyl)cyclohexyl)cyclohexyl)ethyl)-3-fluoro-4-fluoromethylbenzene
270. (E)-(2-(trans-4-(trans-4-(4-fluorobutenyl)cyclohexyl)cyclohexyl)ethyl)-3-fluoro-4-trifluoromethylbenzene
271. (E)-(2-(trans-4-(trans-4-(4-fluorobutenyl)cyclohexyl)cyclohexyl)ethyl)-3-fluoro-4-trifluoromethoxybenzene
272. (E)-(2-trans-4-(trans-4-(4-fluorobutenyl)cyclohexyl)cyclohexyl)ethyl)-3,4,5-trifluorobenzene
273. (E)-(2-trans-4-(trans-4-(4-fluorobutenyl)cyclohexyl)cyclohexyl)ethyl)-3,5-difluoro-4-chlorobenzene
274. (E)-4-(2-(trans-4-(trans-4-(4-fluorobutenyl)cyclohexyl)cyclohexyl)ethyl)-2,6-difluorobenzonitrile
275. (E)-(2-(trans-4-(trans-4-(4-fluorobutenyl)cyclohexyl)cyclohexyl)ethyl)-3,5-difluoro-4-difluoromethylbenzene
276. (E)-(2-(trans-4-(trans-4-(4-fluorobutenyl)cyclohexyl)cyclohexyl)ethyl)-3,5-difluoro-4-trifluoromethylbenzene
277. (E)-(2-(trans-4-(trans-4-(4-fluorobutenyl)cyclohexyl)cyclohexyl)ethyl)-3,5-difluoro-4-trifluoromethoxybenzene
278. (E)-(2-(trans-4-(trans-4-(4-fluorobutenyl)cyclohexyl)cyclohexyl)ethyl)-4-propylbenzene 279. (E)-(2-(trans-4-(trans-4-(4-fluorobutenyl)cyclohexyl)cyclohexyl)ethyl)-4-propoxymethylbenzene
280. (E)-(2-(trans-4-(trans-4-(4-fluorobutenyl)cyclohexyl)cyclohexyl)ethyl)-4-pentylbenzene
281. (E)-(2-(trans-4-(trans-4-(4-fluorobutenyl)cyclohexyl)cyclohexyl)ethyl)-4-hexyloxybenzene
282. (E)-4-(2-(trans-4-(trans-4-(5-fluoropentenyl)cyclohexyl)cyclohexyl)ethyl)benzonitrile
283. (E)-(2-trans-4-(trans-4-(5-fluoropentenyl)cyclohexyl)cyclohexyl)ethyl)-4-fluoromethylbenzene
284. (E)-(2-(trans-4-(trans-4-(5-fluoropentenyl)cyclohexyl)cyclohexyl)ethyl)-3-fluoro-4-difluoromethoxybenzene
285. (E)-(2-(trans-4-(trans-4-(5-fluoropentenyl)cyclohexyl)cyclohexyl)ethyl)-3,4,5-trifluorobenzene
286. (E)-(2-trans-4-(trans-4-(5-fluoropentenyl)cyclohexyl)cyclohexyl)ethyl)-3,5-difluoro-4-trifluoromethylbenzene
287. (E)-(2-trans-4-(trans-4-(5-fluoropentenyl)cyclohexyl)cyclohexyl)ethyl)-4-ethylbenzene
288. (E)-(2-trans-4-(trans-4-(5-fluoro-3-pentenyl)cyclohexyl)cyclohexyl)ethyl)-3,4-difluorobenzene
289. (E)-(2-(trans-4-(trans-4-(5-fluoro-3-pentenyl)cyclohexyl)cyclohexyl)ethyl)-3,5-difluoro-4-trifluoromethylbenzene
290. (E)-4-(2-trans-4-(trans-4-(6-fluoro-2-hexenyl)cyclohexyl)cyclohexyl)ethyl)benzonitrile
291. (E)-(2-(trans-4-(trans-4-(6-fluoro-3-hexenyl)cyclohexyl)cyclohexyl)ethyl)-4-fluorobenzene
292. (E)-(2-(trans-4-(trans-4-(6-fluoro-3-hexenyl)cyclohexyl)cyclohexyl)ethyl)-3,5-difluoro-4-trifluoromethylbenzene
293. (E)-4-(2-(trans-4-(trans-4-(7-fluoroheptenyl)cyclohexyl)cyclohexyl)ethyl)benzonitrile
294. (E)-(2-(trans-4-(trans-4-(7-fluoroheptenyl)cyclohexyl)cyclohexyl)ethyl)-3,5-difluoromethoxybenzene
295. (E)-(2-(trans-4-(trans-4-(7-fluoro-4-heptenyl)cyclohexyl)cyclohexyl)ethyl)-4-methylbenzene

Example 10

Preparation of (E)-4-(trans-4-(4,4,4-trifluorobutenyl)cyclohexyl)benzonitrile (a compound of No. 296 of the formula (1) wherein Q represents $CF_3$; Z represents 1; m, o and p all represent 0; $A_3$ represents trans-1,4-cyclohexylene group; ring B represents 1,4-phenylene group; $Z_3$ represent covalent bond; $L_1$ and $L_2$ both represent H; and $L_3$ represents CN.

A mixture of (3,3,3-trifluoropropyl)triphenylphosphonium bromide (9.0 g, 20.5 millimols) with THF (45 ml) was cooled down to −20° C., followed by adding t-BuOK (2.5 g, 22.5 millimols) to the mixture, stirring for 30 minutes, dropwise adding to the mixture, a THF (50 ml) solution of trans-4-(4-cyanophenyl)cyclohexanecarbaldehyde (4.8 g, 22.5 millimols) so as to keep the temperature at −20° C. or lower, stirring the mixture at the same temperature for 2 hours, and treating the product in the same manner as in Example 1, to obtain raw 4-(trans-4-(4,4,4-trifluorobutenyl)cyclohexyl)benzonitrile (5.1 g).

This raw product (5.1 g, 18.4 millimols) was mixed with sodium benzenesulfinate dihydride (5.5 g, 27.6 millimols), 6N-hydrochloric acid (4.6 ml, 27.6 millimols) and ethanol (30 ml), followed by heating the mixture under reflux for 12 hours, and treating the reaction product in the same manner as in Example 1, to obtain raw (E)-4-(trans-4-(4,4,4-trifluorobutenyl)cyclohexyl)benzonitrile (4.9 g). This product was recrystallized from ethanol, to obtain the captioned compound (0.8 g, yield: 13.9%).

Cr 45.3–46.1 $I_{so}$

The following compounds (No. 297 to No. 323) were prepared according to the process of Example 10:

297. (E)-(trans-4-(4,4,4-trifluorobutenyl)cyclohexyl)-4-bromobenzene
298. (E)-(trans-4-(4,4,4-trifluorobutenyl)cyclohexyl)-4-fluoromethylbenzene
299. (E)-(trans-4-(4,4,4-trifluorobutenyl)cyclohexyl)-3,4-difluorobenzene
300. (E)-(trans-4-(4,4,4-trifluorobutenyl)cyclohexyl)-3-fluoro-4-chlorobenzene
301. (E)-4-(trans-4-(4,4,4-trifluorobutenyl)cyclohexyl)-2-fluorobenzonitrile
302. (E)-(trans-4-(4,4,4-trifluorobutenyl)cyclohexyl)-3-fluoro-4-difluoromethylbenzene
303. (E)-(trans-4-(4,4,4-trifluorobutenyl)cyclohexyl)-3,4,5-trifluorobenzene
304. (E)-(trans-4-(4,4,4-trifluorobutenyl)cyclohexyl)-3,5-difluoro-4-chlorobenzene
305. (E)-(trans-4-(4,4,4-trifluorobutenyl)cyclohexyl)-3,5-difluoro-4-difluoromethylbenzene
306. (E)-(trans-4-(4,4,4-trifluorobutenyl)cyclohexyl)-3,5-difluoro-4-trifluoromethylbenzene
307. (E)-(trans-4-(4,4,4-trifluorobutenyl)cyclohexyl)-3,5-difluoro-4-trifluoromethoxybenzene
308. (E)-(trans-4-(4,4,4-trifluorobutenyl)cyclohexyl)-4-propylbenzene
309. (E)-(trans-4-(4,4,4-trifluorobutenyl)cyclohexyl)-4-propoxymethylbenzene
310. (E)-(trans-4-(4,4,4-trifluorobutenyl)cyclohexyl)-4-heptylbenzene
311. (E)-(trans-4-(5,5,5-trifluoropentenyl)cyclohexyl)-4-difluoromethoxybenzene
312. (E)-4-(trans-4-(5,5,5-trifluoropentenyl)cyclohexyl)benzonitrile
  Cr 47.7–48.7 (N 17.5) $I_{so}$
313. (E)-(trans-4-(5,5,5-trifluoropentenyl)cyclohexyl)-3,4,5-trifluorobenzene
314. (E)-(trans-4-(5,5,5-trifluoropentenyl)cyclohexyl)-3,5-difluoro-4-trifluoromethylbenzene
315. (E)-(trans-4-(5,5,5-trifluoro-2-pentenyl)cyclohexyl)-4-butylbenzene
316. (E)-4-(trans-4-(5,5,5-trifluoro-3-pentenyl)cyclohexyl)-2-fluorobenzonitrile
317. (E)-(trans-4-(5,5,5-trifluoro-3-pentenyl)cyclohexyl)-3,5-difluoro-4-difluoromethoxybenzene
318. (E)-(trans-4-(6,6,6-trifluoro-2-hexenyl)cyclohexyl)-3,5-difluoro-4-trifluoromethylbenzene
319. (E)-(trans-4-(6,6,6-trifluoro-3-hexenyl)cyclohexyl)-3-fluoro-4-chlorobenzene
320. (E)-(trans-4-(6,6,6-trifluoro-3-hexenyl)cyclohexyl)-3,5-difluoro-4-fluoromethylbenzene
321. (E)-4-(trans-4-(7,7,7-trifluoro-3-heptenyl)cyclohexyl)benzonitrile
  Cr 48.4–49.7 (N 28.5) $I_{so}$
322. (E)-(trans-4-(7,7,7-trifluoro-3-heptenyl)cyclohexyl)-3,5-difluoro-4-trifluoromethoxybenzene
323. (E)-(trans-4-(7,7,7-trifluoro-4-heptenyl)cyclohexyl)-4-ethylbenzene

Example 11

Preparation of (E)-4-(trans-4-(4,4-difluorobutenyl)cyclohexyl)benzonitrile (a compound of No. 324 of the formula (1), wherein Q represents $CF_2H$; l represents 1, m, o and p each represent 0; $A_3$ represents trans-1,4-cyclohexylene group; ring B represents 1,4-phenylene group; $Z_3$ represents covalent bond; $L_1$ and $L_2$ both represent H; and $L_3$ represents CN.

A mixture of (2-(1,3-dioxan-2-yl)ethyl) triphenylphosphonium bromide (17.4 g, 38.0 millimols) with THF (100 ml) was cooled down to −20° C., followed by adding t-BuOK (4.5 g, 39.9 millimols) to the mixture, stirring for 30 minutes, dropwise adding to the mixture, a THF (35 ml) solution of trans-4-(4-cyanophenyl) cyclohexanecarbaldehyde (7.7 g, 36.1 millimols) so as to keep the temperature at −20° C. or lower, stirring the mixture at the same temperature for 2 hours, and treating the reaction product in the same manner as in Example 3, to obtain raw 4-(trans-4-(3-(1,3-dioxan-2-yl) propenyl) cyclohexyl)benzonitrile (10.3 g).

This raw product (10.3 g, 33.2 millimols) was mixed with 6N-hydrochloric acid (11.1 ml, 66.4 millimols) and toluene (50 ml), followed by heating the mixture under reflux for 6 hours, and treating the reaction product in the same manner as in Example 3 except that toluene used for eluent was made ethyl acetate (150 ml), to obtain raw 4-(trans-4-(3-formylpropenyl)cyclohexyl)benzonitrile (7.2 g).

The thus obtained raw product (7.2 g, 28.4 millimols) was further mixed with DAST (13.8 g, 85.3 millimols) and dichloromethane (35 ml), followed by stirring the mixture at room temperature for 24 hours, pouring the reaction product in ice water (150 ml), extracting it with ethyl acetate (150 ml), washing the resulting organic layer once with a saturated potassium carbonate aqueous solution, and twice with water, drying over anhydrous magnesium sulfate, distilling off the solvent under reduced pressure and subjecting the residue to silica gel column chromatography (eluent: toluene), to obtain raw 4-(trans-4-(4,4-difluorobutenyl) cyclohexyl)benzonitrile (3.7 g), mixing this raw product (3.7 g, 13.8 millimols) with sodium benzenesulfinate dihydrate (4.2 g, 20.8 millimols), 6N-hydrochloric acid (3.5 ml, 20.8 millimols) and ethanol (20 ml), heating the mixture under reflux for 12 hours, adding water (100 ml) to the reaction product after completion of the reaction, extracting the mixture with ethyl acetate (200 ml), washing the resulting organic layer three times with a saturated sodium carbonate aqueous solution and three times with water, drying over anhydrous sodium sulfate, distilling off the solvent under reduced pressure and subjecting the residue to silica gel column chromatography (eluent: toluene), to obtain raw (E)-4-(trans-4-(4,4-difluorobutenyl)cyclohexyl)benzonitrile (3.8 g). This product was recrystallized from ethanol, to obtain the captioned compound (1.3 g, yield: 12.7%).

The following compounds (No. 325 to No. 350) were prepared according to the process of Example 11:
No.
325. (E)-(trans-4-(3,3-difluoropropenyl)cyclohexyl)-3,4,5-trifluorobenzene
  Cr 3.7 I$_{so}$
326. (E)-(trans-4-(3,3-difluoropropenyl)cyclohexyl)-4-propylbenzene
  Cr 35.3–37.2 I$_{so}$
327. (E)-(trans-4-(4,4-difluorobutenyl)cyclohexyl)-4-difluoromethylbenzene
328. (E)-(trans-4-(4,4-difluorobutenyl)cyclohexyl)-4-trifluoromethoxybenzene
329. (E)-(trans-4-(4,4-difluorobutenyl)cyclohexyl)-4-propylbenzene
330. (E)-(trans-4-(4,4-difluorobutenyl)cyclohexyl)-4-propoxymethylbenzene
331. (E)-(trans-4-(4,4-difluorobutenyl)cyclohexyl)-4-heptylbenzene
332. (E)-(trans-4-(4,4-difluorobutenyl)cyclohexyl)-3,4-difluorobenzene
333. (E)-(trans-4-(4,4-difluorobutenyl)cyclohexyl)-3-fluoro-4-chlorobenzene
334. (E)-4-(trans-4-(4,4-difluorobutenyl)cyclohexyl)-2-fluorobenzonitrile
335. (E)-(trans-4-(4,4-difluorobutenyl)cyclohexyl)-3-fluoro-4-fluoromethylbenzene
336. (E)-(trans-4-(4,4-difluorobutenyl)cyclohexyl)-3-fluoro-4-trifluoromethylbenzene
337. (E)-(trans-4-(4,4-difluorobutenyl)cyclohexyl)-3-fluoro-4-trifluoromethoxybenzene
338. (E)-(trans-4-(4,4-difluorobutenyl)cyclohexyl)-3,5-difluoro-4-trifluoromethylbenzene
339. (E)-(trans-4-(4,4-difluorobutenyl)cyclohexyl)-3,5-difluoro-4-difluoromethoxybenzene
340. (E)-(trans-4-(4,4-difluorobutenyl)cyclohexyl)-3,4,5-trifluorobenzene
341. (E)-4-(trans-4-(5,5-difluoropentenyl)cyclohexyl)benzonitrile
342. (E)-(trans-4-(5,5-difluoropentenyl)cyclohexyl)-4-trifluoromethoxybenzene
343. (E)-(trans-4-(5,5-difluoropentenyl)cyclohexyl)-3-fluoro-4-trifluoromethylbenzene
344. (E)-(trans-4-(5,5-difluoropentenyl)cyclohexyl)-3-fluoro-4-difluoromethoxybenzene
345. (E)-4-(trans-4-(5,5-difluoro-3-pentenyl)cyclohexyl)benzonitrile
346. (E)-(trans-4-(5,5-difluoro-3-pentenyl)cyclohexyl)-4-trifluoromethylbenzene
347. (E)-(trans-4-(5,5-difluoro-3-pentenyl)cyclohexyl)-4-difluoromethoxybenzene
348. (E)-4-(trans-4-(6,6-difluoro-2-hexenyl)cyclohexyl)benzonitrile
349. (E)-4-(trans-4-(7,7-difluoro-4-heptenyl)cyclohexyl)benzonitrile
350. (E)-(trans-4-(7,7-difluoro-4-heptenyl)cyclohexyl)-4-ethylbenzene

Example 12

Preparation of (E)-4-(trans-4-(trans-4-(4,4-difluorobutenyl)cyclohexyl)cyclohexyl)benzonitrile (a compound No. 351 of the formula (1) wherein Q represents $CF_2H$; l represents 1; m and o both represent 0; p represents 1; $A_2$ and $A_3$ both represent trans-1,4-cyclohexylene group; ring B represents 1,4-phenylene group; $Z_3$ represents covalent bond; $L_1$ and $L_2$ both represent H and $L_3$ represents CN.

A mixture of (2-(1,3-dioxan-2-yl)ethyl) triphenylphosphonium bromide (25.0 g, 54.7 millimols) with THF (150 ml) was cooled down to −20° C., followed by adding t-BuOK (6.1 g, 54.7 millimols) to the mixture, stirring for 30 minutes, dropwise adding to the mixture, a THF (80 ml) solution of trans-4-(trans-4-(4-cyanophenyl)cyclohexyl)cyclohexanecarbaldehyde (14.4 g, 49.8 millimols) so as to keep the temperature at −20° C. or lower, stirring the mixture at the same temperature for 2 hours, and treating the reaction product in the same manner as in Example 2, except that the quantity of ethyl acetate used for extraction was made 400 ml, to obtain raw 4-(trans-4-(trans-4-(3-(1,3-dioxan-2-yl)propenyl)cyclohexyl)cyclohexyl) benzonitrile (17.5 g).

This raw product (17.5 g, 44.5 millimols) was mixed with 6N-hydrochloric acid (14.8 ml, 88.9 millimols) and toluene (80 ml), followed by heating the mixture under reflux for 5 hours, and treating the product in the same manner as in Example 2 except that the quantity of water added to the reaction product was made 150 ml and the quantity of ethyl acetate used for the extraction was made 150 ml, to obtain raw 4-(trans-4-(trans-4-(3-formylpropenyl)cyclohexyl) cyclohexyl)benzonitrile (12.9 g).

The thus obtained raw product (12.9 g, 38.5 millimols) was further mixed with DAST (18.6 g, 115.5 millimols) and dichloromethane (60 ml), followed by stirring the mixture at room temperature for 24 hours, pouring the reaction product in ice water (200 ml), extracting with ethyl acetate (300 ml), washing the resulting organic layer once with a saturated potassium carbonate aqueous solution and twice with water, drying over anhydrous magnesium sulfate, distilling off the solvent under reduced pressure and subjecting the residue to silica gel column chromatography (eluent: toluene), to obtain raw 4-(trans-4-trans-4-(4,4-difluorobutenyl) cyclohexyl)cyclohexyl)benzonitrile (5.3 g). This raw product (5.3 g, 14.8 millimols) was mixed with sodium benzenesulfinate dihydrate (4.5 g, 22.2 millimols), 6N-hydrochloric acid (3.7 ml, 22.2 millimols) and a mixed solvent of toluene/ethanol (1/1) (40 ml), followed by refluxing the mixture for 12 hours, adding water (100 ml) to the reaction product, extracting with ethyl acetate (200 ml), washing the resulting organic layer three times with a saturated sodium carbonate aqueous solution and three times with water, drying over anhydrous sodium sulfate, distilling off the solvent under reduced pressure and subjecting the residue to silica gel column chromatography (effluent: toluene), to obtain raw (E)-4-(trans-4-(trans-4-(4,4-difluorobutenyl)cyclohexyl)cyclohexyl)benzonitrile (3.8 g). This product was recrystallized from a mixed solvent of ethyl acetate/heptane (3/7), to obtain the captioned compound (1.8 g, yield: 10.3%).

The following compounds (No. 352 to No. 372) were prepared according to the process of Example 12:
No.
352. (E)-(trans-4-(trans-4-(4,4-difluorobutenyl)cyclohexyl) cyclohexyl)-4-bromobenzene
353. (E)-(trans-4-(trans-4-(4,4-difluorobutenyl)cyclohexyl) cyclohexyl)-4-difluoromethylbenzene
354. (E)-(trans-4-(trans-4-(4,4-difluorobutenyl)cyclohexyl) cyclohexyl)-4-trifluoromethoxybenzene
355. (E)-(trans-4-(trans-4-(4,4-difluorobutenyl)cyclohexyl) cyclohexyl)-3-fluoro-4-chlorobenzene
356. (E)-(trans-4-(trans-4-(4,4-difluorobutenyl)cyclohexyl) cyclohexyl)-2-fluorobenzonitrile
357. (E)-(trans-4-(trans-4-(4,4-difluorobutenyl)cyclohexyl) cyclohexyl)-3-fluoro-4-difluoromethoxybenzene
358. (E)-(trans-4-(trans-4-(4,4-difluorobutenyl)cyclohexyl) cyclohexyl)-3,4,5-trifluorobenzene
359. (E)-(trans-4-(trans-4-(4,4-difluorobutenyl)cyclohexyl) cyclohexyl)-4-propylbenzene
360. (E)-(trans-4-(trans-4-(4,4-difluorobutenyl)cyclohexyl) cyclohexyl)-4-methoxypentylbenzene
361. (E)-(trans-4-(trans-4-(4,4-difluorobutenyl)cyclohexyl) cyclohexyl)-3,5-difluoro-4-trifluoromethylbenzene
362. (E)-(trans-4-(trans-4-(4,4-difluorobutenyl)cyclohexyl) cyclohexyl)-3,5-difluoro-4-difluoromethoxybenzene
363. (E)-(trans-4-(trans-4-(5,5-difluoropentenyl) cyclohexyl)cyclohexyl)-3-fluoro-4-difluoromethylbenzene
364. (E)-(trans-4-(trans-4-(5,5-difluoropentenyl) cyclohexyl)cylcohexyl)-3,4,5-trifluorobenzene
365. (E)-(trans-4-(trans-4-(5,5-difluoropentenyl) cyclohexyl)cyclohexyl)-3,5-difluoro-4-trifluoromethylbenzene
366. (E)-(trans-4-(trans-4-(5,5-difluoro-3-pentenyl) cyclohexyl)cyclohexyl)-4-fluoromethylbenzene
367. (E)-(trans-4-(trans-4-(5,5-difluoro-3-pentenyl) cyclohexyl)cyclohexyl)-4-butylbenzene
368. (E)-(trans-4-(trans-4-(6,6-difluoro-2-hexenyl) cyclohexyl)cyclohexenyl)-3,5-difluoro-4-trifluoromethoxybenzene
369. (E)-(trans-4-(trans-4-(6,6-difluoro-3-hexenyl) cyclohexyl)cyclohexyl)-4-methoxymethylbenzene
370. (E)-(trans-4-(trans-4-(7,7-difluoro-3-heptenyl) cyclohexyl)cyclohexyl)-4-difluoromethoxybenzene
371. (E)-(trans-4-(trans-4-(7,7-difluoro-3-heptenyl) cyclohexyl)cyclohexyl)-3,4-difluorobenzene
372. (E)-(trans-4-(trans-4-(7,7-difluoro-4-heptenyl) cyclohexyl)cyclohexyl)-4-methylbenzene Example 13

Preparation of (E)-trans-(trans-4-(4-fluorobutenyl) cyclohexyl)-4-pentylcylohexane (a compound No. 373 of the formula (1), wherein Q represents $CFH_2$; l represents 1; m, o and p each represent 0; $A_3$ and ring B both represent trans-1,4-cyclohexylene group; $Z_3$ represents covalent bond; $L_1$ and $L_2$ both represent H; and $L_3$ represents $C_5H_{11}$.

A mixture of (3-fluoropropyl)triphenylphosphonium bromide (6.9 g, 17.1 millimols) with THF (40 ml) was cooled down to −20° C., followed by adding t-BuOK (1.9 g, 17.1 millimols) to the mixture, stirring the mixture for 30 minutes, dropwise adding to the mixture, a THF (30 ml) solution of trans-4-(trans-4-pentylcyclohexyl) cyclohexanecarbaldehyde (4.1 g, 15.5 millimols) so as to keep the temperature at −20° C., stirring the mixture at the same temperature for 2 hours, and treating the reaction product in the same manner as in Example 1, except that the quantity of ethyl acetate used for extraction was made 150 ml, to obtain raw trans-(trans-4-(4-fluorobutenyl) cyclohexyl)-4-pentylcyclohexane (4.2 g).

This raw product (4.2 g, 13.6 millimols) was mixed with sodium benzenesulfinate dihydrate (4.1 g, 20.4 millimols), 6N-hydrochloric acid (3.4 ml, 20.4 millimols) and ethanol (30 ml), followed by heating the mixture under reflux for 18 hours, and treating the reaction product in the same manner as in Example 1, except that the quantity of ethylacetate used for extraction was made 150 ml and toluene as eluent was made heptane, to obtain raw (E)-trans-(trans-4-(4-fluorobutenyl)cyclohexyl)-4-pentylcyclohexane (4.0 g). This product was recrystallized from ethanol to obtain the captioned compound (1.0 g, yield: 20.8%).

Cr room temperature or lower $S_B$ 108.5–108.8 $I_{so}$

The following compounds (No. 374 to No. 425) were prepared according to the process of Example 13:
No.
374. (E)-trans-(trans-4-(4-fluorobutenyl)cyclohexyl)-4-methylcyclohexane
375. (E)-trans-(trans-4-(4-fluorobutenyl)cyclohexyl)-4-ethylcyclohexane
376. (E)-trans-(trans-4-(4-fluorobutenyl)cyclohexyl)-4-propylcyclohexane
377. (E)-trans-(trans-4-(4-fluorobutenyl)cyclohexyl)-4-butylcyclohexane
378. (E)-trans-(trans-4-(4-fluorobutenyl)cyclohexyl)-4-nonylcyclohexane
379. (E)-trans-(trans-4-(4-fluorobutenyl)cyclohexyl)-4-hexylcyclohexane
380. (E)-trans-(trans-4-(4-fluorobutenyl)cyclohexyl)-4-heptylcyclohexane
381. (E)-trans-4-(trans-4-(4-fluorobutenyl)cyclohexyl) cyclohexanecarbonitrile
382. (E)-trans-(trans-4-(4-fluorobutenyl)cyclohexyl)-4-propoxycyclohexane
383. (E)-trans-(trans-4-(5-fluoropentenyl)cyclohexyl)-4-propylcyclohexane
384. (E)-trans-(trans-4-(5-fluoropentenyl)cyclohexyl)-4-pentylcyclohexane
385. (E)-trans-4-(trans-4-(5-fluoropentenyl)cyclohexyl) cyclohexanecarbonitrile 386. (E)-trans-(trans-4-(5-fluoro-3-pentenyl)cyclohexyl)-4-ethoxyethylcyclohexane 387. (E)-trans-(trans-4-(6-fluoro-2-hexenyl)cyclohexyl)-4-ethylcyclohexane 388. (E)-trans-(trans-4-(6-fluoro-3-hexenyl)cyclohexyl)-4-butylcyclohexane 389. (E)-trans-4-(trans-4-(6-fluoro-3-hexenyl)cyclohexenyl)cyclohexanecarbonitrile 390. (E)-trans-(trans-4-(7-fluoro-3-heptenyl)cyclohexyl)-4-ethylcyclohexane 391. (E)-trans-4-(trans-4-(7-fluoro-3-heptenyl)cyclohexyl)cyclohexanecarbonitrile 392. (E)-trans-(trans-4-(7-fluoro-4-heptenyl)cyclohexyl)-4-ethoxycyclohexane 393. (E)-trans-(2-(trans-4-(4-fluorobutenyl)cyclohexyl)ethyl)-4-propylcyclohexane
Cr room temperature or lower $S_B$ 88.9–89.2 $I_{so}$ 394. (E)-trans-(2-(trans-4-(4-fluorobutenyl)cyclohexyl)ethyl)-4-pentylcyclohexane 395. (E)-trans-4-(2-(trans-4-(4-fluorobutenyl)cyclohexyl)ethyl)cyclohexanecarbonitrile 396. (E)-trans-(2-trans-4-(5-fluoropentenyl)cyclohexyl)ethyl)-4-propylcyclohexane 397. (E)-trans-(2-(trans-4-(5-fluoropentenyl)cyclohexyl)ethyl)-4-butylcyclohexane 398. (E)-trans-(2-(trans-4-(5-fluoropentenyl)cyclohexyl)ethyl)-4-ethoxycyclohexane 399. (E)-trans-4-(2-(trans-4-(5-fluoropentenyl)cyclohexyl)ethyl)cyclohexanecarbonitrile 400. (E)-trans-(2-trans-4-(5-fluoro-3-pentenyl)cyclohexyl)ethyl)-4-propoxymethylcyclohexane 401. (E)-trans-(2-trans-4-(6-fluoro-2-hexenyl)cyclohexyl)ethyl)-4-methoxymethylcyclohexane 402. (E)-trans-(2-(trans-4-(6-fluoro-3-hexenyl)cyclohexyl)ethyl)-4-methoxyethylcyclohexane 403. (E)-trans-4-(2-(trans-4-(6-fluoro-3-hexenyl)cyclohexyl)ethyl)cyclohexanecarbonitrile 404. (E)-trans-(2-(trans-4-(7-fluoro-3-heptenyl)cyclohexenyl)ethyl)-4-methoxycyclohexane 405. (E)-trans-4-(2-(trans-4-(7-fluoro-3-heptenyl)cyclohexyl)ethyl)cyclohexanecarbonitrile 406. (E)-trans-4-(2-(trans-4-(7-fluoro-4-heptenyl)cyclohexyl)ethyl)-4-ethylcyclohexane 407. (E)-trans-(trans-4-(trans-4-(4-fluorobutenyl)cyclohexyl)cyclohexyl)-4-ethylcyclohexane 408. (E)-trans-(trans-4-(trans-4-(4-fluorobutenyl)cyclohexyl)cyclohexyl)-4-propylcyclohexane 409. (E)-trans-(trans-4-(trans-4-(4-fluorobutenyl)cyclohexyl)cyclohexyl)-4-butylcyclohexane 410. (E)-trans-(trans-4-(trans-4-(4-fluorobutenyl)cyclohexyl)cyclohexyl)-4-butoxycyclohexane 411. (E)-trans-(trans-4-(trans-4-(4-fluorobutenyl)cyclohexyl)cyclohexyl)-4-heptylcyclohexane 412. (E)-trans-4-(trans-4-(trans-4-(4-fluorobutenyl)cyclohexyl)cyclohexyl)cyclohexanecarbonitrile 413. (E)-trans-(trans-4-(trans-4-(5-fluoroheptenyl)cyclohexyl)cyclohexyl)-4-methoxymethylcyclohexane 414. (E)-trans-(trans-4-(trans-4-(5-fluoroheptenyl)cyclohexyl)cyclohexyl)-4-pentylcyclohexane 415. (E)-trans-4-(trans-4-(trans-4-(5-fluoroheptenyl)cyclohexyl)cyclohexyl)cyclohexanecarbonitrile 416. (E)-trans-(trans-4-(trans-4-(5-fluoro-3-heptenyl)cyclohexyl)cyclohexyl)-4-propoxycyclohexane 417. (E)-trans-4-(trans-4-(trans-4-(5-fluoro-3-heptenyl)cyclohexyl)cyclohexyl)cyclohexanecarbonitrile 418. (E)-trans-(trans-4-(trans-4-(6-fluoro-2-hexenyl)cyclohexyl)cyclohexyl)-4-methoxyethylcyclohexane 419. (E)-trans-(trans-4-(trans-4-(6-fluoro-3-hexenyl)cyclohexyl)cyclohexyl)-4-propylcyclohexane 420. (E)-trans-4-(trans-4-(trans-4-(6-fluoro-3-hexenyl)cyclohexyl)cyclohexyl)cyclohexanecarbonitrile 421. (E)-trans-(trans-4-(trans-4-(7-fluoroheptenyl)cyclohexyl)cyclohexyl)-4-methoxycyclohexane 422. (E)-trans-4-(trans-4-(trans-4-(7-fluoroheptenyl)cyclohexyl)cyclohexyl)cyclohexanecarbonitrile 423. (E)-trans-(trans-4-(trans-4-(7-fluoro-3-heptenyl)cyclohexyl)cyclohexyl)-4-butylcyclohexane 424. (E)-trans-4-(trans-4-(trans-4-(7-fluoro-3-heptenyl)cyclohexyl)cyclohexyl)cyclohexanecarbonitrile 425. (E)-trans-(trans-4-(trans-4-(7-fluoro-4-heptenyl)cyclohexyl)cyclohexyl)-4-methylcyclohexane Examples using the compound of the present invention as a component of the liquid crystal composition will be described hereinafter. In the respective use Examples, NI represents clearing point (° C.); $\Delta\epsilon$ represents a di-electric anisotropy value; $\Delta n$ represents an optical anisotropy value; $\eta$ represents a rotatory viscosity at 20° C. (cP); $V_{10}$ represents a threshold voltage (V); and K represents a ratio $(K_{33}/K_{11})$ of bend elastic coefficient $(K_{33})$ to splay elastic coefficient $(K_{11})$ at 20° C.

Example 14 (Use Example 1)

A liquid crystal composition, ZLI-1132 made by Merck Company, consisting of liquid crystal compounds of cyanophenylcyclohexane group ((4-(trans-4-propylcyclohexyl)benzonitrile (24% by weight), 4-(trans-4-pentylcyclohexyl)benzonitrile (36% by weight), 4-(trans-4-heptylcyclohexyl)benzonitrile (25% by weight) and 4-(trans-4-pentylcyclohexyl)-4'-cyanobiphenyl (15% by weight)) has the following physical properties:

NI: 72.4, $\Delta\epsilon$: 11.0, $\Delta n$: 0.137, $\eta$: 27.0, $V_{10}$: 1.78 in a cell thickness of 9 μm and K: 2.12.

With this composition (85% by weight) was mixed a compound of Example 1 (No. 1), (E)-4-(trans-4-(4-fluorobutenyl)cyclohexyl)benzonitrile (15% by weight), to obtain a nematic liquid crystal composition. The values of the physical properties of this composition were as follows:

NI: 69.6, $\Delta\epsilon$: 11.6, $\Delta n$: 0.138, $\eta$: 28.9, $V_{10}$: 1.68 in a cell thickness of 8.8 μm and K: 2.28.

This composition was allowed to stand in a freezer at −20° C., but neither deposition of crystals nor smectic phase were observed even after 60 days lapsed.

Example 15 (Use Example 2)

With the above liquid crystal composition, ZLI-1132 (85% by weight), was mixed a compound of Example 2 (No. 35), (E)-4-(trans-4-(4-fluorobutenyl)cyclohexyl)-4'-cyanobiphenyl (15% by weight), to obtain a nematic liquid crystal composition. The values of the physical properties of this composition were as follows:

NI: 91.0, $\Delta\epsilon$: 11.6, $\Delta n$: 0.155, $\eta$: 36.7, $V_{10}$: 1.91 in a cell thickness of 8.8 μm and K: 2.50.

This composition was allowed to stand in a freezer of −20° C., but neither of deposition of crystals nor smectic phase were observed even after 60 days lapsed.

Example 16 (Use Example 3)

A liquid crystal composition, ZLI-1083, made by Merck Company, consisting of liquid crystal compounds of cyanophenylcyclohexane group ((4-(trans-4-propylcyclohexyl)benzonitrile (30% by weight), 4-(trans-4-pentylcyclohexyl)benzonitrile (40% by weight) and 4-(trans-4-heptylcyclohexyl)benzonitrile (30% by weight)) has the following physical properties:

NI: 52.3, $\Delta\epsilon$: 10.7, $\Delta n$: 0.119, $\eta$: 21.7, $V_{10}$: 1.60 in a cell thickness of 9 μm and K: 2.10.

With this composition (85% by weight) was mixed a compound of Example 3 (No. 72), (E)-4-(trans-4-(4-fluorobutenyl)cyclohexyl)-4'-chlorobiphenyl (15% by weight), to obtain a nematic liquid crystal composition. The values of the physical properties of this composition were as follows:

NI: 65.4, $\Delta\epsilon$: 10.7, $\Delta n$: 0.131, $\eta$: 25.1, $V_{10}$: 1.66 in a cell thickness of 8.8 μm and K: 2.20.

This composition was allowed to stand in a freezer at $-20°$ C., but neither deposition of crystals nor smectic phase were observed even after 60 days lapsed.

Example 17 (Use Example 4)

With the above liquid crystal composition, ZLI-1132 (85% by weight) was mixed a compound of Example 13 (No. 373) ((E)-trans-(trans-4-(4-fluorobutenyl)cyclohexyl)-4-pentylcyclohexane) (15% by weight), to obtain a nematic liquid crystal composition. The values of the physical properties of this composition were as follows:

NI: 73.2, $\Delta\epsilon$: 9.5, $\Delta n$: 0.125, $\eta$: 23.5, $V_{10}$: 1.74 in a cell thickness of 8.7 μm and K: 1.90.

This composition was allowed to stand in a freezer at $-20°$ C., but neither deposition of crystals nor smectic phase were observed even after 60 days lapsed.

Example 18 (Use Example 5)

The physical properties of the nematic liquid crystal composition of Composition example 21 were as follows:

NI: 106.4, $\Delta\epsilon$: 5.2, $\Delta n$: 0.107, $\eta$: 28.4 and $V_{10}$: 2.28 in a cell thickness of 8.7 μm.

This composition was allowed in a freezer at $-20°$ C., but neither deposition of cells nor smectic phase were observed even after 60 days lapsed.

Example 19 (Use Example 6)

The physical properties of the nematic liquid crystal composition of Composition example 22 were as follows:

NI: 105.6, $\Delta\epsilon$: 4.2, $\Delta n$: 0.120, $\eta$: 27.1 and $V_{10}$: 2.57 in a cell thickness of 8.7 μm.

This composition was allowed to stand in a freezer at $-20°$ C., but neither deposition of crystals nor smectic phase were observed even after 60 days lapsed.

Example 20 (Use Example 7)

The physical properties of the nematic liquid crystal composition of Composition example 23 were as follows:

NI: 107.2, $\Delta\epsilon$: 5.2, $\Delta n$: 0.137, $\eta$: 26.1 and $V_{10}$: 2.51 in a cell thickness of 8.8 μm.

This composition was allowed to stand in a freezer at $-20°$ C., but neither deposition of crystals nor smectic phase were observed even after 60 days lapsed.

Example 21 (Use Example 8)

The physical properties of the nematic liquid crystal composition of Composition example 24 were as follows:

NI: 115.1, $\Delta\epsilon$: 4.6, $\Delta n$: 0.090, $\eta$: 26.2 and $V_{10}$: 2.38 in a cell thickness of 8.7 μm.

This composition was allowed in a freezer at $-20°$ C., but neither deposition nor smectic phase were observed even after 60 days lapsed.

Example 22 (Use Example 9)

The physical properties of the nematic liquid crystal composition of Composition example 25 were as follows:

NI: 57.9, $\Delta\epsilon$: 7.0, $\Delta n$: 0.082, $\eta$: 26.3 and $V_{10}$: 1.44 in a cell thickness of 8.7 μm.

This composition was allowed to stand at $-20°$ C., but neither deposition of crystals nor smectic phase were observed even after 60 days lapsed.

Example 23 (Use Example 10)

The physical properties of the nematic liquid crystal composition of Composition example 26 were as follows:

NI: 105.9, $\Delta\epsilon$: 9.4, $\Delta n$: 0.155, $\eta$: 29.7 and $V_{10}$: 1.83 in a cell thickness of 8.8 μm.

This composition was allowed to stand in a freezer at $-20°$ C., but neither deposition nor smectic phase were observed even after 60 days lapsed.

Example 24 (Use Example 11)

The physical properties of the nematic liquid crystal composition of Composition example 27 were as follows:

NI: 90.7, $\Delta\epsilon$: 7.1, $\Delta n$: 0.154, $\eta$: 23.9 and $V_{10}$: 2.05 in a cell thickness of 8.8 μm.

This composition was allowed to stand in a freezer at $-20°$ C., but neither deposition of crystals nor smectic phase were observed even after 60 days lapsed.

Example 25 (Use Example 12)

The physical properties of the nematic liquid crystal composition of Composition example 28 were as follows:

NI: 70.9, $\Delta\epsilon$: 10.8, $\Delta n$: 0.145, $\eta$: 36.8 and $V_{10}$: 1.37 in a cell thickness of 8.7 μm.

This composition was allowed to stand in a freezer at $-20°$ C., but neither deposition of crystals nor smectic phase were observed even after 60 days lapsed.

Example 26 (Use Example 13)

The physical properties of the nematic liquid crystal composition of Composition example 29 were as follows:

NI: 126.7, $\Delta\epsilon$: 6.4, $\Delta n$: 0.181, $\eta$: 42.2 and $V_{10}$: 2.39 in a cell thickness of 8.7 μm.

This composition was allowed to stand in a freezer at $-20°$ C., neither deposition of crystals nor smectic phase were observed even after 60 days lapsed.

Example 27 (Use Example 14)

The physical properties of the nematic liquid crystal composition of Composition example 30 were as follows:

NI: 106.6, $\Delta\epsilon$: 13.6, $\Delta n$: 0.138, $\eta$: 36.8 and $V_{10}$: 1.50 in a cell thickness of 8.7 μm.

This composition was allowed in a freezer at $-20°$ C., but neither deposition of crystals nor smectic phase were observed even after 60 days lapsed.

Example 28 (Use Example 15)

The physical properties of the nematic liquid crystal composition of Composition example 31 were as follows:

NI: 86.8, $\Delta\epsilon$: 8.9, $\Delta n$: 0.134, $\eta$: 23.3 and $V_{10}$: 1.86 in a cell thickness of 8.7 μm.

This composition was allowed to stand in a freezer at $-20°$ C., but neither deposition of crystals nor smectic phase were observed even after 60 days lapsed.

Example 29 (Use Example 16)

The physical properties of the nematic liquid crystal composition of Composition example 32 were as follows:

NI: 88.0, Δε: 8.6, Δn: 0.109, η: 33.1 and $V_{10}$: 1.57 in a cell thickness of 8.7 μm.

This composition was allowed to stand in a freezer at −20° C., but neither deposition of crystals nor smectic phase were observed even after 60 days lapsed.

Example 30 (Use Example 17)

The physical properties of the nematic liquid crystal composition of Composition example 33 were as follows:

NI: 79.7, Δε: 6.4, Δn: 0.154, η: 26.5 and $V_{10}$: 1.76 in a cell thickness of 8.7 μm.

This composition was allowed to stand in a freezer at −20° C., but neither deposition of crystals nor smectic phase were observed even after 60 days lapsed.

Example 31 (Use Example 18)

The physical properties of the nematic liquid crystal composition of Composition example 34 were as follows:

NI: 101.7, Δε: 8.0, Δn: 0.141, η: 44.8 and $V_{10}$: 1.77 in a cell thickness of 8.8 μm.

This composition was allowed to stand in a freezer at −20° C., but neither deposition of crystals nor smectic phase were observed even after 60 days lapsed.

Example 32 (Use Example 19)

The physical properties of the nematic liquid crystal composition of Composition example 35 were as follows:

NI: 62.1, Δε: 29.0, Δn: 0.159, η: 69.6 and $V_{10}$: 0.72 in a cell thickness of 8.7 μm.

This composition was allowed to stand in a freezer at −20° C., but neither deposition of crystals nor smectic phase were observed even after 60 days lapsed.

Example 33 (Use Example 20)

The physical properties of the nematic liquid crystal composition of Composition example 36 were as follows:

NI: 114.2, Δε: 3.8, Δn: 0.095, η: 21.6 and $V_{10}$: 2.86 in a cell thickness of 8.7 μm.

This composition was allowed to stand in a freezer at −20° C., but neither deposition of crystals nor smectic phase were observed even after 60 days lapsed.

Comparative Example 1 (Use Comparative Example 1)

With the above liquid crystal composition, ZLI-1132 (85% by weight) was mixed (E)-4-(trans-4-(butenyl)cyclohexyl)benzonitrile (Proc. 4th International Display Research Conference, San Diego, 231–234 (1984)), which has been said to have a large elastic constant, (15% by weight), to obtain a nematic liquid crystal composition.

The values of the physical properties of this composition were as follows:

NI: 69.1, Δε: 11.3, Δn: 0.137, η: 26.7 and $V_{10}$: 1.55 in a cell thickness of 8.7 μm and K: 2.20.

This composition together with the liquid crystal composition of Example 14 were allowed to stand in a freezer at −20° C. and in the case of the former, deposition of crystals was observed in 20 days, but in the case of the latter, neither deposition of crystals nor smectic phase were observed even after 60 days lapsed.

(Effectiveness of the Invention)

As seen from the above description either of the compounds of the present invention, i.e. compounds having a fluoroalkenyl group introduced into the molecule, have a high elastic constant ratio ($K_{33}/K_{11}$) and further, have an improved solubility thereof in other liquid crystal materials at low temperatures.

Thus, when the compounds of the present invention are used as a component of liquid crystal compositions, they have a characteristic of being superior in the solubility in other liquid crystal materials, and when the six-membered ring, substituent and/or bonding group thereof are suitably chosen, it is possible to provide a novel liquid crystal composition having desired physical properties.

What we claim is:

1. A liquid crystalline compound expressed by the formula (1)

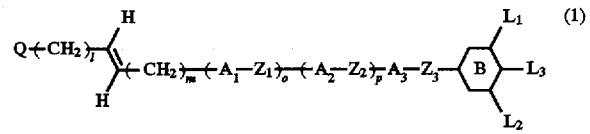

wherein Q represents $CF_3$; $A_1$, $A_2$ and $A_3$ each independently represent trans-1,4-cyclohexylene group, 1,4-phenylene group wherein one or more hydrogen atoms on its six-membered ring may be replaced by F, Cl or CN, pyridine-2,5-diyl group or 1,3-pyrimidine-2,5-diyl; ring B represents 1,4-phenylene group or trans-1,4-cyclohexylene group; $Z_1$, $Z_2$ and $Z_3$ each independently represent covalent bond, —CH=CH—, —C≡C—, —OCO—, —COO—, —$CH_2$O—, —O$CH_2$—, —($CH_2$)$_2$— or —($CH_2$)$_4$—; l and m each independently represent an integer of 0 to 5; o and p each independently represent 0 or 1; $L_1$ and $L_2$ each independently represent H, F or Cl; and $L_3$ represents a halogen atom, CN, $CF_3$, $CF_2$H, $CFH_2$, $OCF_3$ or $OCF_2$H.

2. A liquid crystal composition containing as a first component, at least one of the liquid crystalline compounds set forth in claim 1, and also containing as a second component, at least one compound chosen from those expressed by the following formulas (2), (3) and (4):

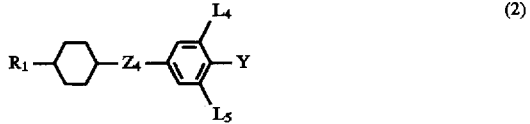

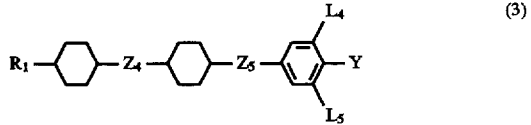

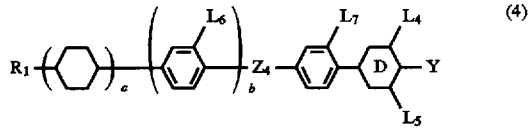

wherein $R_1$ represents an alkyl group of 1 to 10 carbon atoms; Y represents F, Cl, $CF_3$, $OCF_3$, $OCF_2$H or an alkyl group of 1 to 10 carbon atoms; $L_4$, $L_5$, $L_6$ and $L_7$ each independently represent H or F; $Z_4$ and $Z_5$ each independently represent —($CH_2$)$_2$—, —CH=CH— or a covalent bond; ring D represents a trans-1,4- cyclohexylene group or a 1,4-phenylene group; a represents 1 or 2; and b represents 0 or 1, and further containing as another second component, at least one compound chosen from those expressed by the following formulas (5), (6), (7), (8) and (9):

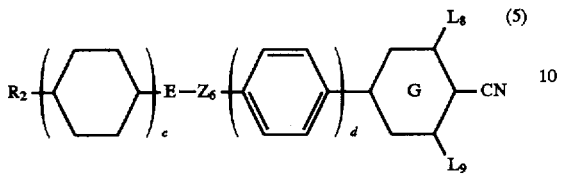 (5)

wherein $R_2$ represents F, an alkyl group of 1 to 10 carbon atoms or an alkenyl group of 2 to 10 carbon atoms wherein optional methylene groups (—$CH_2$—) may be replaced by oxygen atom (—O—), but two or more methylene groups should not be continuedly replaced by oxygen atom; $Z_6$ represents —$(CH_2)_2$—, —COO— or a covalent bond; $L_8$ and $L_9$ each independently represent H or F; E represents a trans-1,4-cyclohexylene group, a 1,4-phenylene group or a 1,3-dioxane-2,5-diyl group; ring G represents a trans-1,4-cyclohexylene group or a 1,4-phenylene group; and c and d each independently represent 0 or 1,

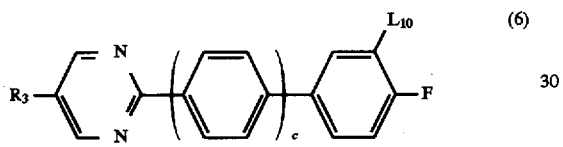 (6)

wherein $R_3$ represents an alkyl group of 1 to 10 carbon atoms; $L_{10}$ represents H or F; and e represents 0 or 1,

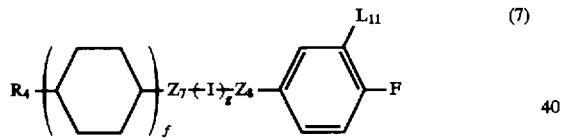 (7)

wherein $R_4$ represents an alkyl group of 1 to 10 carbon atoms; I represents a trans-1,4-cyclohexylene group or a 1,4-phenylene group; $L_{11}$ represents H or F; $Z_7$ represents —COO— or a covalent bond; $Z_8$ represents —COO— or —C≡C—; and f and g each independently represent 0 or 1, $R_5$—J—$Z_9$—K—$R_6$ (8)

wherein $R_5$ and $R_6$ each independently represent an alkyl group, an alkoxy group or an alkoxymethyl group each of 1 to 10 carbon atoms; J represents a trans-1,4-cyclohexylene group, a 1,4-phenylene group or a 1,3-pyrimidine-2,5-diyl group; K represents a trans-1,4-cyclohexylene group or a 1,4-phenylene group; and $Z_9$ represents —C≡C—, —COO—, —$(CH_2)_2$— or a covalent bond,

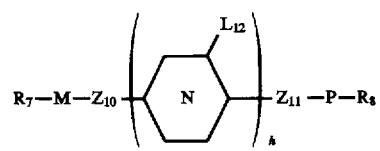 (9)

wherein $R_7$ represents an alkyl group or an alkoxy group each of 1 to 10 carbon atoms; $R_8$ represents an alkyl group of 1 to 10 carbon atoms; wherein optional methylene groups (—$CH_2$—) may be replaced by oxygen atom (—O—), but two or more methylene groups should not be continuedly replaced by oxygen atom; M represents a trans-1,4-cyclohexylene group or a 1,3-pyrimidine-2,5-diyl group; rings N and P each independently represent a trans-1,4-cyclohexylene group or a 1,4-phenylene group; $Z_{10}$ represents —COO—, —$(CH_2)_2$—, —CH=CH— or a covalent bond; $Z_{11}$ represents —C≡C—, —COO— or a covalent bond; h represents 0 or 1; and $L_{12}$ represents H or F.

3. A liquid crystal composition containing at least one of the liquid crystalline compounds set forth in claim 1.

4. A liquid crystal composition containing as a first component, at least one of the liquid crystalline compounds set forth in claim 1, and also containing as a second component, at least one compound chosen from those expressed by the following formulas (2), (3) or (4):

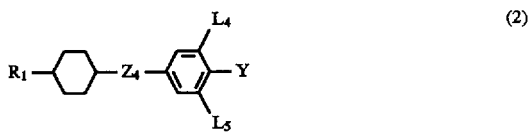 (2)

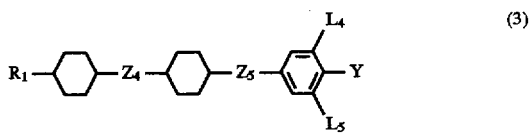 (3)

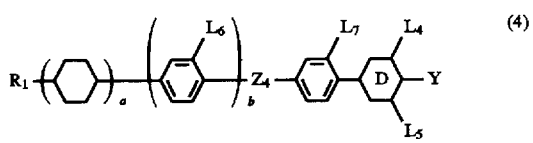 (4)

wherein $R_1$ represents an alkyl group of 1 to 10 carbon atoms; Y represents F, Cl, $CF_3$, $OCF_3$, $OCF_2H$ or an alkyl group of 1 to 10 carbon atoms; $L_4$, $L_5$, $L_6$ and $L_7$ each independently represent H or F; $Z_4$ and $Z_5$ each independently represent —$(CH_2)_2$—, —CH=CH— or covalent bond; ring D represents trans-1,4-cyclohexylene group or 1,4-phenylene group; a represents 1 or 2; and b represents 0 or 1.

5. A liquid crystal composition containing as a first component, at least one of the liquid crystalline compounds set forth in claim 1, and also containing as a second component, at least one compound chosen from those expressed by the following formulas (5), (6), (7), (8) and (9):

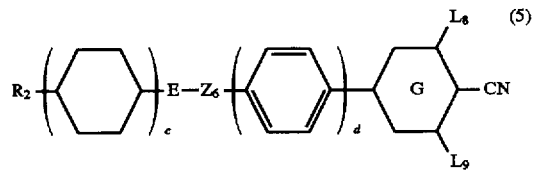 (5)

wherein $R_2$ represents F, an alkyl group of 1 to 10 carbon atoms or an alkenyl group of 2 to 10 carbon atoms wherein optional methylene groups (—$CH_2$—) may be replaced by oxygen atom (—O—), but two or more methylene groups should not be continuedly replaced by oxygen atom; $Z_6$ represents —$(CH_2)_2$—, —COO— or covalent bond; $L_8$ and $L_9$ each independently represent H or F; E represents trans-1,4-cyclohexylene group, 1,4-phenylene group or 1,3-dioxane-2,5-diyl group; ring G represents trans-1,4-cyclohexylene group or 1,4-phenylene group; and c and d each independently represent 0 or 1,

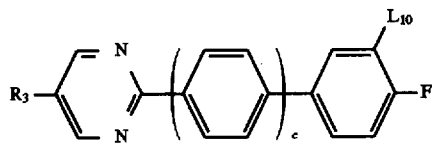

(6)

wherein $R_3$ represents an alkyl group of 1 to 10 carbon atoms; $L_{10}$ represents H or F; and e represents 0 or 1,

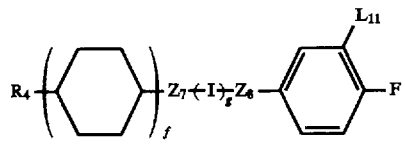

(7)

wherein $R_4$ represents an alkyl group of 1 to 10 carbon atoms; I represents trans-1,4-cyclohexylene group or 1,4-phenylene group; $L_{11}$ represents H or F; $Z_7$ represents —COO— or covalent bond; $Z_8$ represents —COO— or —C≡C—; and f and g each independently represent 0 or 1,

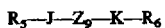

(8)

wherein $R_5$ and $R_6$ each independently represent an alkyl group, an alkoxy group or an alkoxymethyl group each of 1 to 10 carbon atoms; J represents trans-1,4-cyclohexylene group, 1,4-phenylene group or 1,3-pyrimidine-2,5-diyl group; K represents trans-1,4-cyclohexylene group or 1,4-phenylene group; and $Z_9$ represents —C≡C—, —COO—, —(CH$_2$)$_2$— or covalent bond,

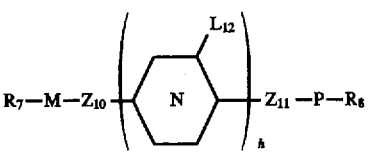

(9)

wherein $R_7$ represents an alkyl group or an alkoxy group each of 1 to 10 carbon atoms; $R_8$ represents an alkyl group of 1 to 10 carbon atoms; wherein optional methylene groups (—CH$_2$—) may be replaced by oxygen atom (—O—), but two or more methylene groups should not be continuedly replaced by oxygen atom; M represents trans-1,4-cyclohexylene group or 1,3-pyrimidine-2,5-diyl group; rings N and P each independently represent trans-1,4-cyclohexylene group or 1,4-phenylene group; $Z_{10}$ represents —COO—, —(CH$_2$)$_2$—, —CH=CH— or covalent bond; $Z_{11}$ represents —C≡C—, —COO— or covalent bond; h represents 0 or 1; and $L_{12}$ represents H or F.

6. A liquid crystal display element comprising a liquid crystal composition set forth in claim 3.

7. A liquid crystal display element comprising a liquid crystal composition set forth in claim 4.

8. A liquid crystal display element comprising a liquid crystal composition set forth in claim 5.

9. A liquid crystal display element comprising a liquid crystal composition set forth in claim 2.

\* \* \* \* \*